US008562988B2

(12) United States Patent
Chang et al.

(10) Patent No.: US 8,562,988 B2
(45) Date of Patent: *Oct. 22, 2013

(54) STRATEGIES FOR IMPROVED CANCER VACCINES

(75) Inventors: Chien-Hsing Chang, Downingtown, PA (US); David M. Goldenberg, Mendham, NJ (US)

(73) Assignee: IBC Pharmaceuticals, Inc., Morris Plains, NJ (US)

( * ) Notice: Subject to any disclaimer, the term of this patent is extended or adjusted under 35 U.S.C. 154(b) by 109 days.

This patent is subject to a terminal disclaimer.

(21) Appl. No.: 12/754,740

(22) Filed: Apr. 6, 2010

(65) Prior Publication Data

US 2010/0189641 A1    Jul. 29, 2010

Related U.S. Application Data

(60) Continuation-in-part of application No. 12/544,476, filed on Aug. 20, 2009, now Pat. No. 7,901,680, and a continuation-in-part of application No. 12/396,605, filed on Mar. 3, 2009, now Pat. No. 7,858,070, which is a division of application No. 11/633,729, filed on Dec. 5, 2006, now Pat. No. 7,527,787, which is a continuation-in-part of application No. 11/389,358, filed on Mar. 24, 2006, now Pat. No. 7,550,143, and a continuation-in-part of application No. 11/391,584, filed on Mar. 28, 2006, now Pat. No. 7,521,056, and a continuation-in-part of application No. 11/478,021, filed on Jun. 29, 2006, now Pat. No. 7,534,866.

(60) Provisional application No. 61/090,487, filed on Aug. 20, 2008, provisional application No. 60/782,332, filed on Mar. 14, 2006, provisional application No. 60/728,292, filed on Oct. 19, 2005, provisional application No. 60/751,196, filed on Dec. 16, 2005, provisional application No. 60/751,196, filed on Dec. 16, 2005, provisional application No. 60/864,530, filed on Nov. 6, 2006, provisional application No. 61/168,290, filed on Apr. 10, 2009.

(51) Int. Cl.
| | |
|---|---|
| *A61K 39/00* | (2006.01) |
| *A61K 39/44* | (2006.01) |
| *A61K 39/395* | (2006.01) |
| *A61K 39/385* | (2006.01) |
| *A61K 39/38* | (2006.01) |
| *A61K 38/17* | (2006.01) |
| *C07K 16/28* | (2006.01) |
| *C07K 16/46* | (2006.01) |

(52) U.S. Cl.
USPC ............... 424/134.1; 424/143.1; 424/184.1; 424/185.1; 424/193.1

(58) Field of Classification Search
None
See application file for complete search history.

(56) References Cited

U.S. PATENT DOCUMENTS

| | | | |
|---|---|---|---|
| 4,046,722 A | 9/1977 | Rowland | |
| 4,699,784 A | 10/1987 | Shih et al. | |
| 4,818,709 A | 4/1989 | Primus et al. | |
| 4,868,109 A | 9/1989 | Lansdorp et al. | |
| 5,194,254 A | 3/1993 | Barber et al. | |
| 5,478,556 A | 12/1995 | Elliott et al. | |
| 5,530,101 A | 6/1996 | Queen et al. | |
| 5,571,515 A | 11/1996 | Scott et al. | |
| 5,614,610 A | 3/1997 | Hellstrom et al. | |
| 5,770,198 A | 6/1998 | Coller et al. | |
| 5,798,100 A | 8/1998 | Hansen | |
| 5,874,540 A | 2/1999 | Hansen et al. | |
| 6,132,718 A | 10/2000 | Hansen | |
| 6,261,537 B1 | 7/2001 | Klaveness et al. | |
| 6,306,393 B1 | 10/2001 | Goldenberg et al. | |
| 6,440,416 B1 | 8/2002 | Hansen et al. | |
| 6,524,854 B1 | 2/2003 | Monia et al. | |
| 6,617,135 B1 | 9/2003 | Gillies et al. | |
| 6,926,893 B1 | 8/2005 | Hansen | |
| 7,030,228 B1 * | 4/2006 | Schmitz et al. | ............ 530/389.6 |
| 7,060,506 B2 | 6/2006 | Craig | |
| 7,151,164 B2 | 12/2006 | Hansen et al. | |
| 7,312,318 B2 | 12/2007 | Hansen et al. | |
| 7,354,587 B1 | 4/2008 | Hansen | |
| 7,521,056 B2 | 4/2009 | Chang et al. | |
| 7,527,787 B2 | 5/2009 | Chang et al. | |

(Continued)

FOREIGN PATENT DOCUMENTS

| | | |
|---|---|---|
| EP | 0324625 A1 | 7/1989 |
| EP | 0340793 B1 | 8/1995 |

(Continued)

OTHER PUBLICATIONS

Tabi et al, Advanced Drug Delivery Reviews 58: 902-915, 2006.*

(Continued)

*Primary Examiner* — Phuong Huynh
(74) *Attorney, Agent, or Firm* — Richard A. Nakashima

(57) ABSTRACT

The present invention concerns methods and compositions for forming anti-cancer vaccine complexes. In preferred embodiments, the anti-cancer vaccine complex comprises an antibody moiety that binds to dendritic cells, such as an anti-CD74 antibody or antigen-binding fragment thereof, attached to an AD (anchoring domain) moiety and a xenoantigen, such as CD20, attached to a DDD (dimerization and docking domain) moiety, wherein two copies of the DDD moiety form a dimer that binds to the AD moiety, resulting in the formation of the vaccine complex. The anti-cancer vaccine complex is capable of inducing an immune response against xenoantigen expressing cancer cells, such as $CD138^{neg}CD20^+$ MM stem cells, and inducing apoptosis of and inhibiting the growth of or eliminating the cancer cells.

16 Claims, 17 Drawing Sheets

(56) References Cited

U.S. PATENT DOCUMENTS

| | | | |
|---|---|---|---|
| 7,534,866 B2 | 5/2009 | Chang et al. | |
| 7,541,440 B2 | 6/2009 | Goldenberg et al. | |
| 7,550,143 B2 | 6/2009 | Goldenberg et al. | |
| 2003/0198956 A1 | 10/2003 | Makowski et al. | |
| 2003/0228326 A1* | 12/2003 | Palomba et al. | 424/185.1 |
| 2003/0232420 A1 | 12/2003 | Braun et al. | |
| 2004/0018587 A1 | 1/2004 | Makowski et al. | |
| 2005/0003403 A1 | 1/2005 | Rossi et al. | |
| 2005/0003533 A1* | 1/2005 | Kalinski | 435/372 |
| 2005/0063952 A1* | 3/2005 | Klysner et al. | 424/93.2 |
| 2005/0118142 A1* | 6/2005 | Ildstad | 424/93.7 |
| 2006/0210475 A1 | 9/2006 | Goldenberg et al. | |
| 2007/0020259 A1 | 1/2007 | Hansen et al. | |
| 2007/0140966 A1 | 6/2007 | Chang et al. | |
| 2008/0152648 A1* | 6/2008 | Kretz-Rommel et al. | 424/133.1 |
| 2009/0060862 A1 | 3/2009 | Chang et al. | |
| 2009/0111143 A1 | 4/2009 | Goldenberg et al. | |
| 2010/0034834 A1* | 2/2010 | Robbins et al. | 424/174.1 |

FOREIGN PATENT DOCUMENTS

| | | |
|---|---|---|
| EP | 0438803 B1 | 3/1997 |
| EP | 0306995 B1 | 4/1997 |
| WO | 91/11465 A1 | 8/1991 |
| WO | 92/15322 A1 | 9/1992 |
| WO | 93/11162 A1 | 6/1993 |
| WO | 94/05329 A1 | 3/1994 |
| WO | 96/04313 A1 | 2/1996 |
| WO | 96/37224 A1 | 11/1996 |
| WO | 96/40941 A1 | 12/1996 |
| WO | 00/68248 | 11/2000 |
| WO | 2006/107617 | 10/2006 |
| WO | 2006/107786 | 10/2006 |
| WO | 2007/075270 | 7/2007 |
| WO | 2008/033413 | 3/2008 |
| WO | 2010002225 | 2/2010 |

OTHER PUBLICATIONS

Kimura et al, Molecular Therapy 15(7): 1390-1399, Jul. 2007.*
Riemer et al, Mol. Immunol. 42: 1121-1124, 2005.*
Stancoviski et al, Proceedings of the National Academy of Science USA 88: 8691-8695, 1991.*
Tacken et al, Blood 106(4): 1278-1284, Aug. 15, 2005.*
Grunewald et al, PNAS 105(32): 11276-11280, Aug. 2008.*
Goldszmith et al, J Immunology 171: 5940-5947, 2003.*
Stuhler et al, Eur J Immunol 23: 2279-2286, 1993.*
Tacken et al, Nature Reviews Immunology 7: 790-802, Oct. 2007.*
Abbas et al., Cellular and Molecular Immunology, W.B. Saunders Comp. 1991, p. 43.
Alto et al., "Bioinformatic design of A-kinase anchoring protein-in silico: a potent and selective peptide antagonist of type II protein kinase A anchoring" Proc. Natl. Acad. Sci USA Apr. 15, 2003; 100(8):4445-50.
Backer et al., "Self-Assembled "Dock and Lock" System for Linking Payloads to Targeting Proteins" Bioconjugate Chem., 2006, 17(4):912-919.
Baillie et al., "Compartmentalisation of phospodiesterases and protein kinase A: opposites attract", FEBS Letters 2005; 579:3264-3270.
Banky et al., "Dimerization/Docking Domain of the Type Iα Regulatory Subunit of cAMP-dependent Protein Kinase", J. Biol. Chem. 273:35048-55, 1998.
Basu et al., "Structure-Function Engineering of Interferon-β-1b for Improving Stability, Solubility, Potency, Immunogenicity, and Pharmacokinetic Properties by Site-Selective Mono-PEGylation", Bioconjugate Chem. 2006; 17:618-630.
Belardelli et al., "Interferon-alpha in tumor immunity and immunotherapy" Cytokine Growth Factor Rev. 13(2):119-134 (2002).
Belardelli et al., "International Meeting on Cancer Vaccines: How Can We Enhance Efficacy of Therapeutic Vaccines?" Cancer Res. 64:6827-6830 (2004).

Belardelli et al., "The neglected role of type I interferon in the T-cell response: implications for its clinical use" Immunol. Today 17(8):369-72 (1996).
Biron et al., "Natural killer cells in antiviral defense: function and regulation by innate cytokines" Annu. Rev. Immunol. 17:189-220 (1999).
Brunda et al., "Modulation of Murine Natural Killer Cell Activity in Vitro and in Vivo by Recombinant Human Interferons" Cancer Res. 44:597-601 (1984).
Burns-Hamuro et al., "Distinct interaction modes of an AKAP bound to two regulatory subunit isoforms of protein kinase A revealed by amide hydrogen/deuterium exchange" Protein Science (2005), 14:2982-2992.
Carr et al., "Interaction of the Regulatory Subunit (RII) of cAMP-dependent Protein Kinase with RII-anchoring Proteins Occurs through an Amphipathic Helix Binding Motif", J. Biol. Chem. 266:14188-92 (1991).
Carr et al., "Identification of Sperm-specific Proteins That Interact with A-kinase Anchoring Proteins in a Manner Similar to the Type II Regulatory Subunit of PKA" J. Biol. Chem. 276(20):17332-17338 (2001).
Carrero et al., "Lymphocytes are detrimental during the early innate immune response against Listeria monocytogenes" J. Exp. Med. 203(4):933-940 (2006).
Chang et al., "The Dock and Lock Method: A Novel Platform Technology for Building Multivalent, Multifunctional Structures of Defined Composition with Retained Bioactivity" Clin. Cancer Res. Sep. 15, 2007;13(18 Suppl), pp. 5586-5591.
Chmura et al., "Antibodies with infinite affinity" Proc. Natl. Acad. Sci. USA 98(15):8480-8484 (2001).
Colledge et al., "AKAPs: from structure to function", Trends Cell Biol. 6:216-21 (1999).
Corbin et al., "Regulation of Adenosine 3',5'-Monophosphate-dependent Protein Kinase", J. Biol. Chem. 248:1813-21 (1973).
Dhalluin et al., "Structural and Biophysical Characterization of the 40 kDa PEG-Interferon-α2a and Its Individual Positional Isomers" Bioconjugate Chem. 2005;16:504-517.
Dodart et al., "Immunotherapy for Alzheimer's Disease: will vaccination work?" Trends Mol. Med. 9(3):85-87 (2003).
Doherty et al., "Site-Specific PEGylation of Engineered Cysteine Analogues of Recombinant Human Granulocyte-Macrophage Colony-Stimulating Factor", Bioconjugate Chem. 2005;16:1291-1298.
Ferrantini et al., "IFN-α1 Gene Expression into a Metastatic Murine Adenocarcinoma (TS/A) Results in CD8+ T Cell-Mediated Tumor Rejection and Development of Antitumor Immunity" J. Immunol. 153:4604-15 (1994).
Ferrantini et al., "Interferon-α and cancer: Mechanisms of action and new perspectives of clinical use" Biochimie 89: 884-893 (2007).
Gillies et al., "High-level expression of chimeric antibodies using adapted cDNA variable region cassettes", J. Immunol. Methods 125 (1989) 191-202.
Glennie et al., "Mechanisms of killing by anti-CD20 monoclonal antibodies" Mol. Immunol. 44:3823-3837 (2007).
Gold et al., "A Novel Bispecific, Trivalent Antibody Construct for Targeting Pancreatic Carcinoma", Cancer Res. 68:4819-26, 2008.
Gold et al., "Molecular Basis of AKAP Specificity for PKA Regulatory Subunits" Mol. Cell Nov. 3, 2006;24(3):383-95.
Goldenberg et al., "Multifunctional Antibodies by the Dock-and-Lock Method for Improved Cancer Imaging and Therapy by Pretargeting", J. Nucl. Med. 49:158-63, 2008.
Goldenberg et al., "Properties and structure-function relationships of veltuzumab (hA20), a humanized anti-CD20 monoclonal antibody" Blood 113:1062-70 (2009).
Goodson et al., "Site-Directed PEGylation of Recombinant Interleukin-2 at its Glycosylation Site", Nat. Biotechnology Apr. 1990;8(4):343-6.
Grace et al., "Site of Pegylation and Polyethylene Glycol Molecule Size Attenuate Interferon-α Antiviral and Antiproliferative Activities through the JAK/STAT Signaling Pathway" J. Biol. Chem. 2005;280(8):6327-6336.

(56) References Cited

OTHER PUBLICATIONS

Grimley et al., "Prolonged STAT1 Activation Related to the Growth Arrest of Malignant Lymphoma Cells by Interferon-α" Blood 91(8):3017-27 (1998).
Gutterman et al., "Leukocyte Interferon-Induced Tumor Regression in Human Metastatic Breast Cancer, Multiple Myeloma, and Malignant Lymphoma" Ann. Intern. Med. 93(3):399-406 (1980).
Gutterman et al., "Cytokine therapeutics: Lessons from interferon α" Proc. Natl. Acad. Sci. USA 91:1198-205 (1994).
Harris et al., "Effect of pegylation on pharmaceuticals" Nat. Rev. Drug. Discov. 2:214-221 (2003).
Hausken et al. "Mutational Analysis of the A-Kinase Anchoring Protein (AKAP)-binding Site on RII", J. Biol. Chem. 271:29016-22 (1996).
Hodneland et al., "Selective immobilization of proteins to self-assembled monolayers presenting active site-directed capture ligands", Proc. Natl. Acd. Sci. USA 2002; 99:5048-5052.
Huang et al., "Targeting IFN-α to B Cell Lymphoma by a Tumor-Specific Antibody Elicits Potent Antitumor Activities" J. Immunol. 179:6881-88 (2007).
Hundsrucker et al., "High-affinity AKAP7δ-protein kinase A interaction yields novel protein kinase A-anchoring disruptor peptides" Biochem. J. (2006) 396, 297-306.
Kimby et al., "Long-term molecular remissions in patients with indolent lymphoma treated with rituximab as a single agent or in combination with interferon alpha-2a: A randomized phase II study from the Nordic Lymphoma Group" Leuk. Lymphoma 49(1):102-112 (2008).
Kinderman et al., "A Dynamic Mechanism for AKAP Binding to RII Isoforms of cAMP-Dependent Protein Kinase" Mol. Cell 24(3):397-408 (2006).
Kinstler et al., "Characterization and Stability of N-terminally PEGylated rhG-CSF" Pharm. Res. 1996;13 (7):996-1002.
Kramer et al., "Cell and virus sensitivity studies with recombinant human alpha interferons" J. Interferon. Res. 3 (4):425-35 (1983).
Le Bon et al., "Type I Interferons Potently Enhance Humoral Immunity and Can Promote Isotype Switching by Stimulating Dendritic Cells in Vivo" Immunity 14:461-470 (2001).
Lee et al., "Solid-Phase PEGylation of Recombinant Interferon α-2a for Site-Specific Modification: Process Performance, Characterization, and in Vitro Bioactivity" Bioconjugate Chem. 2007; 18:1728-34.
Lohmann et al., "High-affinity binding of the regulatory subunit (RII) of cAMP-dependent protein kinase to microtubule-associated and other cellular proteins", Proc. Natl. Acad. Sci. USA 81:6723-27 (1984).
Luft et al., "Type I IFNs Enhance the Terminal Differentiation of Dendritic Cells" J. Immunol. 161:1947-1953 (1998).
Mason, Anthony J., "Functional Analysis of the Cysteine Residues of Activin A", Mol. Endocrinol. 8:325-32, 1994.
Matarrese et al., "Type I Interferon Gene Transfer Sensitizes Melanoma Cells to Apoptosis via a Target Activity on Mitochondrial Function" Am. J. Pathol. 2002, 160(4):1507-1520.
Mecchia et al., "Type I consensus interferon (CIFN) gene transfer into human melanoma cells up-regulates p53 and enhances cisplatin-induced apoptosis: implications for new therapeutic strategies with IFN-alpha" Gene Ther. (2000) 7, 167-179.
Newlon et al., "A Novel Mechanism of PKA Anchoring Revealed by Solution Structures of Anchoring Complexes", EMBO J. 2001; 20:1651-1662.
Newlon et al., "The molecular basis for protein kinase A anchoring revealed by solution NMR", Nature Struct. Biol. 1999; 3:222-227.
Ngo et al., "Computational Complexity, Protein Structure Prediction, and the Levinthal Paradox", The Protein Folding Problem and Tertiary Structure Prediction, Ch. 14, pp. 492-495, (Mertz & Le Grand, Eds.), Birkhauser Boston, 1994.
Osborn et al., "Pharmacokinetic and Pharmacodynamic Studies of a Human Serum Albumin-Interferon-α Fusion Protein in Cynomolgus Monkeys" J. Pharmacol. Exp. Ther. 303(2):540-548 (2002).
Oyen et al., "Human testis cDNA for the regulatory subunit RIIα of cAMP-dependent protein kinase encodes an alternate amino-terminal region", FEBS Letters 246:57-64, 1989.
Ozzello et al., "Conjugation of interferon alpha to a humanized monoclonal antibody (HuBrE-3vI) enhances the selective localization and antitumor effects of interferon in breast cancer xenografts" Breast Cancer Res. Treat. 48: 135-147 (1998).
Paquette et al., "Interferon-α and granulocyte-macrophage colony-stimulating factor differentiate peripheral blood monocytes into potent antigen-presenting cells" J. Leukoc. Biol. 64:358-367; 1998.
Pelham et al., "Interferon-α conjugation to human osteogenic sarcoma monoclonal antibody 791T/36" Cancer Immunol. Immuother 1983;15(3):210-216.
Pepinsky et al., "Improved Pharmacokinetic Properties of a Polyethylene Glycol-Modified Form of Interferon-β-1a with Preserved in Vitro Bioactivity" Pharmacol. Exp. Ther. 2001; 297(3):1059-1066.
Pilling et al., "Interferon-β mediates stromal cell rescue of T cells from apoptosis" Eur. J. Immunol. 29:1041-1050 (1999).
Rabjohn et al., "Molecular Cloning and Epitope Analysis of the Peanut Allergen Ara h 3" J. Clinical Investigation 103 (4):535-542 (1999).
Raefsky et al., "Studies of Interferon as a regulator of hematopoietic cells proliferation" J. Immunol. 135 (4):2507-2512 (1985).
Rose et al., "Structural basis of dimerization, coactivator recognition and MODY3 mutations in HNF-1α", Nature Struct. Biol. 2000; 7:744-748.
Rosendahl et al., "A Long-Acting, Highly Potent Interferon α-2 Conjugate Created Using Site-Specific PEGylation" Bioconjugate Chem. 2005;16:200-207.
Rossi et al. "Novel Designs of Multivalent Anti-CD20 Humanized Antibodies as Improved Lymphoma Therapeutics", Cancer Res. 68:8384-92, 2008.
Rossi et al., "Stably tethered multifunctional structures of defined composition made by the dock and lock method for use in cancer targeting" Proc. Natl. Acad. Sci. Epub Apr. 24, 2006, vol. 103, No. 18, pp. 6841-6846.
Rustandi et al., "The Ca2+-Dependent Interaction of S100B(ββ) with a Peptide Derived from p53", Biochemistry 1998; 37: 1951-1960.
Sabaawy et al., "Enhancement of 5-fluorouracil cytotoxicity on human colon cancer cells by retrovirus-mediated interferon-α gene transfer" Int. J. Oncol. Jun. 1999; 14(6):1143-51.
Salles et al., "Rituximab combined with chemotherapy and interferon in follicular lymphoma patients: results of the GELA-GOELAMS FL2000 study" Blood 2008; 112:4824-4831.
Santini et al., "Type I Interferon as a Powerful Adjuvant for Monocyte-derived Dendritic Cell Development and Activity in Vivo and in Hu-PBL-SCID Mice" J. Exp. Med. 191(10):1777-1788 (2000).
Scott et al., "Type II Regulatory Subunit Dimerization Determines the Subcellular Localization of the cAMP-dependent Protein Kinase", J. Biol. Chem. 265:21561-66 (1990).
Scott et al., "Cyclic nucleotide-dependent protein kinases" Pharmacol. Ther. 1991;50(1):123-45.
Seffernick et al., "Melamine Deaminase and Atrazine Chlorohydrolase: 98 Percent Identical but Functionally Different" J. Bacteriol. 183(8):2405-2410 (2001).
Sharkey et al., "Improved Therapeutic Results by Pretargeted Radioimmunotherapy of Non-Hodgkin's Lymphoma with a New Recombinant, Trivalent, Anti-CD20, Bispecific Antibody", Cancer Res. 68:5282-90, 2008.
Sharkey et al., "Metastatic Human Colonic Carcinoma: Molecular Imaging with Pretargeted SPECT and PET in a Mouse Model", Radiology 246:497-507, 2008.
Sidky et al., "Inhibition of Angiogenesis by Interferons: Effects on Tumor- and Lymphocyte-induced Vascular Responses" Cancer Res. 47:5155-5161, Oct. 1, 1987.
Stein et al., "Characterization of a New Humanized Anti-CD20 Monoclonal Antibody, IMMU-106, and Its Use in Combination with the Humanized Anti-CD22 Antibody, Epratuzumab, for the Therapy of Non-Hodgkin's Lymphoma" Clin. Cancer Res. vol. 10, 2868-2878, Apr. 15, 2004.

(56) References Cited

OTHER PUBLICATIONS

Stein et al., "Characterization of a humanized IgG4 anti—HLA-DR monoclonal antibody that lacks effector cell functions but retains direct antilymphoma activity and increases the potency of rituximab" Blood 2006;108:2736-2744.
Stokka et al., "Characterization of A-kinase-anchoring disruption using a solution-based assay" Biochem. J. (2006) 400, 493-499.
Stryer et al., "Levels of Structure in Protein Architecture", Biochemistry, 3rd Ed., pp. 31-33, W.H. Freeman & Co., New York, 1988.
Takaoka et al., "Integration of interferon-a$\alpha/\beta$ signalling to p53 responses in tumour suppression and antiviral defence" Nature Jul. 31, 2003;424(6948):516-23.
Taylor, S., "cAMP-dependent Protein Kinase" J. Biol. Chem. 1989;264(15):8443-8446.
Walsh et al., "An Adenosine 3', 5'-Monophosphate-dependant Protein Kinase from Rabbit Skeletal Muscle" J. Biol. Chem. 243(13):3763-3774 (1968).
Weck et al., "Comparison of the Antiviral Activities of Various Cloned Human Interferon-$\alpha$ Subtypes in Mammalian Cell Cultures" J. Gen. Virol. (1981), 57, 233-237.
Winkler et al., "Changing the Antigen Binding Specificity by Single Point Mutations of an Anti-p24 (HIV-1) Antibody", J. Immunol. 165:4505-14, 2000.
Witkowski et al., "Conversion of a $\beta$-Ketoacyl Synthase to a Malonyl Decarboxylase by Replacement of the Active-Site Cysteine with Glutamine" Biochemistry 38(36):11643-50 (1999).
Wong et al., "AKAP Signalling Complexes: Focal Points in Space and Time", Nat. Rev. Mol. Cell Biol. 12:959-70 (2004).
Zhu et al., "Inhibition of tumor growth and metastasis by targeting tumor-associated angiogenesis with antagonists to the receptors of vascular endothelial growth factor", Invest. New Drugs 17:195-212, 1999.
Amigorena et al., "Transient accumulation of new class II MHC molecules in a novel endocytic compartment in B lymphocytes" Nature 369:113-120 (1994).
Becker et al., "Expression of a Hybrid Immunoglobulin-T Cell Receptor Protein in Transgenic Mice", Cell, 58:911-921 (Sep. 1989).
Becker, S., "Inteferon-$\gamma$ Accelerates Immune Proliferation via Its Effect on Monocyte HLA-DR Expression", Cell. Immunol. Mar. 1985;91(1):301-7.
Bohlen et al., "Idiotype vaccination strategies against a murine B-cell lymphoma: Dendritic cells loaded with idiotype and bispecific idiotype x anti-class II antibodies can protect against tumor growth", Cytokines Mol. Ther. Dec. 1996;2 (4):231-8.
Bolhuis et al., "T Cell Targeting in Cancer Therapy", Cancer Immunol. Immunother., 34:1-8 (1991).
Bolhuis et al., "Engineering T Lymphocyte Antigen Specificity", J. Cell. Biochem. 47:306-310, (1991).
Bremnes et al., "An LI and ML motif in the cytoplasmic tail of the MHC-associated invariant chain mediate rapid internalization", J. Cell. Science 107:2021-2032 (1994).
Burnett et al., " Human Monoclonal Antibodies to Defined Antigens", Human Hybridomas & Monoclonal Antibodies (Engelman et al, eds.) Plenum Press, New York, 1985, pp. 114-115.
Carayanniotis et al., "Delivery of synthetic peptides by anti-class II MHC monovalent antibodies induces specific adjuvant-free IgG responses in vivo", Mol. Immunol. 25(9):907-911 (1988).
Chen et al., "Novel strategies for improved cancer vaccines", Expert Rev. Vaccines 8(5):567-76 (2009).
Cohen et al., "Cancer Vaccines Get a Shot in the Arm", Science 262:841-843 (1993).
Durrant et al., "An idiotypic replica of carcinoembryonic antigen inducing cellular and humoral responses directed against human colorectal tumours", Int. J. Cancer 50:811-816 (1992).
Eshhar et al., "Chimeric T cell receptor which incorporates the anti-tumour specificity of a monoclonal antibody with the cytolytic activity of T cells: a model system for immunotherapeutical approach", Br. J. Cancer 62:27-29, 1990.
Eshhar et al., "Specific activation and targeting of cytotoxic lymphocytes through chimeric single chains consisting of antibody-binding domains and the $\gamma$ or $\zeta$ subunits of the immunoglobulin and T-cell receptors", Proc. Natl. Acad. Sci. USA, 90:720-724 (1993).
Fagerberg et al., "Induction of an immune network cascade in cancer patients treated with monoclonal antibodies (ab1)", Cancer Immunol. Immunother. 37:264-270 (1993).
Fong et al., "Dendritic cell-based xenoantigen vaccination for prostate cancer immunotherapy", J. Immunol. 167 (12):7150-6 (2001).
Goldenberg et al., "Monoclonal Antibodies in Cancer Detection and Therapy", Am. J. Med. 94(3):297-312 (1993).
Goldenberg et al., "New Developments in Monoclonal Antibodies for Cancer Detection and Therapy", CA Cancer J. Clin. 44(1):43-64 (1994).
Goverman et al., "Chimeric immunoglobulin-T cell receptor proteins form functional receptors: implications for T cell receptor complex formation and activation", Cell 60:929-939 (1993).
Gross et al., "Generation of effector T cells expressing chimeric T cell receptor with antibody type-specificity", Transp. Proc. 21(1):127-130 (Feb. 1989).
Gross et al., "Expression of immunoglobulin-T-cell receptor chimeric molecules as functional receptors with antibody-type specificity", Proc. Natl. Acad. Sci. USA 86:10024-10028 (Dec. 1989).
Hefta et al., "Expression of Carcinoembryonic Antigen and Its Predicted Immunoglobulin-like Domains in HeLa Cells for Epitope Analysis", Cancer Res. 52:5647-5655 (1992).
Herlyn et al., "Specific detection of anti-idiotypic immune responses in cancer patients treated with murine monoclonal antibody", J. Immunol. Methods 85:27-38 (1985).
Herlyn et al., "Anti-idiotype immunization of cancer patients: Modulation of the immune response", Proc. Natl. Acad. Sci. USA 84:8055-8059 (1987).
Ikeda et al., "Epitope mapping of the carcinoembryonic antigen with various related recombinant proteins expressed in chinese hamster ovary cells and 25 distinct monoclonal antibodies", Mol. Immunol. 29(2):229-240 (1992).
Ioannides et al., "T cell recognition of human tumors: implications for molecular immunotherapy of cancer", Clin. Immunol. Immunopath. 66:91-106 (Feb. 1993).
Irvine et al., "Comparison of CEA-Recombinant Vaccinia Virus, Purified CEA, and an Anti-Idiotype Antibody Bearing the Image of a CEA Epitope in the Treatment and Prevention of CEA-Expressing Tumors", Vaccine Res. 2(2):79-94 (1993).
Kennedy et al., "Antibody to Hepatitis B Virus Induced by Injecting Antibodies to the Idiotype", Science 223:930-931 (1984).
Kos et al., "Requirement for Natural Killer Cells in the Induction of Cytotoxic T Cells", J. Immunol. 155:578-584 (1995).
Kresina et al., "Antiidiotypic Antibody Vaccine in Murine Schistosomiasis mansoni Comprising the Internal Image of Antigen", J. Clin. Invest. 83:912-920 (1989).
Lanzavecchia et al., "The use of hybrid hybridomas to target human cytotoxic T lymphocytes", Eur. J. Immun. 17:105-111 (1987).
Losman et al., "Baboon anti-idiotype antibodies mimic a carcinoembryonic antigen epitope", Int. J. Cancer 46:310-314 (1990).
Losman et al., "Human response against NP-4, a mouse antibody to carcinoembryonic antigen: Human anti-idiotype antibodies mimic an epitope on the tumor antigen", Proc. Natl. Acad. Sci. USA 88:3421-3425 (Apr. 1991).
Losman et al., "Mimicry of a carcinoembryonic antigen epitope by a rat monoclonal anti-idiotype antibody", Int. J. Cancer 56:580-584 (1994).
Machy et al., "Endocytosis and recycling of MHC-encoded class II molecules by mouse B lymphocytes", J. Immunol. 145(5):1350-1355 (1990).
McNamara et al., "Monoclonal Idiotype Vaccine Against *Streptococcus pneumoniae* Infection", Science 226:1325-1326 (1984).
Mittelman et al., "Kinetics of the immune response and regression of metastatic lesions following development of humoral anti-high molecular weight-melanoma associated antigen immunity in three patients with advanced malignant melanoma immunized with mouse antiidiotypic monoclonal antibody MK2-23", Cancer Res. 54:415-421(1994).

(56) References Cited

OTHER PUBLICATIONS

Moldenhauer et al., "Surface-expressed invariant chain (CD74) is required for internalization of human leucocyte antigen-DR molecules to early endosomal compartments", Immunol. 96:473-484 (1999).
Monestier et al., "Syngeneic Anti-idotype Monoclonal Antibodies to Murine Anticarcinoembryonic Antigen Monoclonal Antibodies", Cancer Res. 49:123-126 (1989).
Morton et al., Delivery of Nascent MHC Class II-Invariant Chain Complexes to Lysosomal Compartments and Proteolysis of Invariant Chain by Cysteine Proteases Preceded Peptide Binding in B-Lymphoblastoid Cells, J. Immunol. 154:137-150 (1995).
Nepom et al., "Induction of immunity to a human tumor marker by in vivo administration of anti-idiotypic antibodies in mice", Proc. Natl. Acad. Sci. USA 81:2864-2867 (1984).
Nohria et al., "Cytokines as potential vaccine adjuvants", Biotherapy 7:261-269 (1994).
Pathak et al., "Endocytic Recycling is Required for the Presentation of an Exogenous Peptide via MHC Class II Molecules", Traffic 1:561-569 (2000).
Paul, W., (ed.), Fundamental Immunology, 3rd Ed., Raven Press, New York, 1993, p. 242.
Pawlak-Byczkowska et al. "Two New Monoclonal Antibodies, EPB-1 and EPB-2, Reactive with Human Lymphoma", Cancer Res. 49:4568-4577 (1989).
Powell et al., "Induction of effective immunity to moloney murine sarcoma virus using monoclonal anti-idiotypic antibody as immunogen", J. Immunol. 142(4):1318-1324 (1989).
Primus et al., "Immunological Heterogeneity of Carcinoembryonic Antigen: Antigenic Determinants on Carcinoembryonic Antigen Distinguished by Monoclonal Antibodies", Cancer Res. 43:686-692 (1983).
Pupa et al., "Activation of mononuclear cells to be used for hybrid monoclonal antibody-induced lysis of human ovarian carcinoma cells", Int. J. Cancer 42:455-459 (1988).
Renner et al., "Cure of xenografted human tumors by bispecific monoclonal antibodies and human T cells", Science 264:833-835 (1994).
Roche et al., "Cell surface HLA-DR-invariant chain complexes are targeted to endosomes by rapid internalization", Proc. Natl. Acad. Sci. USA 90:8581-8585 (1993).
Roitt et al., Immunology, 3rd Ed., Mosby, London, 1993, p. 6.9.
Rosenthal et al., "Human tumor vaccines and genetic engineering of tumors with cytokine and histocompatibility genes to enhance immunogenicity", Curr. Opin. Oncol. 6:611-615 (1994).
Shan et al., "Constitutive Endocytosis and Degradation of CD22 by Human B Cells", J. Immunol. 154:4466-4475 (1995).
Stein et al., "Neonatal administration of idiotype or antiidiotype primes for protection against *Escherichia coli* K13 infection in mice", J. Exp. Med. 160(4):1001-11 (1984).
Tedder et al., "Cloning of a complementary DNA encoding a new mouse B lymphocyte differentiation antigen, homologous to the human B1 (CD20) antigen, and localization of the gene to chromosome 19", J. Immunol. 141 (12):4388-94 (1988).
Traub et al., "Antiidiotype Antibodies in Cancer Patients Receiving Monoclonal Antibody to Carcinoembryonic Antigen", Cancer Res. 48:4002-4006 (1988).
Tsang et al., "A Recombinant CEA-Vaccinia Vaccine Induces a CEA-Specific Cytotoxic T-cell Response in Carcinoma Patients", Proc. Amer. Assoc. Cancer Res. vol. 36, p. 249, Abstract #1483 (1995).
Van Dijk et al., "Induction of tumor-cell lysis by bi-specific monoclonal antibodies recognizing renal-cell carcinoma and CD3 antigen", Int. J. Cancer 43:344-349 (1989).
Van Duk et al., "Bispecific antibodies reactive with the multidrug-resistance-related glycoprotein and CD3 induce lysis of multidrug-resistant tumor cells", Int. J. Cancer 44:738-743 (1989).
Van Kaer, L., "Accessory Proteins that Control the Assembly of MHC Molecules with Peptides", Immunologic Res. 23-2/3:205-214 (2001).
Waldmann et al., "Monoclonal Antibodies in Diagnosis and Therapy", Science 252:1657-1662 (1991).
Xu et al., "The Novelty of Antigen-Processing Compartments", J. Immunol. 155(4):1652-4 (1995).
Yu et al., "Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells", Int. J. Cancer 56:244-248 (1994).
Matsui et al., "Characterization of clonogenic multiple myeloma cells", Blood 103(6):2332-2336 (2004).
Kretz-Rommel et al., "In vivo targeting of antigens to human dendritic cells through DC-SIGN elicits stimulatory immune responses and inhibits tumor growth in grafted mouse models", J Immunother. Oct. 2007;30(7):715-26.
Titzer et al., "Vaccination of multiple myeloma patients with idiotype-pulsed dendritic cells: immunological and clinical aspects", Br J Haematol. Mar. 2000;108(4):805-16.

* cited by examiner

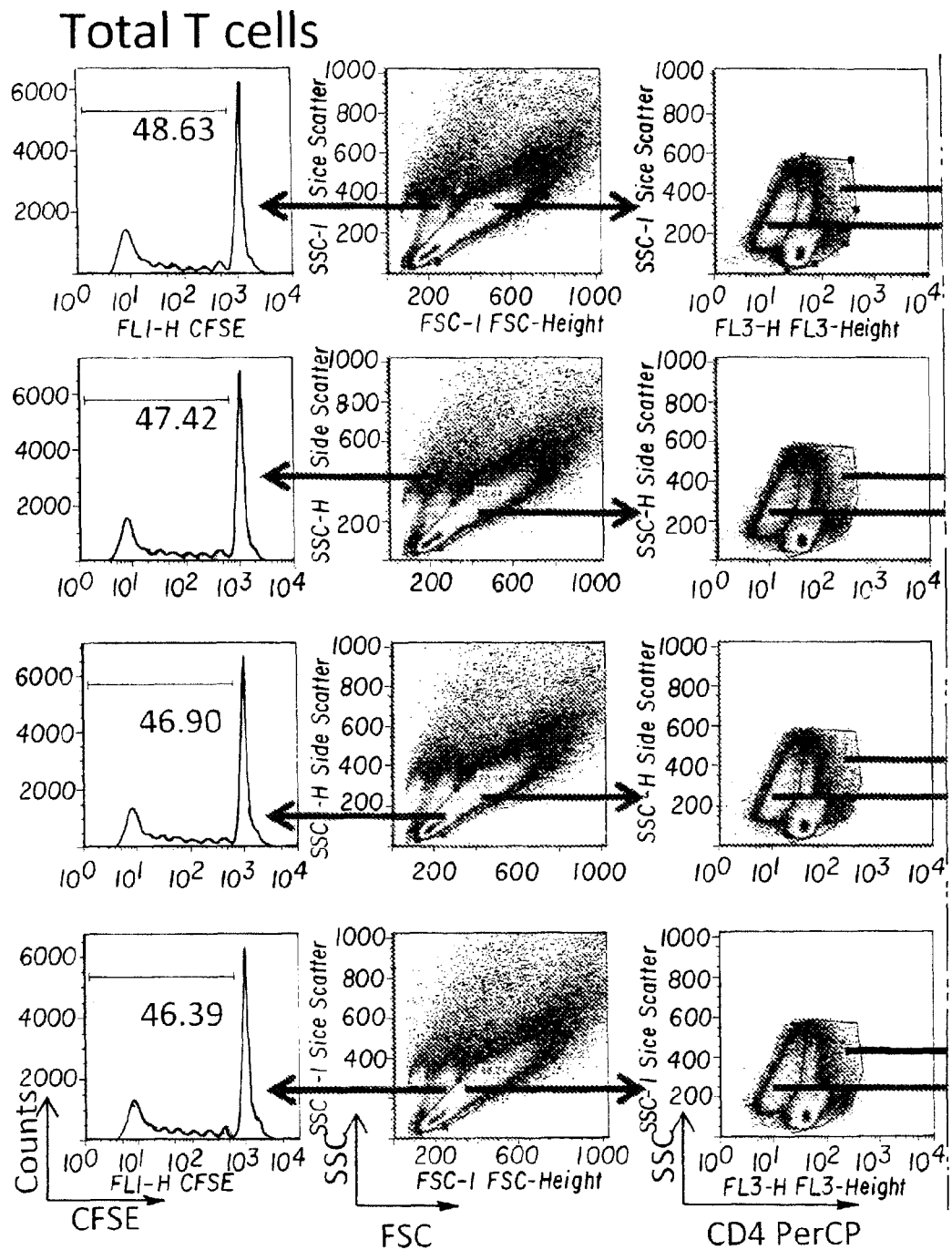
FIG. 6A1

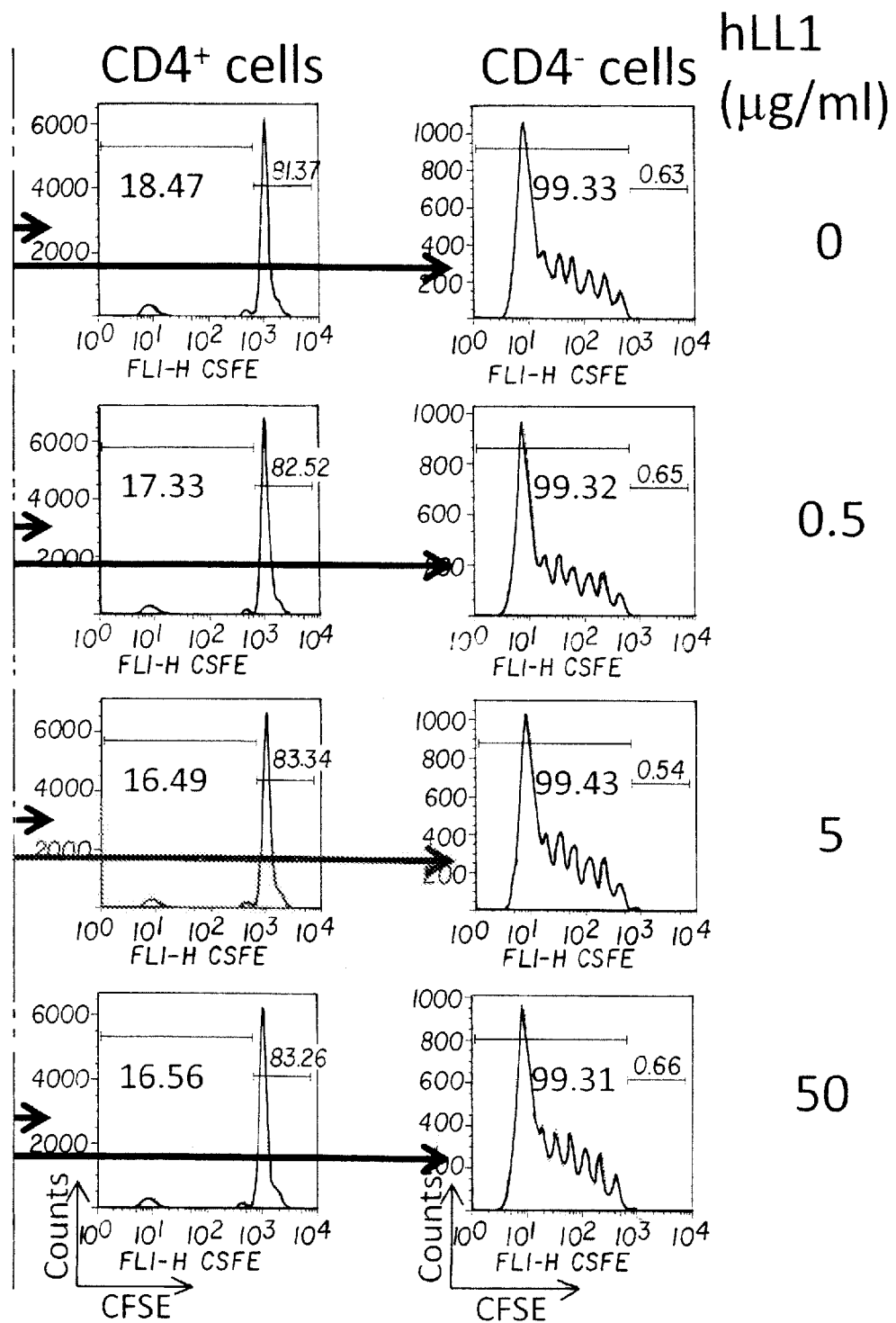
FIG. 6A2

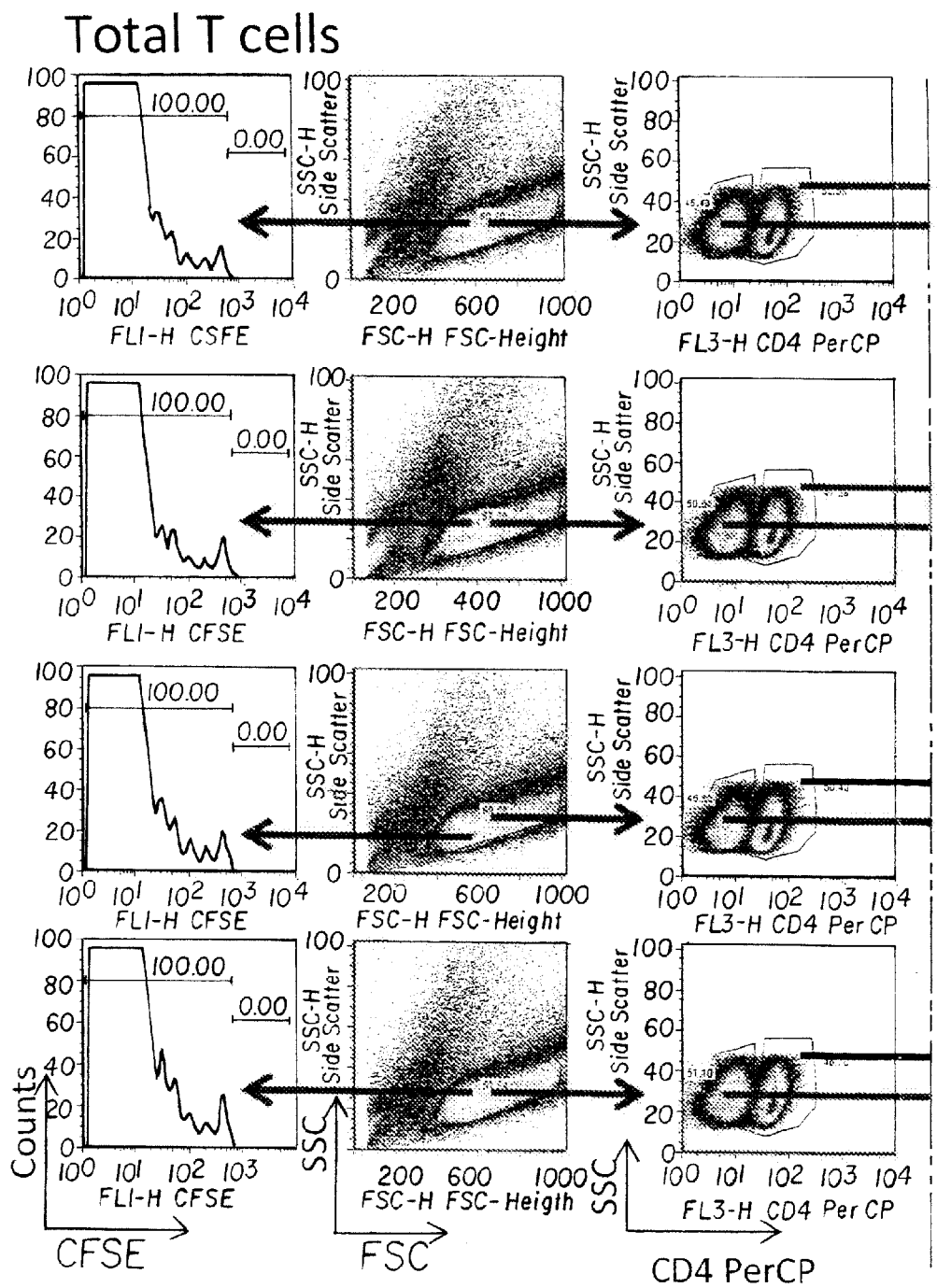
FIG. 6B1

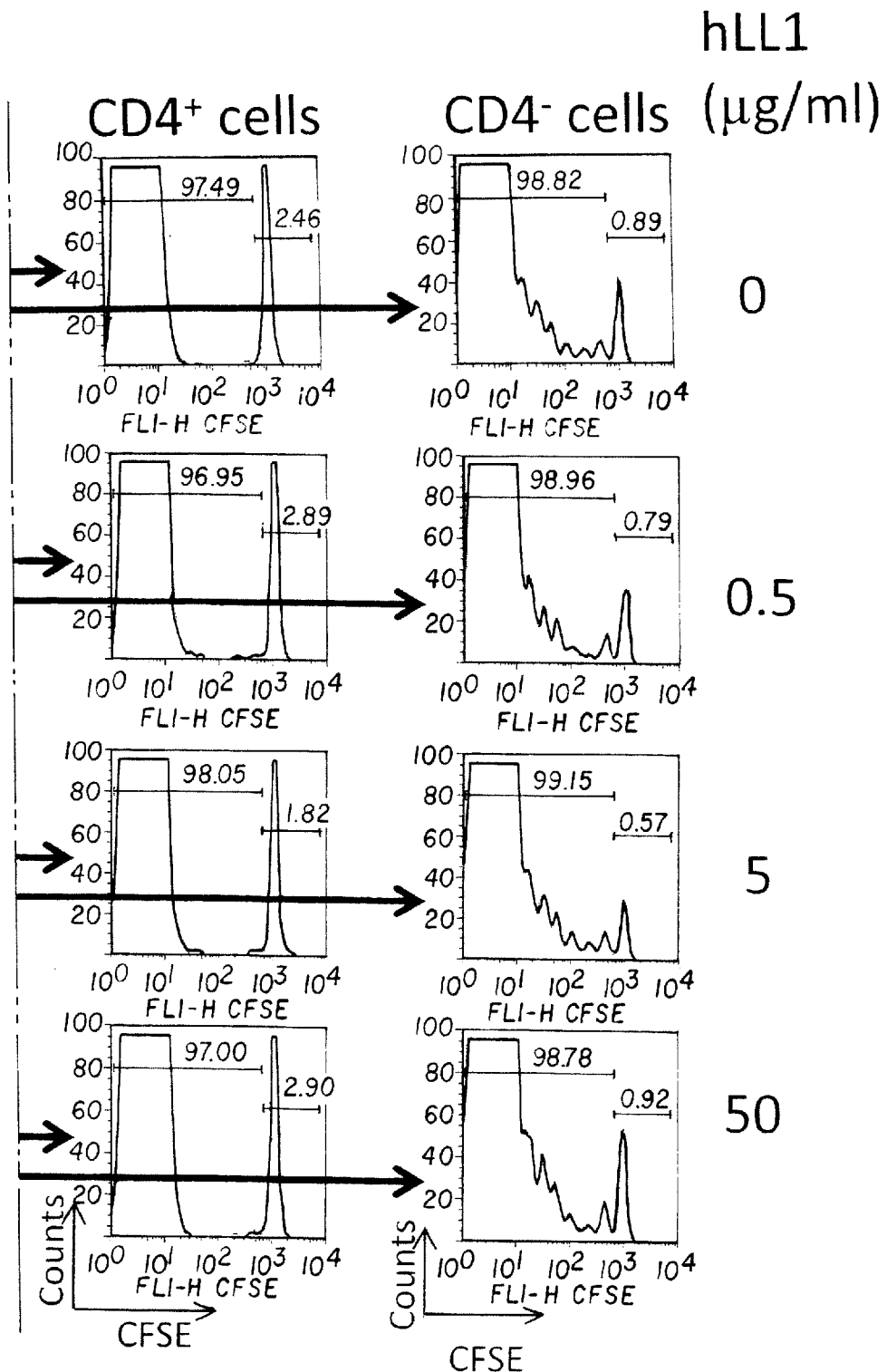
FIG. 6B2

```
                        SEQUENCE LISTING

<160> NUMBER OF SEQ ID NOS: 35

<210> SEQ ID NO 1
<211> LENGTH: 44
<212> TYPE: PRT
<213> ORGANISM: Homo sapiens

<400> SEQUENCE: 1

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ile Glu Tyr Leu Ala Lys Gln Ile Val Asp Asn Ala Ile Gln Gln
1               5                   10                  15

Ala

<210> SEQ ID NO 4
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 4

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 5
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: Any conservative amino acid substitution
<220> FEATURE:
<221> NAME/KEY: MOD_RES
<222> LOCATION: (4)..(4)
<223> OTHER INFORMATION: Any conservative amino acid substitution
<220> FEATURE:
<221> NAME/KEY: MOD_RES
<222> LOCATION: (6)..(8)
<223> OTHER INFORMATION: Any conservative amino acid substitution
<220> FEATURE:
<221> NAME/KEY: MOD_RES
<222> LOCATION: (10)..(11)
<223> OTHER INFORMATION: Any conservative amino acid substitution
<220> FEATURE:
<221> NAME/KEY: MOD_RES
<222> LOCATION: (14)..(15)
<223> OTHER INFORMATION: Any conservative amino acid substitution
<220> FEATURE:
<221> NAME/KEY: MOD_RES
<222> LOCATION: (17)..(17)
<223> OTHER INFORMATION: Any conservative amino acid substitution
<220> FEATURE:
<221> NAME/KEY: MOD_RES
<222> LOCATION: (19)..(19)
<223> OTHER INFORMATION: Any conservative amino acid substitution
<220> FEATURE:
<221> NAME/KEY: MOD_RES
<222> LOCATION: (22)..(27)
<223> OTHER INFORMATION: Any conservative amino acid substitution
<220> FEATURE:
<221> NAME/KEY: MOD_RES
<222> LOCATION: (30)..(30)
<223> OTHER INFORMATION: Any conservative amino acid substitution
<220> FEATURE:
<221> NAME/KEY: MOD_RES
<222> LOCATION: (32)..(32)
<223> OTHER INFORMATION: Any conservative amino acid substitution
<220> FEATURE:
<221> NAME/KEY: MOD_RES
<222> LOCATION: (34)..(34)
<223> OTHER INFORMATION: Any conservative amino acid substitution
<220> FEATURE:
<221> NAME/KEY: MOD_RES
<222> LOCATION: (37)..(38)
<223> OTHER INFORMATION: Any conservative amino acid substitution
<220> FEATURE:
<221> NAME/KEY: MOD_RES
<222> LOCATION: (40)..(44)
<223> OTHER INFORMATION: Any conservative amino acid substitution
<220> FEATURE:
<223> OTHER INFORMATION: see specification as filed for detailed
      description of substitutions and preferred embodiments

<400> SEQUENCE: 5

Xaa Xaa Ile Xaa Ile Xaa Xaa Xaa Leu Xaa Xaa Leu Leu Xaa Xaa Tyr
```

```
                1               5                  10                  15
Xaa Val Xaa Val Leu Xaa Xaa Xaa Xaa Xaa Xaa Leu Val Xaa Phe Xaa
                        20                  25                  30

Val Xaa Tyr Phe Xaa Xaa Leu Xaa Xaa Xaa Xaa Xaa
                35                  40

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any conservative amino acid substitution
<220> FEATURE:
<221> NAME/KEY: MOD_RES
<222> LOCATION: (7)..(8)
<223> OTHER INFORMATION: Any conservative amino acid substitution
<220> FEATURE:
<221> NAME/KEY: MOD_RES
<222> LOCATION: (11)..(12)
<223> OTHER INFORMATION: Any conservative amino acid substitution
<220> FEATURE:
<221> NAME/KEY: MOD_RES
<222> LOCATION: (15)..(17)
<223> OTHER INFORMATION: Any conservative amino acid substitution
<220> FEATURE:
<223> OTHER INFORMATION: see specification as filed for detailed
      description of substitutions and preferred embodiments

<400> SEQUENCE: 6

Xaa Xaa Xaa Xaa Xaa Ala Xaa Xaa Ile Val Xaa Xaa Ala Ile Xaa Xaa
1               5                   10                  15

Xaa

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Ile Glu Tyr Val Ala Lys Gln Ile Val Asp Tyr Ala Ile His Gln
1               5                   10                  15

Ala

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Ile Glu Tyr Lys Ala Lys Gln Ile Val Asp His Ala Ile His Gln
1               5                   10                  15

Ala

<210> SEQ ID NO 9
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 9

Gln Ile Glu Tyr His Ala Lys Gln Ile Val Asp His Ala Ile His Gln
1               5                   10                  15

Ala

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ile Glu Tyr Val Ala Lys Gln Ile Val Asp His Ala Ile His Gln
1               5                   10                  15

Ala

<210> SEQ ID NO 11
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Leu Ile Glu Glu Ala Ala Ser Arg Ile Val Asp Ala Val Ile Glu
1               5                   10                  15

Gln Val Lys Ala Ala Gly Ala Tyr
                20

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Glu Gln Tyr Ala Asn Gln Leu Ala Asp Gln Ile Ile Lys Glu Ala
1               5                   10                  15

Thr Glu

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Phe Glu Glu Leu Ala Trp Lys Ile Ala Lys Met Ile Trp Ser Asp Val
1               5                   10                  15

Phe Gln Gln Cys
                20

<210> SEQ ID NO 14
<211> LENGTH: 25
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 15
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 17
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any conservative amino acid substitution
<220> FEATURE:
<221> NAME/KEY: MOD_RES
<222> LOCATION: (4)..(4)
<223> OTHER INFORMATION: Any conservative amino acid substitution
<220> FEATURE:
<221> NAME/KEY: MOD_RES
<222> LOCATION: (7)..(7)
<223> OTHER INFORMATION: Any conservative amino acid substitution
<220> FEATURE:
<221> NAME/KEY: MOD_RES
<222> LOCATION: (10)..(10)
<223> OTHER INFORMATION: Any conservative amino acid substitution
<220> FEATURE:
<221> NAME/KEY: MOD_RES
<222> LOCATION: (18)..(18)
<223> OTHER INFORMATION: Any conservative amino acid substitution
<220> FEATURE:
<221> NAME/KEY: MOD_RES
<222> LOCATION: (23)..(23)
<223> OTHER INFORMATION: Any conservative amino acid substitution
```

```
<220> FEATURE:
<221> NAME/KEY: MOD_RES
<222> LOCATION: (26)..(26)
<223> OTHER INFORMATION: Any conservative amino acid substitution
<220> FEATURE:
<221> NAME/KEY: MOD_RES
<222> LOCATION: (33)..(34)
<223> OTHER INFORMATION: Any conservative amino acid substitution
<220> FEATURE:
<221> NAME/KEY: MOD_RES
<222> LOCATION: (37)..(38)
<223> OTHER INFORMATION: Any conservative amino acid substitution
<220> FEATURE:
<221> NAME/KEY: MOD_RES
<222> LOCATION: (40)..(40)
<223> OTHER INFORMATION: Any conservative amino acid substitution
<220> FEATURE:
<221> NAME/KEY: MOD_RES
<222> LOCATION: (42)..(42)
<223> OTHER INFORMATION: Any conservative amino acid substitution
<220> FEATURE:
<221> NAME/KEY: MOD_RES
<222> LOCATION: (44)..(44)
<223> OTHER INFORMATION: Any conservative amino acid substitution
<220> FEATURE:
<223> OTHER INFORMATION: see specification as filed for detailed
      description of substitutions and preferred embodiments

<400> SEQUENCE: 17

Xaa His Ile Xaa Ile Pro Xaa Gly Leu Xaa Glu Leu Leu Gln Gly Tyr
1               5                   10                  15

Thr Xaa Glu Val Leu Arg Xaa Gln Pro Xaa Asp Leu Val Glu Phe Ala
            20                  25                  30

Xaa Xaa Tyr Phe Xaa Xaa Leu Xaa Glu Xaa Arg Xaa
        35                  40

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Lys Ser Leu Ser Leu Ser Pro Gly Leu Gly Ser Gly Gly Gly Gly
1               5                   10                  15

Ser Gly Gly Cys Gly
            20

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Lys Ser Leu Ser Leu Ser Pro Gly Ala Gly Ser Gly Gly Gly Gly
1               5                   10                  15

Ser Gly Gly Cys Gly
            20

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
```

```
peptide

<400> SEQUENCE: 20

Gln Lys Ser Leu Ser Leu Ser Pro Gly Gly Ser Gly Gly Gly Gly Ser
1               5                   10                  15

Gly Gly Cys Gly
            20

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Lys Ser Cys
1

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Gly Gly Ser Gly Gly Gly Gly Ser
1               5                   10

<210> SEQ ID NO 23
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gly Ser Gly Gly Gly Gly Ser Gly Gly Gly Gly Ser His Ile Gln Ile
1               5                   10                  15

Pro Pro Gly Leu Thr Glu Leu Leu Gln Gly Tyr Thr Val Glu Val Leu
            20                  25                  30

Arg Gln Gln Pro Pro Asp Leu Val Glu Phe Ala Val Glu Tyr Phe Thr
        35                  40                  45

Arg Leu Arg Glu Ala Arg Ala
    50                  55

<210> SEQ ID NO 24
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Ser Gly Gly Gly Gly Ser Gly Gly Gly Gly Ser Gln Ile Glu Tyr
1               5                   10                  15

Leu Ala Lys Gln Ile Val Asp Asn Ala Ile Gln Gln Ala
            20                  25

<210> SEQ ID NO 25
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Gly Gly Ser Gly Gly Gly Cys Gly
1               5                   10

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agatctggcg cacctgaact cctg                                              24

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaattcggat cctttacccg gagacaggga gag                                    33

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 28

His His His His His His
1               5

<210> SEQ ID NO 29
<211> LENGTH: 43
<212> TYPE: PRT
<213> ORGANISM: Mus musculus

<400> SEQUENCE: 29

Thr Leu Ser His Phe Leu Lys Met Arg Arg Leu Glu Leu Ile Gln Thr
1               5                   10                  15

Ser Lys Pro Tyr Val Asp Ile Tyr Asp Cys Glu Pro Ser Asn Ser Ser
            20                  25                  30

Glu Lys Asn Ser Pro Ser Thr Gln Tyr Cys Asn
        35                  40

<210> SEQ ID NO 30
<211> LENGTH: 291
<212> TYPE: PRT
<213> ORGANISM: Mus musculus

<400> SEQUENCE: 30

Met Ser Gly Pro Phe Pro Ala Glu Pro Thr Lys Gly Pro Leu Ala Met
1               5                   10                  15
```

Gln Pro Ala Pro Lys Val Asn Leu Lys Arg Thr Ser Ser Leu Val Gly
            20                  25                  30

Pro Thr Gln Ser Phe Phe Met Arg Glu Ser Lys Ala Leu Gly Ala Val
        35                  40                  45

Gln Ile Met Asn Gly Leu Phe His Ile Thr Leu Gly Gly Leu Leu Met
50                  55                  60

Ile Pro Thr Gly Val Phe Ala Pro Ile Cys Leu Ser Val Trp Tyr Pro
65                  70                  75                  80

Leu Trp Gly Gly Ile Met Tyr Ile Ile Ser Gly Ser Leu Leu Ala Ala
                85                  90                  95

Ala Ala Glu Lys Thr Ser Arg Lys Ser Leu Val Lys Ala Lys Val Ile
            100                 105                 110

Met Ser Ser Leu Ser Leu Phe Ala Ala Ile Ser Gly Ile Ile Leu Ser
        115                 120                 125

Ile Met Asp Ile Leu Asn Met Thr Leu Ser His Phe Leu Lys Met Arg
130                 135                 140

Arg Leu Glu Leu Ile Gln Thr Ser Lys Pro Tyr Val Asp Ile Tyr Asp
145                 150                 155                 160

Cys Glu Pro Ser Asn Ser Ser Glu Lys Asn Ser Pro Ser Thr Gln Tyr
                165                 170                 175

Cys Asn Ser Ile Gln Ser Val Phe Leu Gly Ile Leu Ser Ala Met Leu
            180                 185                 190

Ile Ser Ala Phe Phe Gln Lys Leu Val Thr Ala Gly Ile Val Glu Asn
        195                 200                 205

Glu Trp Lys Arg Met Cys Thr Arg Ser Lys Ser Asn Val Val Leu Leu
210                 215                 220

Ser Ala Gly Glu Lys Asn Glu Gln Thr Ile Lys Met Lys Glu Glu Ile
225                 230                 235                 240

Ile Glu Leu Ser Gly Val Ser Ser Gln Pro Lys Asn Glu Glu Glu Ile
                245                 250                 255

Glu Ile Ile Pro Val Gln Glu Glu Glu Glu Ala Glu Ile Asn
            260                 265                 270

Phe Pro Ala Pro Pro Gln Glu Gln Glu Ser Leu Pro Val Glu Asn Glu
        275                 280                 285

Ile Ala Pro
    290

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggatccacac tttctcattt tttaaaaatg                                    30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctcgaggtta cagtactgtg tagatgggga                                    30

```
<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
agatctacac tttctcattt tttaaaaatg                                    30

<210> SEQ ID NO 34
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cggccgtcag tggtggtggt ggtggtggtt acagtactgt gtagatgg                48

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Ile Ile Asn Phe Glu Lys Leu
1               5
```

STRATEGIES FOR IMPROVED CANCER VACCINES

CROSS REFERENCE TO RELATED APPLICATIONS

This application is a continuation-in-part of U.S. patent application Ser. No. 12/544,476 (now issued U.S. Pat. No. 7,901,680), filed Aug. 20, 2009, which claimed the benefit under 35 U.S.C. 119(e) of Provisional U.S. Patent Application Ser. No. 61/090,487, filed Aug. 20, 2008, and which was a continuation-in-part of U.S. patent application Ser. No. 12/396,605 (now issued U.S. Pat. No. 7,858,070), filed Mar. 3, 2009, which was a divisional of U.S. Pat. No. 7,527,787, which was a continuation-in-part of U.S. Pat. Nos. 7,550,143; 7,521,056; and 7,534,866; which claimed the benefit under 35 U.S.C. 119(e) of provisional U.S. Patent Application Nos. 60/782,332, filed Mar. 14, 2006; 60/728,292, filed Oct. 19, 2005; 60/751,196, filed Dec. 16, 2005; and No. 60/864,530, filed Nov. 6, 2006. This application claims the benefit under 35 U.S.C. 119(e) of Provisional U.S. Patent Application Ser. No. 61/168,290, filed Apr. 10, 2009, incorporated herein by reference in its entirety.

SEQUENCE LISTING

The instant application contains a Sequence Listing which has been submitted via EFS-Web and is hereby incorporated by reference in its entirety. Said ASCII copy, created on Apr. 5, 2010, is named IMM319US.txt, and is 17,283 bytes in size.

BACKGROUND OF THE INVENTION

1. Field of the Invention

The present invention relates to compositions and methods for improved vaccines. In particular embodiments, the compositions and methods relate to xenoantigens, chemically modified antigens, antigens in conjunction with Th epitopes, dendritic cells loaded with antigens, immunoconjugates or fusion proteins comprising dendritic cell targeting antibodies attached to antigens and/or dendritic cell targeting lentiviral vectors expressing antigens. The vaccines are of use for therapy of a wide variety of diseases, including but not limited to cancer, autoimmune disease, immune dysfunction disease, metabolic disease, neurological diseases such as Alzheimer's and cardiovascular disease.

2. Related Art

Therapeutic vaccination against cancer is an important modality complementing current standard therapies, and may lead to long-term control of cancer. Numerous strategies are in development in an attempt to achieve better effectiveness, but except for the recent advent of vaccines against HPV, the long effort to produce a cancer vaccine has not succeeded.

Two major categories of tumor-related proteins can be exploited as potential antigens for cancer vaccines: tumor-specific antigens (TSAs) (Srivastava and Old, Immunol Today 9:78-83, 1988; Melief et al., Cold Spring Harbor Symp Quant. Biol 65:597-803, 1989; Hislop et al., Annu Rev Immunol. 25:587-617, 22007) and tumor-associated antigens (TAAs) (Dalgleish and Pandha, Adv Cancer Res 96:175-90, 2007; Finn, NEJM 358:2704-15, 2008). TSAs are molecules unique to cancer cells, such as the products of mutated normal cellular genes, viral antigens expressed on tumor cells, endogenous human retrovirus activated and expressed in cancer cells (Takahashi et al., J Clin Invest 118:1099-1109, 2008), and a recently identified placenta-specific antigen that is not found in any adult normal somatic tissue but highly expressed in a variety of tumor types, particularly in breast cancer (Chen et al., Beijing Da Xue Xue Bao 38:124-27, 2006; Koslowski et al., Cancer Res 67:9528-34, 2007; Old, Cancer Immunity 7:19, 2007). TAAs are molecules shared, but differently expressed, by cancer cells and normal cells.

Although TSAs are the ideal targets for immunotherapy and vaccination, the fact that they are expressed only on individual patients' cancer cells or small subsets of tumors would require the development of personalized therapy for individual patients, thus limiting their wide application (Baxevanis et al., Cancer Immunol Immunother 58:317024, 2009). As for TAAs, which are largely self-antigens (self-Ags) already tolerized by the immune system through a tightly controlled process of negative selection in the thymus (Kruisbeek and Amsen, Curr Opin Immunol 8:233-44, 1996; Stockinger, Adv Immunol 71:229-65, 1999) or peripheral tolerization, the major challenge is to induce a strong immune response directed selectively against cancer cells.

A need exists in the field for new approaches to vaccines of use for cancer treatment and/or prevention, capable of inducing a strong immune response against cancer cells and of wide application.

SUMMARY OF THE INVENTION

The present invention concerns novel approaches to the development of effective cancer vaccines, including but not limited to optimized antigen design, in vivo targeted dendritic cell vaccination, and cancer vaccines used in combination with chemotherapy, monoclonal antibodies, adoptive T-cell transfer, or stem cell transplantation. The rationale and development of each of these approaches for improved cancer vaccines is described below.

DETAILED DESCRIPTION OF THE INVENTION

Definitions

Figure 1:
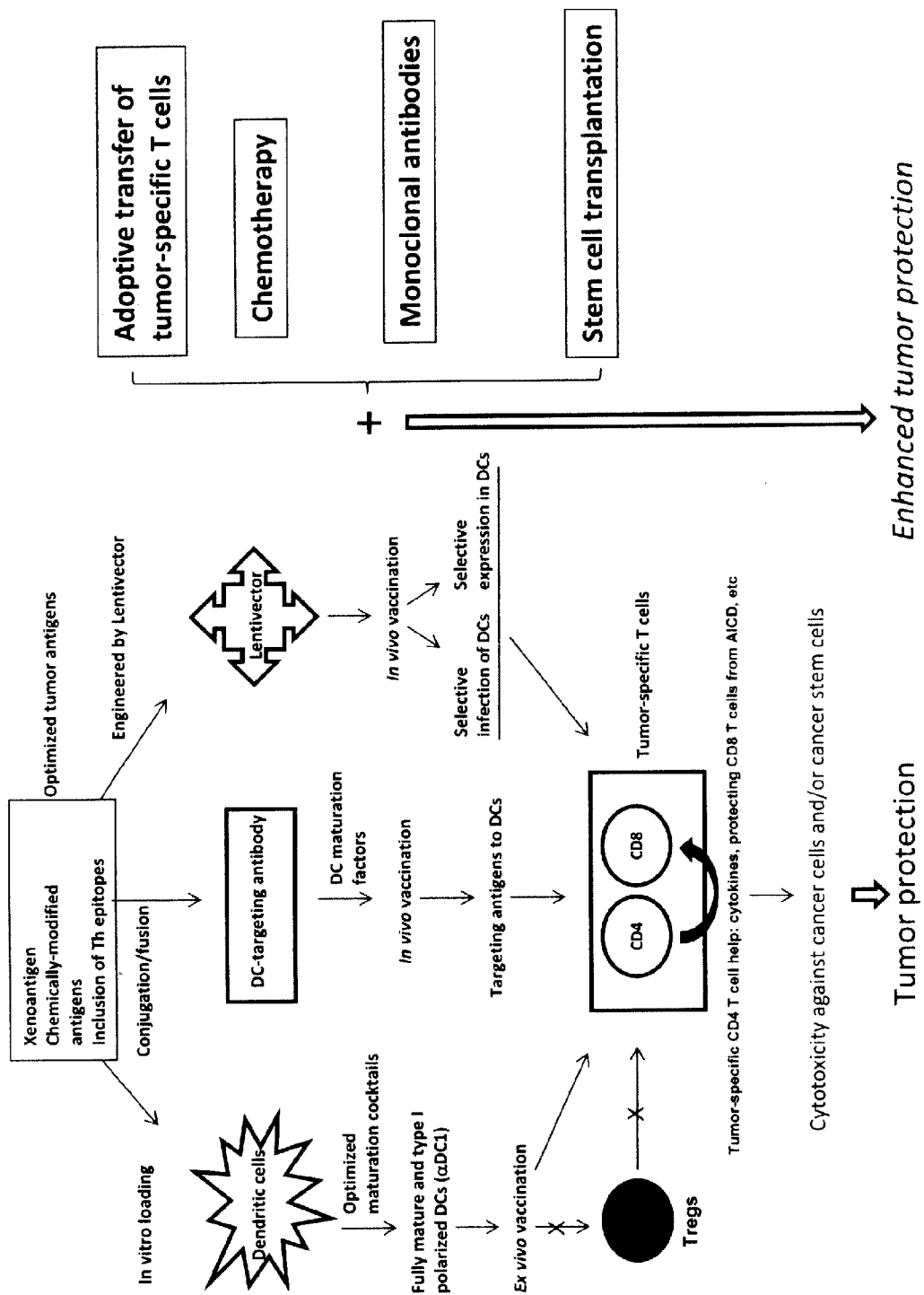
FIG. 1. Diagram of several novel strategies/approaches in cancer vaccination. To overcome immune tolerance, antigens to be used for cancer vaccines are optimized which includes: (1) using xenoantigen other than TAA/self antigen, (2) chemically-modified TAA, (3) inclusion of antigen-specific CD4 Th epitopes. The optimized antigen is loaded to dendritic cells followed by optimized maturation (αDC1) for ex vivo DC vaccination. The antigen can also be linked to a DC-targeting antibody via genetic fusion or chemical conjugation. In vivo administration of the conjugate or fusion protein specifically delivers the antigen to DCs and initiates immune responses. The optimized antigen can also be engineered with a lentivector which is pseudotyped with an envelope protein that can specifically recognize DCs (for example, a DC-SIGN antibody). In vivo administration of this recombinant lentiviral vector selectively infects DCs. The antigen can also be encoded by a lentiviral vector which carries a lineage-specific internal promoter (e.g., dectin-2 gene promoter) that restricts the transgene (antigen) expression to antigen-presenting cells. All of the vaccination approaches initiate antigen-specific (both CD4+ and CD8+) T cell responses against cancer cells and/or cancer stem cells. The tumor-specific CD4+ T cells provides help and survival signals to tumor-specific CD8+ T cells and maintain CD8+ T-cell memory, which are essential for long-lasting anti-tumor immunity. The tumor protection efficacy can be augmented by combinational use of adoptive transfer of antigen-specific T cells, chemotherapy, monoclonal antibodies, and/or stem cell transplantation. Arrows with X represent inhibitory action, or negative effect.

As used herein, the terms "a", "an" and "the" may refer to either the singular or plural, unless the context otherwise makes clear that only the singular is meant.

As used herein, the term "about" means plus or minus ten percent (10%) of a value. For example, "about 100" would refer to any number between 90 and 110.

An antibody refers to a full-length (i.e., naturally occurring or formed by normal immunoglobulin gene fragment recombinatorial processes) immunoglobulin molecule (e.g., an IgG antibody) or an immunologically active, antigen-binding portion of an immunoglobulin molecule, like an antibody fragment. In various embodiments, antibodies may be murine, chimeric, humanized or human, polyclonal or monoclonal, monospecific, bispecific or multispecific.

An antibody fragment is a portion of an antibody such as $F(ab')_2$, $F(ab)_2$, Fab', Fab, Fv, scFv and the like. Regardless of structure, an antibody fragment binds with the same antigen that is recognized by the intact antibody. For example, an anti-HLA-DR antibody fragment binds to HLA-DR The term "antibody fragment" also includes isolated fragments consisting of the variable regions, such as the "Fv" fragments consisting of the variable regions of the heavy and light chains and recombinant single chain polypeptide molecules in which light and heavy variable regions are connected by a peptide linker ("scFv proteins"). As used herein, the term "antibody fragment" does not include portions of antibodies without antigen binding activity, such as Fc fragments or single amino acid residues.

A naked antibody or naked antibody fragment refers to an antibody or antigen binding fragment thereof which is not conjugated to a therapeutic agent. Naked antibodies may include murine monoclonal antibodies, as well as recombinant antibodies, such as chimeric, humanized or human antibodies.

A therapeutic agent is a molecule, atom or complex which is administered separately, concurrently or sequentially with an antibody moiety or conjugated to an antibody moiety, i.e., antibody or antibody fragment, and is useful in the treatment of a disease. Non-limiting examples of therapeutic agents include antibodies, antibody fragments, drugs, toxins, nucleases, hormones, immunomodulators, chelators, boron compounds, photoactive agents, oligonucleotides (e.g. antisense oligonucleotides or siRNA) and radioisotopes.

An immunoconjugate is a conjugate of an antibody component with at least one therapeutic or diagnostic agent. An antibody component may be conjugated with multiple therapeutic and/or diagnostic agents to form an immunoconjugate.

The term antibody fusion protein may refer to a recombinantly produced antigen-binding molecule in which one or more of the same or different single-chain antibody or antibody fragment segments with the same or different specificities are linked. Valency of the fusion protein indicates how many binding arms or sites the fusion protein has to a single antigen or epitope; i.e., monovalent, bivalent, trivalent or multivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only bind with one epitope. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators and toxins. One preferred toxin comprises a ribonuclease (RNase), preferably a recombinant RNase. However, the term is not limiting and a variety of protein or peptide effectors may be incorporated into a fusion protein. In another non-limiting example, a fusion protein may comprise an AD or DDD sequence for producing a dock-and-lock (DNL) construct as discussed below.

Vaccination with Xenoantigens to Break Tolerance

Novel approaches to anti-cancer vaccine development are summarized in FIG. 1. The discovery in 1996 that a single T-cell receptor can productively recognize a large continuum of related ligands (Kersh and Allen, 1996, *J. Exp. Med.* 184: 1259-1268; Boesteanu et al., 1998, *J. Immunol.* 161:4719-4727) has raised the possibility that T cells recognizing a xenoantigen may cross-react with its self-homologous counterpart. In the case of TAA, the autologous T cells specific to TAAs may have largely been deleted, but T cells specific to the xenoantigenic counterparts of TAAs may survive the negative selection. These naïve, negative selection-survived, and xenoantigen-specific, T cells, once induced and activated by immunization with a xenoantigen, may cross-react with their cognate TAA, due to the plasticity of TCR recognition. It is therefore an approach to overcome the immune tolerance against homologous self-Ags by immunization with the xenoantigens.

This concept has been verified by the accumulated evidence that immunization with xenoantigens is effective in the induction of both cellular and humoral immune responses against their self counterparts. In a phase I clinical trial, eleven of 21 prostate cancer patients immunized with dendritic cells pulsed with recombinant mouse prostatic acid phosphatase developed type-1 T-cell proliferative responses to the homologous self-Ags, and 6 patients had clinical stabilization of their previously progressing prostate cancer (Fong et al., 2001, *J. Immunol.* 167:7150-7156). In a mouse model of B-cell lymphoma, immunization with xenogeneic human CD20 DNA or its extracellular domain elicits both T-cell and antibody responses against cells expressing mouse CD20 (Roberts et al., 2002, *Blood* 99:3748-3755; Palomba et al., 2005, *Clin. Cancer Res.* 11:370-379). Long-term survival was observed in 10-30% mice immunized with human CD20 extracellular domain DNA, and tumor rejection was shown to require $CD8^+$ T cells during the effector phase (Palomba et al., 2005, *Clin. Cancer Res.* 11:370-379).

In another study, C57BL/6 mice, which are tolerant to gp75/tyrosinase-related protein-1 (TRP-1), generated autoantibodies against gp75 after immunization with DNA encoding human gp75 but not syngeneic mouse gp75, resulting in significant tumor protection and the rejection of tumor challenge requiring $CD4^+$ and $NK1.1^+$ cells and Fc receptor gamma-chain (Weber et al., 1998, *J. Clin. Invest.* 102:1258-1264). In the B16F10LM3 mouse model of melanoma, xenogeneic DNA immunization with human TRP-2 was effective in protecting mice from intradermal tumor challenge by a mechanism requiring $CD4^+$ and $CD8^+$ T cells. Although this immunization strategy failed to inhibit the growth of established tumors, it prevented local recurrence and the development of metastases in the mouse model of minimal residual disease of melanoma (Hawkins et al., 2002, *J. Surg. Res.* 102(2):137-143). Lu et al. reported that a DNA vaccine encoding the extracellular domain of xenogeneic (human) EGFR effectively elicited both protective and therapeutic antitumor immunity against mouse $EGFR^+$ lung cancer, indicating the autoimmune response against $EGFR^+$ cancer could be induced in a cross-reaction between the xenogeneic homologous and self-EGFR (Lu et al., 2003, *J. Immunol.* 170:3162-3170).

In another mouse tumor model, mammary carcinoma in HER-2/neu transgenic mice was effectively inhibited by xenogeneic DNA vaccination (Pupa et al., 2005, *Cancer Res.* 65:1071-1078; Gallo et al., 2005, *Int. J. Cancer* 113:67-77). More recently, Ko et al. (2007, *Cancer Res.* 67:7477-7486) reported that self-tolerance in the same mouse tumor model could be efficiently broken by immunization with DNA plasmid and/or adenoviral vector expressing the extracellular and transmembrane domain of xenogenic human Her-2/neu in combination with gemcitabine therapy. Furthermore, vaccination of HLA-A*0201 transgenic (HHD) mice with human Her-2($9_{435}$), the xenogeneic altered peptide ligand of its mouse homologue, significantly increased the frequency of murine Her-2($9_{435}$)-specific CTL, and also induced strong protective and therapeutic immunity against the transplantable ALC tumor cell line transfected to coexpress HLA-A*0201 and hHer-2/neu or rHer-2/neu (Gritzapis et al., 2006, *Cancer Res.* 66(10):5452-5460).

Of note, it was reported that the elevated frequencies of self-reactive $CD8^+$ T cells following xeno-immunization are due to the presence of a heteroclitic $CD4^+$ T-cell helper epitope in the xenoantigen (Kianizad et al., 2007, *Cancer Res.* 67:6459-6467). In that study, both mDCT (self-antigen) and hDCT (xenoantigen) efficiently elicited specific CD8+ and $CD4^+$ T cells in DCT-deficient mice, whereas in wild-type mice, only hDCT elicited a significant level of specific $CD8^+$ and $CD4^+$ T cells. After introduction of an hDCT-derived dominant $CD4^+$ T-cell epitope into mDCT, the mutated mDCT, unlike the native mDCT, elicited potent $CD8^+$ T-cell frequencies and protective immunity that were comparable to that with hDCT. These results suggest a mechanism of action of xenoimmunization by which xenoantigens can provide heteroclitic $CD4^+$ helper T-cell epitopes to augment $CD8^+$ T-cell immunity against conserved $CD8^+$ T-cell epitopes (Kianizad et al., 2007, *Cancer Res.* 67:6459-6467). Taken together, these studies demonstrate that immunization with xenoantigens is an effective approach to break immune tolerance of cancer.

Vaccination with Chemically-Modified or Mutated Epitopes

Another approach to break immune tolerance to self-Ags is achieved with chemical modification of antigens (FIG. 1). As early as in 1965, Weigle reported that rabbits immunized with a diazonium derivative-labeled rabbit thyroglobulin produced cross-reactive antibodies to native thyroglobulin, possibly due to the chemical modification of antigen that results in immunogenic epitopes for the cross-reactive antibody responses (Weigle, 1965, *J. Exp. Med.* 121:289-308). Recently, Grunewald et al. reported that self-tolerance can be overcome by site-specific incorporation of an immunogenic unnatural amino acid into a protein of interest to produce high-titer antibodies that cross-react with the wild-type protein (Grunewald et al., 2008, *Proc. Natl. Acad. Sci. U.S.A.* 105:11276-80). Specifically, mutation of a single tyrosine residue (Tyr86) of mTNF-α to p-nitrophenylalanine (pNO2Phe) induced a high-titer antibody response that was highly cross-reactive with native mTNF-α and protected mice against lipopolysaccharide (LPS)-induced death. This strategy may be applied to the modification and creation of T-cell epitopes.

Other approaches, such as anchor modification of the non-canonical tumor-associated mucin 1-8 peptide, resulted in enhanced major histocompatibility complex class I binding and immune responses (Lazoura et al., 2006, *Immunology* 119:306-316). The continuously revealed bio-information on the complex of MHC/epitope/TCR and computer modeling of their structures could provide more clues in designing altered ligands/epitopes for induction of efficient immunity against self-antigens.

Vaccination with Antigens to Induce Tumor-Specific T-Helper Response

Antigen-specific T-helper (Th) cells play a key role in priming, maintaining, and boosting CTL responses (Kennedy, 2008, *Immunol. Rev.* 222:129-144). These Th cells, upon activation at the tumor site by antigen-processing cells (APCs) expressing tumor antigens, provide local or direct growth and survival signals to the tumor-specific CTLs. Strikingly, addition of a tumor-specific Th epitope to a CTL peptide vaccine (OVA257-263, SIINFEKL (SEQ ID NO: 35)) led to an increase in survival, whereas addition of an irrelevant Th epitope did not, even though the addition of either Th epitope to the vaccine resulted in greater CTL activity (Kennedy and Celis, 2006, *J. Immunol.* 177:2862-2872). Since non-specific Th cells had no beneficial effect on survival, it seems that tumor-specific $CD4^+$ Th cells directly provide help at the tumor sites.

Further analysis of this "antigen-specific benefit" in an in vitro model revealed that the Th cells protect CTLs from activation-induced cell death (AICD), which allows CTLs to survive and to continue to kill tumor cells (Kennedy and Celis, 2006, *J. Immunol.* 177:2862-2872). This model is supported by the facts that $CD4^+$ T cells are required for secondary expansion and memory in $CD8^+$ T cells (Janssen et al., 2003, *Nature* 421:852-856; Shedlock and Shen, 2003, *Science* 300:337-339; Sun and Bevan, 2003, *Science* 300:339-342), and that adoptive transfer of gene-engineered $CD4^+$ Th cells induces potent primary and secondary tumor rejections (Moeller et al., 2005, *Blood* 106(9):2995-3003). It is also supported by studies in infectious diseases, where HIV-specific $CD4^+$ T cells are essential for the maintenance of effective CTL responses and the generation of functional CTL memory cells (Lichterfeld et al., 2004, *J. Exp. Med.* 200: 701-712; Kavanach et al., 2006, *Blood* 107:1963-1969), and are associated with the low HIV viremia in long-term non-progressors (Boar et al., 2002, *J. Immunol.* 169:6376-6385).

The MHC class II-associated invariant chain (Ii), or CD74, acts as a chaperone for Ag presentation in the context of MHC class II (Stein et al., 2007, *Clin. Cancer Res.* 13:5556s-5563s; Matza et al., 2003, *Trends Immunol.* 24:264-268). Fusion of antigen to Ii has been shown to increase the priming of antigen-specific $CD4^+$ T cells in vitro and in vivo (Diebold et al., 2008, *J. Immunol.* 180:3339-3346; Rowe et al., 2006, *Mol. Ther.* 13:310-319). Furthermore, an adenovirus-encoded vaccine tethered to Ii resulted in a dramatically improved cellular immunity with augmented presentation of MHC class I-restricted epitopes (Holst et al., 2008, *J. Immunol.* 180:3339-3346; Grujic et al., 2009, *J. Gen. Virol.* 90:414-422). Thus, linking antigens to Ii may provide a strategy for improved vaccination (FIG. 1).

Harnessing DCs to Break Tolerance

Numerous studies have been performed using DCs, the professional and most potent APCs, to create both preventive and therapeutic vaccines against cancer and infectious diseases, with proven efficacy in animal models and patients. However, significant clinical benefit has not previously been achieved with DC-based immunotherapy. Recent advances in DC vaccination, which can be achieved either ex vivo or in vivo, are now being evaluated in clinical trials.

Vaccination with Mature DC Generated Ex Vivo

Immature DCs differ from mature DCs not only in the lower T-cell stimulatory capacity due to a low level of MHC class I/II and costimulatory molecules, but also in their lower capacity of migration. Mature DCs induce T-cell immunity, whereas immature DCs induce tolerance. A DC-based cancer vaccine thus requires fully mature DCs for effective induction of functionally specific T cells against tumors. Since $CD4^+$ T cells provide T-cell help for generating and augmenting tumor-specific CTL responses, and Th1 effector cells play a key role in mediating cellular immunity, DCs that can skew the differentiation of naïve $CD4^+$ T cells toward Th1 cells, which are termed type-1 DCs (DC1), are preferred for DC-based vaccines.

The in vitro generation of DC1 is largely dependent on the stimulation factors that induce DC maturation. It was reported that stimulation of bone marrow-derived murine dendritic cell populations with poly(I:C) and CpGs results in phenotypic maturation of dendritic cells toward DC1, which are characterized as a durable and high-level IL-12p70 secretion and induction of Th1-skewed, tumor-specific, $CD4^+$ T-cell response (Hokey et al., 2005, *Cancer Res.* 65(21): 10059-10067). Polarized DC1 that produces high levels of IL-12 family members can rescue patient Th1-type anti-melanoma $CD4^+$ T cell responses in vitro (Wesa et al., 2007, *J. Immunother.* 30(1):75-82).

Furthermore, a unique protocol (Mailliard et al., 2004, *Cancer Res.* 64:5934-5937) was developed to generate fully mature type-1 human DCs (αDC1) using an optimized maturation cocktail comprising IL-1-β, TNF-α, IFN-α, IFN-γ, and poly(I:C). It was shown that, compared with standard DCs matured by IL-1-β, TNF-α, IL-6, and PGE2, αDC1 expressed similar levels of multiple costimulatory molecules (CD83, CD86, CD80, CD11c, and CD40), but secreted 10 to 60 times more IL-12p70, and induced much higher numbers of functional $CD8^+$ T cells against CLL cells, indicating this type of DC is the potent inducer of tumor-specific T cells (Lee et al., 2008, *J. Leukoc. Biol.* 84(1):319-325). In addition, αDC1 potently recruits and activates NK cells (Gustafsson et al., 2008, *Cancer Res.* 68(14):5965-5971). Unlike standard DCs (sDC) generated in the presence of PGE2, αDC1 lacks the ability of attracting Tregs (Muthuswamy et al., 2008, *Cancer Res.* 68: 5972-5978). Analysis of the αDC1 maturation cocktail indicated that IFN-γ is the key player for priming DCs to produce high-levels of IL-12 (Mailliard et al., 2004, *Cancer Res.* 64:5934-5937) and CXCL9/MIG (Gustafsson et al., 2008, *Cancer Res.* 68(14):5965-5971), and IFN-α is a potent inducer of CCR-7 expression, which is essential for efficient migration of DCs to secondary lymphoid organs (Parlato et al., 2001, *Blood* 98:3022-3029; Mohty et al., 2003, *J. Immunol.* 171:3385-3393; Papewalis et al., 2008, *J. Immunol.* 180:1462-1470).

Taken together, given the ability to generate DCs with full maturation, acquisition of CCR-7 expression, Th1 polarization and potent induction of tumor-specific CTLs, this type of maturation cocktail is likely to be used for developing a new generation of ex vivo manipulated DCs for future clinical trials (FIG. 1), even though it was recently reported that higher up-regulation of inhibitory molecules, such as PD-L1, ILT2, and ILT3, was found in αDC1 as compared to sDC when generated in a clinical protocol using X-VIVO15. However, αDC1 still consistently secreted more IL-12p70 and IL-23 than sDCs (Trepiakas et al., 2008, *Vaccine* 26:2824-2832).

A further modification of DCs to enhance their T-cell stimulatory capacity involves the use of lentiviral vectors to engineer the expression of calnexin (Kang et al., 2002, *J. Biol. Chem.* 277:44838-44844), which converts tolerogenic DCs into reactive DCs in multiple myeloma and effectively overcomes immune tolerance (Han et al., 2008, *Mol. Ther.* 16:269-279) (FIG. 1).

Vaccination with DC-Derived Exosomes

Exosomes are 30- to 100-nm diameter vesicles derived from a diverse range of cell types. DC-derived exosomes contain Ag-presenting, adhesion, and costimulatory molecules, which alone or in association with DCs can serve as a potent vaccine to stimulate strong CTL responses and induce antitumor immunity in different animal models (Chaput et al., 2004, *J. Immunol.* 172:2137-2146; Cho et al., 2005, *Int. J. Cancer* 114:613-622; Hao et al., 2007, *Immunology* 120:90-102).

For example, mature DCs pulsed with exosomes stimulate efficient CTL responses and antitumor immunity (Hao et al., 2007, *Immunology* 120:90-102), and active CD4$^+$ T cells following uptake of OVA-pulsed, DC-derived exosomes, can stimulate CD8$^+$ T cell to proliferate and differentiate into central memory CD8$^+$ CTLs, resulting in not only more efficient in vivo antitumor immunity and long-term CD8$^+$ T-cell memory responses than OVA-pulsed dendritic cells, but also the ability to counteract CD4$^+$25$^+$ regulatory T-cell-mediated immune suppression (Hao et al., 2007, *J. Immunol.* 179:2731-2740). Thus, such exosome-targeted active CD4$^+$ T cells may represent a novel and highly effective cancer vaccine (FIG. 1).

Vaccination with In Vivo Targeted Dc

In vivo targeting of antigens to DCs represents a promising approach for DC-based vaccination, as it can bypass the laborious and expensive ex-vivo antigen loading and culturing, facilitating large-scale application of DC-based immunotherapy (Tacken et al., 2007, *Nat. Rev. Immunol.* 7:790-802). More importantly, in vivo DC-targeted vaccination was reported to be more efficient in eliciting an anti-tumor immune response, and more effective in controlling tumor growth in animal models (Bonifaz et al., 2004, *J. Exp. Med.* 199:815-824; Kretz-Rommel et al., 2007, *J. Immunother.* 30:715-726).

One promising strategy developed for in-vivo targeted DC vaccination is to use engineered lentiviral vectors that specifically bind to the DC surface protein, DC-SIGN (Yang et al., 2008, *Nat. Biotechnol.* 26:326-334). Successful transduction of DCs in vivo by direct injection of a lentiviral vector encoding the human melanoma antigen, NY-ESO-1, under mouse dectin-2 gene promoter that restricted transgene expression to antigen-presenting cells, was also evidenced (Lopes et al., 2008, *J. Virol.* 82:86-95) by priming an NY-ESO-1-specific CD8$^+$ T-cell response in HLA-A2 transgenic mice, and stimulating a CD4$^+$ T-cell response to a newly identified NY-ESO-1 epitope presented by H2 I-A(b). These results indicate that targeting antigen expression to DCs with lentiviral vectors can provide a safe and effective vaccine (FIG. 1).

Targeting antigens to DCs via an antibody specific to a select DC cell surface marker is another approach for in-vivo targeted DC vaccination, as reported for mannose receptor (He et al., 2007, *J. Immunol.* 178:6259-6267; Ramakrishna et al., 2004, *J. Immunol.* 172(5), 2845-2852), CD205 (Trumpfheller et al., 2006, *J. Exp. Med.* 203:607-617; Gurer et al., 2008, *Blood* 112:1231-1239), DC-SIGN (Tacken et al., 2005, *Blood* 106:1278-1285), and LOX1 (Delneste et al., 2002, *Immunity* 17(3):353-362). In addition, the potential use of CD74 for in-vivo targeted DC vaccination is being explored by us. CD74 is a type-II integral membrane protein essential for proper MHC II folding and MHC II-CD74 complex targeting to endosomes (Stein et al., 2007, *Clin. Cancer Res.* 13:5556s-5563s; Matza et al., 2003, *Trends Immunol.* 24:264-268). CD74 expression is not restricted to DCs, but is in almost all antigen-presenting cells (Freudenthal et al., 1990, *Proc. Natl. Acad. Sci. U.S.A.* 87:7698-7702), including B cells, monocytes, and different DC subsets, such as blood myeloid DC1, myeloid DC2, plasmacytoid DC (Chen et al., 2008, *Blood (ASH Annual Meeting Abstracts)* 112: Abstract 2649), and follicular DCs (Clark et al., 1992, *J. Immunol.* 148:3327-3335).

The broad expression of CD74 in APCs may offer some advantages over sole expression in myeloid DCs, because targeting of antigens to other APCs, like B cells, has been reported to break immune tolerance (Ding et al., 2008, *Blood* 112:2817-2825), and targeting to plasmacytoid DCs cross-presents antigens to naïve CD8 T cells (Mouries et al., 2008, *Blood* 112:3713-3722). Furthermore, CD74 is also expressed in follicular DCs, a DC subset critical for antigen presentation to B cells (Clark et al., 1992, *J. Immunol.* 148:3327-3335).

The humanized anti-CD74 monoclonal antibody, hLL1 or milatuzumab (Leung et al., 1995, *Mol. Immunol.* 32:1416-1427; Losman et al., 1997, *Cancer* 80(12 Suppl):2660-2666; Stein et al., 2004, *Blood* 104:3705-3711), is a therapeutic MAb currently under clinical evaluation for non-Hodgkin lymphoma, chronic lymphocytic leukemia, and multiple myeloma. Milatuzumab binds efficiently to different subsets of blood DCs, B cells, monocytes, and monocyte-derived immature DCs, but has no cytotoxicity, nor functional alteration, on human monocyte-derived DCs that normally express CD74 (Chen et al., 2008, *Blood (ASH Annual Meeting Abstracts)* 112: Abstract 2649). These properties of milatuzumab, which internalizes rapidly upon engagement with CD74, favor its use as a DC-targeting antibody for in vivo vaccination.

Vaccination Against Cancer Stem Cells

Cancer stem cells (CSCs) are capable of self-renewal, possess the ability for unlimited proliferation, and are resistant to multiple therapeutic approaches, whereas most mature cancer cells can be eliminated effectively by current standard therapies. A pressing question is whether cancer stem cells are sensitive to immunotherapy or vaccination. In the case of leukemia, it was reported that CD8$^+$ minor histocompatibility antigen-specific cytotoxic T lymphocyte clones could eliminate human acute myeloid leukemia stem cells (Bonnet et al., 1999, *Proc. Natl. Acad. Sci. U.S.A.* 96:8639-8644). More recently, Rosinski et al. reported that DDX36-encoded H-Y epitope is expressed by leukemic stem cells and can be recognized by the DDX36-specific CTLs, which can prevent engraftment of human acute leukemia in NOD/SCID mice (Rosinski et al., 2008, *Blood* 111:4817-4826). Another report demonstrated that engraftment of mHA myeloid leukemia stem cells in NOD/SCIDγc$^{null}$ mice was completely inhibited by in vitro preincubation with the mHA-specific CTL clone (Kawase et al., 2007, *Blood* 110:1055-1063). These results predict the prospects that immunotherapy would be a potentially effective approach for selective elimination of cancer stem cells, which could lead to long-term control of cancer.

However, it is still unknown whether CSCs, like many cancer cells, are subject to immune tolerance or evasion. CD200, an immunosuppressive membrane glycoprotein overexpressed in multiple hematological malignancies, and a negative prognostic factor in multiple myeloma (Moreaux et al., 2006, *Blood* 108:4194-4197) and acute myeloid leukemia (Tonks et al., 2007, *Leukemia* 21:566-568), has been found to be co-expressed in CSCs with other stem-cell markers in prostate, breast, brain, and colon cancers (Kawasaki et al., 2007, *Biochem. Biophys. Res. Commun.* 364:778-782). This suggests that CSCs might be able to evade immune surveillance or immunotherapy by generating a tolerogenic response facilitated by the expression of CD200 (Kawasaki et al., 2008, *Trends Immunol.* 29:464-468). This fact may increase the difficulty of eliminating CSCs by immunotherapy approaches. However, it is still unclear whether CSCs are more resistant to CTL killing than their progeny cells, and if so, whether CD200 is a key player for mediating the immune resistance.

Cancer Vaccine in Combination with Adoptive Transfer of T Cells

Adoptive transfer of TCR gene-modified T cells is an attractive approach for the immunotherapy of tumors, especially for those types where it is difficult or impossible to induce strong T-cell responses by vaccination, and has shown encouraging results in preclinical (Engels et al., 2005, *Hum. Gene Ther.* 16:799-810; de Witte et al., 2008, *J. Immunol.* 181:2563-2571; de Witte et al., 2008, *J. Immunol.* 181:5128-5136) and clinical studies (Morgan et al., 2006, *Science* 314: 126-129). Moreover, combining vaccination and T-cell adoptive transfer can exploit the benefits of both modalities. In addition, as adoptive T cells have the lifespan of the host, vaccination can boost the tumor-specific T cells when needed.

Experimental evidence to support this approach was provided in a spontaneous prostate carcinoma mouse model that whereas vaccination or TCR gene transfer by itself was entirely without effect, the combination of vaccination with TCR gene transfer was highly synergistic in suppressing tumor development (de Witte et al., *J. Immunol.* 181:2563-2571). Thus, vaccines combined with adoptive T-cell therapy could greatly improve the efficacy of cancer immunotherapy, and was reported to be the most effective strategy for treating established B16 murine melanoma (Kochenderfer et al., 2007, *Exp. Biol. Med.* (*Maywood*) 232(9):1130-41) (FIG. 1).

Cancer Vaccine in Combination with Chemotherapy and/or Monoclonal Antibodies

Because of the immunosuppressive effects of cytotoxic therapy, it is a challenge to integrate cancer vaccines into the standard chemotherapy of cancer. However, chemotherapy or radiotherapy was reported to eliminate regulatory T cells (Tregs) (North et al., 1986, *J. Exp. Med.* 164:1652-1666; Awwad et al., 1989, *Cancer Res.* 49:1649-1654; Ercolini et al., 2005, *J. Exp. Med.* 201:1591-1602), which would potentially offer some synergistic action with vaccine-induced anti-tumor effects. This has been confirmed by several clinical trials showing that vaccinated patients receiving subsequent chemotherapy exhibited better outcomes (longer post-chemotherapy recurrence times and survival) than vaccination or chemotherapy alone (Baxevanis et al., 2009, *Cancer Immunol. Immunother.* 58:317-324; Wheeler et al., 2004, *Clin. Cancer Res.* 10:5316-5326; Antonia et al., 2006, *Clin. Cancer Res.* 12:878-887).

Modification of the tumor microenvironment by NSAIDs, such as cyclooxygenase-2 (COX-2) inhibitors, could enhance the clinical efficacy of the cancer vaccine. This is because COX-2 and its downstream prostaglandins are capable of inhibiting DC and T effector cell activity, and of stimulating Tregs (Juuti et al., 2006, *J. Clin. Pathol.* 59:382-386; Sharma et al., 2003, *Clin. Cancer Res.* 9: 961-968; Sharma et al., 2005, Cancer Res. 65:5211-5220; Basu et al., 2006, *J. Immunol.* 177(4): 2391-2402). In a triple transgenic mouse model of spontaneous pancreatic cancer induced by the $KRAS^{G12D}$ mutation and that expresses human MUC1 as a self molecule, combination of a MUC1-specific vaccine with the COX-2 inhibitor, celecoxib, elicited robust antitumor cellular and humoral immune responses, and was associated with increased apoptosis in the tumor. Strikingly, the immunization was effective only in combination with COX-2 inhibition (Mukherjee et al., 2009, *J. Immunol.* 182:216-24).

Monoclonal antibodies, either unconjugated or conjugated with radionuclides, are effective in cancer therapy (Sharkey et al., 2006, *CA Cancer J. Clin.* 56:226-243; Sharkey et al., 2008, *Adv. Drug Deliv. Rev.* 60:1407-1420). Unconjugated monoclonal antibodies exert their anti-tumor cytotoxicity usually by the mechanisms of complement-mediated cytotoxicity (CMC) and antibody-dependent cellular cytotoxicity (ADCC), or by initiating or inhibiting signaling pathways in the targeted cell that leads to apoptosis (Sharkey et al., 2006, *CA Cancer J. Clin.* 56:226-243). Thus, combining vaccine, monoclonal antibody, and chemotherapy may hold more potential for enhancing therapeutic efficacy (Baxevanis et al., 2009, *Cancer Immunol. Immunother.* 58:317-324) (FIG. 1).

Vaccination in Combination with Stem-Cell Transplantation

Allogeneic hematopoietic stem cell transplantation (allo-HSCT), following high-dose chemotherapy and total body irradiation, provides an effective and potentially curative therapy for hematologic malignancies. It is believed that the clinical effectiveness of this approach is primarily due to the graft versus leukemia (GVL) effect, in which the recipient leukemia cells are recognized and eliminated by donor T cells. The primary target antigen for allo-HSCT with HLA-identical donors is minor-histocompatibility antigen (mHA), which is derived from genetic polymorphisms in the recipient that are not present in the donor (Ofran et al., 2008, *Clin. Cancer Res.* 14:4997-4999; Tykodi et al., 2008, *Clin. Cancer Res.* 14(16):5260-5269). Due to the slow and incomplete immune reconstitution following HSCT, immunization in HSCT is frequently unsuccessful (Aqui et al., 2008, *Best Pract. Res. Clin. Haematol.* 21:503-519).

However, effective antitumor immunity was reported to be elicited by tumor vaccination after allo-HSCT in murine models (Anderson et al., 2000, *Blood* 95:2426-2433; Teshima et al., 2001, *Cancer Res.* 61:162-171; Moyer et al., 2006, *Biol. Blood Marrow Transplant.* 12:1010-1019). Recently, it was reported in a clinical study (Kitawaki et al., 2008, *Am. J. Hematol.* 83:315-317) that DC vaccination with Wilms' tumor 1 (WT1) peptide and keyhole limpet hemocyanin (KLH) after allo-HSCT successfully induced immune responses to the naïve antigen KLH, even though a definitive immune response to WT1 was not detected. This result indicates that DC vaccination may be a viable strategy for antigen-specific immunotherapy after allo-HSCT (FIG. 1).

Improved Vaccination Schedule to Enhance Anti-Tumor Efficacy

One of the advances in vaccinology is heterologous prime-boost, which involves a sequential vaccination schedule with different antigen delivery systems encoding the same antigen (Hodge et al., 2003, *Cancer Res.* 63:7942-7949; Harrop et al., 2006, *Adv. Drug Deliv. Rev.* 58:931-947). This vaccination schedule was initially designed to circumvent the problem associated with viral vector-induced neutralizing antibody when given on multiple occasions. In this case, a huge number of immune cells specific for the viral vector rather than the cells specific for the encoded antigen can be expanded, which greatly limits the efficacy of vaccination. The use of one viral vector to prime an immune response and a different viral vector to boost the response can minimize the expansion of immune cells specific for vector proteins, which would favor the immune response to the target antigen (Harrop et al., 2006, *Adv. Drug Deliv. Rev.* 58:931-947).

As for DNA vaccination, a heterologous prime/boost strategy consisting of plasmid delivered melanoma antigen tyrosinase, followed by recombinant alphavirus replicon particles encoding the same antigen, resulted in a better immune response and tumor protection than vaccinating with plasmid DNA alone (Goldberg et al., 2005, *Clin. Cancer Res.* 11:8114-8121). Also, prostate stem cell antigen vaccination induces a long-term protective immune response without autoimmunity (Garcia-Hernandez et al., 2008, *Cancer Res.* 68:861-869). The optimal combination of different vectors and the order in which they should be used to prime and subsequently boost the immune response remains under investigation (Harrop et al., 2006, *Adv. Drug Deliv. Rev.* 58:931-947). Recently, a single heterologous prime-boost trial comparing multiple vaccine vectors identified recombinant vesicular stomatitis virus (rVSV) and recombinant Venezuelan equine encephalitis virus replicons (VRP) as the most synergistic regimen (Barefoot et al, 2008, *Vaccine.* 26(48): 6108-6118).

Xenoantigens

In embodiments involving vaccines against cancer, the vaccines will comprise a tumor-specific antigen or a tumor-associated antigen. While vaccines against tumor-specific antigens provide the greatest selectivity against tumor cells, the need to specifically tailor such vaccines for the individual patient limits their widespread applicability. In contrast, tumor-associated antigens (TAAs), which may be found to a limited extent in cells of normal tissues, exhibit a much broader distribution across tumors from different patients or even different tumor types. In more preferred embodiments, the anti-cancer vaccines are targeted to TAAs. A wide variety of TAAs are known in the art and any such known TAA may be used as the basis for an anti-cancer vaccine.

In certain preferred embodiments, the TAA is a CD20 xenoantigen, of use to induce an immune response against B cell cancers such as leukemias or lymphomas, or against autoimmune diseases involving B cell proliferation. Other known TAAs include, but are not limited to, carbonic anhydrase IX, alpha-fetoprotein, α-actinin-4, A3, antigen specific for A33 antibody, ART-4, B7, Ba 733, BAGE, BrE3-antigen, CA125, CAMEL, CAP-1, CASP-8/m CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CDC27, CDK-4/m, CDKN2A, colon-specific antigen-p (CSAp), CEA (CEACAM5), CEACAM6, DAM, EGFR, EGFRvIII, EGP-1, EGP-2, ELF2-M, Ep-CAM, Flt-1, Flt-3, folate receptor, G250 antigen, GAGE, gp100, GROB, HLA-DR, HM1.24, human chorionic gonadotropin (HCG) and its subunits, HER2/neu, HMGB-1, hypoxia inducible factor (HIF-1), HSP70-2M, HST-2, Ia, IGF-1R, IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, insulin growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUM-1/2, MUM-3, NCA66, NCA95, NCA90, antigen specific for PAM-4 antibody, placental growth factor, p53, prostatic acid phosphatase, PSA, PRAME, PSMA, P1GF, ILGF, ILGF-1R, IL-6, IL-25, RS5, RANTES, T101, SAGE, S100, survivin, survivin-2B, TAC, TAG-72, tenascin, TRAIL receptors, TNF-α, Tn antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, cMET, an oncogene marker and an oncogene product (see, e.g., Sensi et al., Clin Cancer Res 2006, 12:5023-32; Parmiani et al., J Immunol 2007, 178:1975-79; Novellino et al. Cancer Immunol Immunother 2005, 54:187-207).

Xenoantigen amino acid sequences for a large number of TAAs, such as murine protein amino acid sequences, may be readily obtained from public databases, such as the NCBI protein database. For example, xenoantigen CD20 amino acid sequences of potential use are readily available to the skilled artisan through such well-known public databases as the NCBI protein database (see, e.g., NCBI Accession Nos. NP 031667; P 19437; AAA37394; BAE47068; ABA29631; BAD77809). Although the murine CD20 sequence is recited herein, the skilled artisan will realize that CD20 amino acid sequences are known and readily available from a wide variety of species and can be incorporated into the anti-cancer vaccine complexes. Because the xenoantigen amino acid sequence is from a different species, the likelihood of self-tolerance of the host immune system is substantially reduced.

Dendritic Cell Targeting Antibodies

In certain embodiments, the antigen to be used for vaccine production may be targeted to appropriate host cells, such as dendritic cells (DC), by attachment to an appropriate targeting antibody. In a preferred embodiment, the DC-targeting antibody may be an anti-CD74 antibody, such as the hLL1 antibody (see U.S. Pat. No. 7,312,418, the Examples section of which is incorporated herein by reference). However, other antigens associated with DCs are known, including but not limited to CD209 (DC-SIGN), CD34, CD74, CD205, TLR 2 (toll-like receptor 2), TLR 4, TLR 7, TLR 9, BDCA-2, BDCA-3, BDCA-4, and HLA-DR. Any such known DC antigen may be targeted using an appropriate antibody vaccine component. An exemplary anti-HLA-DR antibody is hL243 (see U.S. Pat. No. 7,612,180, the Examples section of which is incorporated herein by reference).

Vaccines for Therapy of Multiple Myeloma and Other Cancers

CD20 is normally expressed in cells of B cell lineage. It was recently reported that CD20 is expressed in a small population of MM cells isolated from MM cell lines or clinical specimens, which do not express the characteristic plasma cell surface antigen CD138 but have a highly clonogenic potential and are resistant to multiple clinical anti-myeloma drugs (Matsui et al., Blood 2004, 103:2332-6; Matsui et al., *Cancer Res.* 2008, 68:190-7). These CD20+CD138-cells are capable of clonogenic growth in vitro and in a 3-D culture model (Kirshner et al., Blood 2008, 112:2935-45), and of differentiation into MM cells in vitro and in the engrafted NOD/SCID mouse model during both primary and secondary transplantation. It has thus been suggested that these CD138$^{neg}$CD20$^+$ cells represent the putative multiple myeloma cancer stem cells.

Immunization with Xenoantigen as a Means for Breaking Immune Tolerance for Cancer Immunotherapy.

Many tumor-associated Ags (TAAs) represent tissue differentiation Ags which are not inherently immunogenic. T cells that recognize these TAAs/self-Ags with high avidity are either clonally deleted in the thymus or anergized in the periphery. However, immunization with xenoantigen has been shown to be capable of overcoming the immune tolerance against the homologous self-Ag (Fong et al., *J Immunol.* 2001, 167(12):7150-6). These results demonstrate that xenoantigen immunization can break tolerance to a self-Ag in humans, resulting in a clinically significant antitumor effect.

CD20 as a Target for Immunotherapy and Vaccination Against MM.

As stated above, CD20 is a hallmark of MM cancer stem cells. As a self-antigen which is expressed on normal B cells at most stages of differentiation, it is theoretically difficult to be targeted by vaccine strategies due to immune tolerance. However, successful vaccination has been achieved by a xenogeneic DNA vaccine against CD20 in a tumor challenge model of B-cell lymphoma. Although autoimmunity against B cells could be induced by a vaccine targeting CD20, it should not cause a large problem because the B cell pool is not a vital and critical tissue and can be replenished from its lineage progenitor. Based on these considerations, a therapeutic vaccine targeting CD20 would be effective in selective eradication of MM cancer stem cells.

Monoclonal Anti-CD20 Antibody as a Potential Modality for Eradication of MM Stem Cells.

The discovery of CD20+ MM progenitor cells has prompted several small clinical trials to test the efficacy of rituximab, an anti-CD20 monoclonal antibody, in MM patients. As reviewed by Kapoor et al. (Br J Haematol. 2008, 141:135-48), anti-CD20 therapy with rituximab elicits a partial response in approximately 10% of CD20+ patients with multiple myeloma. In addition, there is preliminary evidence of disease stabilization in 50-57% of CD20+ patients for a period of 10-27 months (Kapoor et al., (Br J Haematol. 2008, 141:135-48). Furthermore, a case report by Bergua et al. (Leukemia. 2008, 22:1082-3) where rituximab was used in combination with chemotherapy demonstrated no minimal residual disease found after treatment, either in immunophenotype, bone marrow aspiration or biopsy, and the CD20+ plasma cells disappeared. The vaccine approach, due to its induction of CTL response, would be expected to supplement the monoclonal antibody therapy against CD20 MM stem cells.

In Vivo Targeting of Antigens to Dendritic Cells and Other Antigen-Presenting Cells as an Efficient Strategy for Vaccination and Breaking Immune Tolerance.

As the professional antigen-presenting cells, dendritic cells (DCs) play a pivotal role in orchestrating innate and adaptive immunity, and have been harnessed to create effective vaccines (Vulink et al., Adv Cancer Res. 2008, 99:363-407; O'Neill et al., Mol Biotechnol. 2007, 36:131-41). In vivo targeting of antigens to DCs represents a promising approach for DC-based vaccination, as it can bypass the laborious and expensive ex vivo antigen loading and culturing, and facilitate large-scale application of DC-based immunotherapy (Tacken et al., Nat Rev Immunol. 2007, 7:790-802). More significantly, in vivo DC targeting vaccination is more efficient in eliciting anti-tumor immune response, and more effective in controlling tumor growth in animal models (Kretz-Rommel et al., J Immunother 2007, 30:715-726). In addition to DCs, B cells are another type of potent antigen-presenting cells capable of priming Th1/Th2 cells (Morris et al, J Immunol. 1994, 152:3777-3785; Constant, J Immunol. 1999, 162: 5695-5703) and activating CD8 T cells via cross-presentation (Heit et al., J Immunol. 2004, 172:1501-1507; Yan et al., Int Immunol. 2005, 17:869-773). It was recently reported that in vivo targeting of antigens to B cells breaks immune tolerance of MUC1 (Ding et al., Blood 2008, 112:2817-25).

CD74 as a Potential Receptor for Targeting Vaccination.

Some receptors expressed on DCs have been used as the targets for in vivo antigen targeting, such as the mannose receptor (He et al., J. Immunol 2007, 178, 6259-6267; Ramakrishna et al., J. Immunol. 2004, 172, 2845-2852) CD205 (Bonifaz et al., *J Exp Med.* 2004, 199:815-24), DC-SIGN (Tacken et al., Blood 2005, 106:1278-85), and LOX1 (Deineste et al., Immunity 2002, 17, 353-362), etc. CD74 is a type II integral membrane protein essential for proper MHC II folding and targeting of MHC II-CD74 complex to the endosomes (Stein et al., Clin Cancer Res. 2007, 13:5556s-5563s; Matza et al., *Trends Immunol.* 2003, 24(5):264-8). CD74 expression is not restricted to DCs, but is found in almost all antigen-presenting cells (Freudenthal et al., Proc Natl Acad Sci USA. 1990, 87:7698-702; Clark et al., J Immunol. 1992, 148(11):3327-35). The wide expression of CD74 in APCs may offer some advantages over sole expression in myeloid DCs, as targeting of antigens to other APCs like B cells has been reported to break immune tolerance (Ding et al., Blood 2008, 112:2817-25), and targeting to plasmacytoid DCs cross-presents antigens to naïve CD8 T cells. More importantly, CD74 is also expressed in follicular DCs (Clark et al., J Immunol. 1992, 148(11):3327-35), a DC subset critical for antigen presentation to B cells (Tew et al., Immunol Rev. 1997, 156:39-52). This expression profile makes CD74 an excellent candidate for in vivo targeting vaccination.

Humanized Anti-CD74 Monoclonal Antibody hLL1 as a Novel Targeting Tool with Dock-and-Lock Technology Platform.

The DNL technology, discussed in more detail below, provides a means to link virtually any selected effector moieties into a covalent or noncovalent complex (Goldenberg et al., J Nucl Med. 2008, 49:158-63; Rossi et al., Proc Natl Acad Sci USA. 2006, 103(18):6841-6). The DNL method has generated several trivalent, bispecific, binding proteins containing Fab fragments reacting with carcinoembryonic antigen (CEA), and has been successfully used in improved cancer imaging and radioimmunotherapy through a pretargeting strategy (Goldenberg et al., J Nucl Med. 2008, 49:158-63).

hLL1 is a humanized monoclonal antibody against human CD74 (Leung et al., Mol Immunol. 1995, 32:1416-1427; Losman et al., Cancer 1997, 80:2660-2666; Stein et al., Blood 2004, 104:3705-11). This MAb, in the presence of cross-linking by a second antibody, exhibits cytotoxicity against B cell malignancies. The naked hLL1 is also capable of controlling tumor growth in a MM mouse model. However, our recent data demonstrate that hLL1, in the presence or absence of cross-linking, has no cytotoxicity against human monocyte-derived DCs. But, our preliminary data shows hLL1 could efficiently bind different subsets of blood DCs and B cells. It also could moderately induce DC maturation and polarize naïve T cell differentiation toward Th1 effector cells, suggesting it has some adjuvant activity and may be a good candidate for use as a targeting tool. This makes it possible and feasible to construct a DNL-based tumor vaccine targeted to APCs through the DNL-carried hLL1 antibody.

Immunotherapy for Selective Elimination of Cancer Stem Cells.

Cancer stem cells are capable of self-renewal, possess the ability for unlimited proliferation, and are resistant to multiple therapeutic approaches. In the case of leukemia, it was reported that CD8(+) minor histocompatibility antigen-specific cytotoxic T lymphocyte clones could eliminate human acute myeloid leukemia stem cells (Bonnet et al., Proc Natl Acad Sci U.S.A. 1999, 96:8639-8644). As discussed above, other results suggest that a vaccine-based immunotherapy approach may be effective to eliminate cancer stem cells. These results indicate that immunotherapy is a potentially effective approach for selective elimination of cancer stem cells including MM stem cells, which would be required for achieving long-term control or even cure of this malignancy.

Dock and Lock (DNL) Method

In certain embodiments, the vaccine constructs to be prepared and used may be made by the novel dock-and-lock (DNL) technique (see, e.g., U.S. Pat. Nos. 7,521,056; 7,527,787; 7,534,866; 7,550,143 and 7,666,400, the Examples section of each of which is incorporated herein by reference.) The DNL method is based on the specific protein/protein interactions between the regulatory (R) subunits of cAMP-dependent protein kinase (PKA) and the anchoring domain (AD) of A-kinase anchoring proteins (AKAPs) (Baillie et cd., FEBS Letters. 2005; 579: 3264. Wong and Scott, Nat. Rev. Mol. Cell. Biol. 2004; 5: 959). PKA, which plays a central role in the signal transduction pathway triggered by the binding of cAMP to the R subunits of PKA, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265:21561).

Since the first AKAP, microtubule-associated protein-2, was characterized in 1984 (Lohmann et al., Proc. Natl. Acad. Sci USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Carr et al., J. Biol. Chem. 1991; 266:14188) and any such known AD sequence may be utilized to form a DNL complex. The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). Interestingly, AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

DDD of Human RIIα and AD of AKAPs as Linker Modules

We have developed a platform technology to utilize the DDD of human RIIα and the AD of AKAPs as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions bring the reactive thiol groups placed onto both the DDD and AD into proximity (Chimura et al., Proc. Natl. Acad. Sci. USA. 2001; 98:8480) to ligate site-specifically.

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, nucleic acids, cytokines and PEG.

DDD and AD Sequence Variants

In certain embodiments, the AD and DDD sequences incorporated into the vaccine complex comprise the amino acid sequences of DDD1 (SEQ ID NO:1) and AD1 (SEQ ID NO:3) below. In more preferred embodiments, the AD and DDD sequences comprise the amino acid sequences of DDD2 (SEQ ID NO:2) and AD2 (SEQ ID NO:4), which are designed to promote disulfide bond formation between the DDD and AD moieties.

```
DDD1
                                              (SEQ ID NO: 1)
SHIQIPPGLTELLQGYTVEVLRQQPPDLVEFAVEYFTRLREARA

DDD2
                                              (SEQ ID NO: 2)
CGHIQIPPGLTELLQGYTVEVLRQQPPDLVEFAVEYFTRLREARA

AD1
                                              (SEQ ID NO: 3)
QIEYLAKQIVDNAIQQA

AD2
                                              (SEQ ID NO: 4)
CGQIEYLAKQIVDNAIQQAGC
```

However, in alternative embodiments sequence variants of the AD and/or DDD moieties may be utilized in construction of the vaccine complexes. The structure-function relationships of the AD and DDD domains have been the subject of investigation. (See, e.g., Burns-Hamuro et al., 2005, Protein Sci 14:2982-92; Can et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400:493-99; Gold et al., 2006, Mol Cell 24:383-95; Kinderman et al., 2006, Mol Cell 24:397-408.)

For example, Kinderman et al. (2006) examined the crystal structure of the AD-DDD binding interaction and concluded that the human DDD sequence contained a number of conserved amino acid residues that were important in either dimer formation or AKAP binding, underlined below in SEQ ID NO:1. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding. Thus, a potential alternative DDD sequence of use for construction of DNL complexes is shown in SEQ ID NO:5, wherein "X" represents a conservative amino acid substitution. Conservative amino acid substitutions are discussed in more detail below, but could involve for example substitution of an aspartate residue for a glutamate residue, or a leucine or valine residue for an isoleucine residue, etc. Such conservative amino acid substitutions are well known in the art.

Human DDD Sequence from Protein Kinase A

```
                                              (SEQ ID NO: 1)
SHIQIPPGLTELLQGYTVEVLRQQPPDLVEFAVEYFTRLREARA (SEQ ID NO: 5)
XXIXIXXXLXXLLXXYXVXVLXXXXXXLVXFXVXYFXXLXXXXX
```

Alto et al. (2003) performed a bioinformatic analysis of the AD sequence of various AKAP proteins to design an RII selective AD sequence called AKAP-IS (SEQ ID NO:3), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:3. Therefore, the skilled artisan will realize that variants which may function for DNL constructs are indicated by SEQ ID NO:6, where "X" is a conservative amino acid substitution.

AKAP-IS Sequence

```
QIEYLAKQIVDNAIQQA      (SEQ ID NO: 3)

XXXXXAXXIVXXAIXXX      (SEQ ID NO: 6)
```

Similarly, Gold (2006) utilized crystallography and peptide screening to develop a SuperAKAP-IS sequence (SEQ ID NO:7), exhibiting a five order of magnitude higher selectivity for the RII isoform of PKA compared with the RI isoform. Underlined residues indicate the positions of amino acid substitutions, relative to the AKAP-IS sequence, that increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare vaccine constructs. Other alternative sequences that might be substituted for the AKAP-IS AD sequence are shown in SEQ ID NO:8-10. Substitutions relative to the AKAP-IS sequence are underlined. It is anticipated that, as with the AKAP-IS sequence shown in SEQ ID NO:3, the AD moiety may also include the additional N-terminal residues cysteine and glycine and C-terminal residues glycine and cysteine, as shown in SEQ ID NO:4.

SuperAKAP-IS

```
QIEYVAKQIVDYAIHQA      (SEQ ID NO: 7)
```

Alternative AKAP Sequences

```
QIEYKAKQIVDHAIHQA      (SEQ ID NO: 8)

QIEYHAKQIVDHAIHQA      (SEQ ID NO: 9)

QIEYVAKQIVDHAIHQA      (SEQ ID NO: 10)
```

Stokka et al. (2006) also developed peptide competitors of AKAP binding to PKA, shown in SEQ ID NO:11-13. The peptide antagonists were designated as Ht31 (SEQ ID NO:11), RIAD (SEQ ID NO:12) and PV-38 (SEQ ID NO:13). The Ht-31 peptide exhibited a greater affinity for the RII isoform of PKA, while the RIAD and PV-38 showed higher affinity for RI.

```
Ht31    DLIEEAASRIVDAVIEQVKAAGAY   (SEQ ID NO: 11)

RIAD    LEQYANQLADQIIKEATE         (SEQ ID NO: 12)

PV-38   FEELAWKIAKMIWSDVFQQC       (SEQ ID NO: 13)
```

Hundsrucker et al. (2006) developed still other peptide competitors for AKAP binding to PKA, with a binding constant as low as 0.4 nM to the DDD of the RII form of PKA. The sequences of various AKAP antagonistic peptides is provided in Table 1 of Hundsrucker et al. (incorporated herein by reference). Residues that were highly conserved among the AD domains of different AKAP proteins are indicated below by underlining with reference to the AKAP IS sequence (SEQ ID NO:3). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence are shown in SEQ ID NO:14-16.

```
AKAP-IS
QIEYLAKQIVDNAIQQA              (SEQ ID NO: 3)

AKAP7δ-wt-pep
PEDAELVRLSKRLVENAVLKAVQQY      (SEQ ID NO: 14)

AKAP7δ-L304T-pep
PEDAELVRTSKRLVENAVLKAVQQY      (SEQ ID NO: 15)

AKAP7δ-L308D-pep
PEDAELVRLSKRDVENAVLKAVQQY      (SEQ ID NO: 16)
```

Can et al. (2001) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:1. Residues that were particularly conserved are further indicated by italics. The residues overlap with, but are not identical to those suggested by Kinderman et al. (2006) to be important for binding to AKAP proteins. Thus, a potential DDD sequence is indicated in SEQ ID NO:17, wherein "X" represents a conservative amino acid substitution.

```
                                               (SEQ ID NO: 1)
SHIQIPPGLTELLQGYTVEVLRQQPPDLVEFAVEYFTRLREARA
```

```
                                               (SEQ ID NO: 17)
XHIXIPXGLXELLQGYTXEVLRXQPXDLVEFAXXYFXXLXEXRX
```

The skilled artisan will realize that in general, those amino acid residues that are highly conserved in the DDD and AD sequences from different proteins are ones that it may be preferred to remain constant in making amino acid substitutions, while residues that are less highly conserved may be more easily varied to produce sequence variants of the AD and/or DDD sequences described herein.

In addition to sequence variants of the DDD and/or AD moieties, in certain embodiments it may be preferred to introduce sequence variations in the antibody moiety or the linker peptide sequence joining the antibody with the AD sequence. In one illustrative example, three possible variants of fusion protein sequences, are shown in SEQ ID NO:18-20.

```
(L)   QKSLSLSPGLGSGGGGSGGCG    (SEQ ID NO: 18)

(A)   QKSLSLSPGAGSGGGGSGGCG    (SEQ ID NO: 19)

(-)   QKSLSLSPGGSGGGGSGGCG     (SEQ ID NO: 20)
```

Antibodies

In certain embodiments, an antibody or antigen binding fragment thereof may be incorporated into an anti-cancer vaccine. In preferred embodiments, the antibody binds to a tumor associated antigen (TAA) or a DC-associated antigen. As discussed above variety of tumor-associated antigens and/ or DC-associated antigens are known in the art, and antibodies against any such known antigens may be used.

In other embodiments, antibodies that have a direct therapeutic effect on cancer cells may be used as an adjunct therapy to an anti-cancer vaccine. Exemplary anti-cancer antibodies that may be utilized include, but are not limited to, hR1 (anti-IGF-1R, U.S. patent application Ser. No. 12/722,645, filed Mar. 12, 2010) hPAM4 (anti-mucin, U.S. Pat. No. 7,282,567), hA20 (anti-CD20, U.S. Pat. No. 7,251,164), hA19 (anti-CD19, U.S. Pat. No. 7,109,304), hIMMU31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEA, U.S. Pat. No. 6,676,924), hMN-15 (anti-CEA, U.S. Pat. No. 7,541,440), hRS7 (anti-EGP-1, U.S. Pat. No. 7,238,785) and hMN-3 (anti-CEA, U.S. Pat. No. 7,541,440) the Examples section of each cited patent or application incorporated herein by reference. The skilled artisan will realize that this list is not limiting and that any other known anti-cancer antibody may be used.

In other embodiments, antigen-binding antibody fragments may be utilized. Antigen-binding antibody fragments are well known in the art, such as $F(ab')_2$, $F(ab)_2$, Fab', Fab, Fv, scFv and the like. As used herein, an antigen-binding antibody fragment refers to any fragment of an antibody that binds with the same antigen that is recognized by the intact or parent antibody.

An antibody or fragment thereof which is not conjugated to a therapeutic agent is referred to as a "naked" antibody or fragment. Such naked antibodies are of use for cancer therapy. In alternative embodiments, antibodies or fragments may be conjugated to one or more therapeutic. A wide variety of such therapeutic are known in the art, as discussed in more detail below, and any such known therapeutic agent may be used either conjugated to an appropriate antibody or unconjugated and administered before, simultaneously with, or after an anti-cancer antibody and/or vaccine.

Techniques for preparing monoclonal antibodies against virtually any target antigen are well known in the art. See, for example, Kohler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art. The use of antibody components derived from humanized, chimeric or human antibodies obviates potential problems associated with the immunogenicity of murine constant regions.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., *Proc. Nat'l Acad. Sci. USA* 86: 3833 (1989). Techniques for constructing chimeric antibodies are well known to those of skill in the art. As an example, Leung et al., *Hybridoma* 13:469 (1994), produced an LL2 chimera by combining DNA sequences encoding the $V_\kappa$ and $N_H$ domains of murine LL2, an anti-CD22 monoclonal antibody, with respective human κ and $IgG_1$ constant region domains.

Humanized Antibodies

Techniques for producing humanized MAbs are well known in the art (see, e.g., Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). Generally, those human FR amino acid residues that differ from their murine counterparts and are located close to or touching one or more CDR amino acid residues would be candidates for substitution.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50). A fully human antibody also can be constructed by genetic or chromosomal transfection methods, as well as phage display technology, all of which are known in the art. See for example, McCafferty et al., *Nature* 348:552-553 (1990). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), $1^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art (see, e.g., Pasqualini and Ruoslahti, 1996, Nature 380:364-366; Pasqualini, 1999, The Quart. J. Nucl. Med. 43:159-162).

Phage display can be performed in a variety of formats, for their review, see e.g. Johnson and Chiswell, *Current Opinion in Structural Biology* 3:5564-571 (1993). Human antibodies may also be generated by in vitro activated B-cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XenoMouse® (e.g., Green et al., 1999, *J. Immunol. Methods* 231:11-23) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B-cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Antibody Fragments

Antibody fragments which recognize specific epitopes can be generated by known techniques. Antibody fragments are antigen binding portions of an antibody, such as $F(ab')_2$, Fab', $F(ab)_2$, Fab, Fv, sFv and the like. $F(ab')_2$ fragments can be produced by pepsin digestion of the antibody molecule and Fab' fragments can be generated by reducing disulfide bridges of the $F(ab')_2$ fragments. Alternatively, Fab' expression libraries can be constructed (Huse et al., 1989, *Science,* 246:1274-1281) to allow rapid and easy identification of monoclonal Fab' fragments with the desired specificity. $F(ab)_2$ fragments may be generated by papain digestion of an antibody and Fab fragments obtained by disulfide reduction.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are described in U.S. Pat. No. 4,704,692, U.S. Pat. No. 4,946,778, R. Raag and M. Whitlow, "*Single Chain Fvs*." FASEB Vol 9:73-80 (1995) and R. E. Bird and B. W. Walker, "*Single Chain Antibody Variable Regions*," TIBTECH, Vol 9: 132-137 (1991).

Techniques for producing single domain antibodies (DABs) are also known in the art, as disclosed for example in Cossins et al. (2006, Prot Express Purif 51:253-259), incorporated herein by reference.

An antibody fragment can be prepared by proteolytic hydrolysis of the full length antibody or by expression in *E. coli* or another host of the DNA coding for the fragment. An antibody fragment can be obtained by pepsin or papain digestion of full length antibodies by conventional methods. These methods are described, for example, by Goldenberg, U.S. Pat. Nos. 4,036,945 and 4,331,647 and references contained therein. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Known Antibodies

Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312, 318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,15; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856;

6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Amino Acid Substitutions

In certain embodiments, the disclosed methods and compositions may involve production and use of proteins or peptides with one or more substituted amino acid residues. In a non-limiting example, the DDD and/or AD sequences used to make the vaccine constructs may be further optimized, for example to increase the DDD-AD binding affinity.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157:105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gin, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Therapeutic Agents

In various embodiments, therapeutic agents such as cytotoxic agents, anti-angiogenic agents, pro-apoptotic agents, antibiotics, hormones, hormone antagonists, chemokines, drugs, prodrugs, toxins, enzymes, radionuclides or other agents may be used as adjunct therapies to the vaccine constructs described herein. Drugs of use may possess a pharmaceutical property selected from the group consisting of anti-mitotic, antikinase, alkylating, antimetabolite, antibiotic, alkaloid, anti-angiogenic, pro-apoptotic agents and combinations thereof.

Exemplary drugs of use may include 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosurea, plicomycin, procarbazine, paclitaxel, pentostatin, PSI-341, raloxifene, semustine, streptozocin, tamoxifen, taxol, temazolomide (an aqueous form of DTIC), transplatinum, thalidomide, thioguanine, thiotepa, teniposide, topotecan, uracil mustard, vinorelbine, vinblastine, vincristine and vinca alkaloids.

Toxins of use may include ricin, abrin, alpha toxin, saporin, ribonuclease (RNase), e.g., onconase, DNase I, *Staphylococcal* enterotoxin-A, pokeweed antiviral protein, gelonin, diphtheria toxin, *Pseudomonas* exotoxin, and *Pseudomonas* endotoxin.

Radionuclides of use include, but are not limited to, $^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, 143Pr, $^{149}$Pm, $^{169}$Er, $^{194}$Ir, $^{198}$Au, $^{199}$Au, and $^{211}$Pb. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe $^{75}$Se, $^{201}$Tl, $^{225}$Ac, $^{76}$Br, $^{169}$Yb, and the like. Some useful diagnostic nuclides may include $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94}$Tc, $^{94m}$Tc, $^{99m}$Tc, or $^{111}$In.

Therapeutic agents may include a photoactive agent or dye. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Joni et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photo-activated dyes for achieving phototherapy. See Mew et al., J. Immunol. (1983), 130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529.

Other useful therapeutic agents may comprise oligonucleotides, especially antisense oligonucleotides that preferably are directed against oncogenes and oncogene products, such as bcl-2 or p53. A preferred form of therapeutic oligonucleotide is siRNA.

In certain preferred embodiments, the therapeutic agent is an immunomodulator. An immunomodulator is an agent that when present, alters, suppresses or stimulates the body's immune system. Such agents may be particularly useful in conjunction with vaccines to further modulate immune system function. Immunomodulators of use may include a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β or -γ, and stem cell growth factor, such as that designated "S1 factor".

In more preferred embodiments, the effector moieties are cytokines, such as lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); placenta growth factor (P1GF), hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor (TNF, such as TNF-α) and LT. In a particularly preferred embodiment, the cytokine is IFN-α2b.

The amino acid sequences of protein or peptide immunomodulators, such as cytokines, are well known in the art and any such known sequences may be used in the practice of the instant invention. The skilled artisan is aware of numerous sources of public information on cytokine sequence. For example, the NCBI database contains both protein and encoding nucleic acid sequences for a large number of cytokines and immunomodulators, such as erythropoietin (GenBank NM 000799), IL-1 beta (GenPept AAH08678), GM-CSF (GenPept AAA52578), TNF-α (GenPept CAA26669), interferon-alpha (GenPept AAA52716.1), interferon-alpha 2b (GenPept AAP20099.1) and virtually any of the peptide or protein immunomodulators listed above. It is a matter of routine for the skilled artisan to identify an appropriate amino acid and/or nucleic acid sequence for essentially any protein or peptide effector moiety of interest. Commercial sources of cytokines are also available and may be used, such as the full-length human IFN-α2b cDNA clone (Invitrogen Ultimate ORF human clone cat# HORF01Clone ID IOH35221).

Chemokines of use may include RANTES, MCAF, MIP1-alpha, MIP1-Beta and IP-10.

In certain embodiments, anti-angiogenic agents, such as angiostatin, baculostatin, canstatin, maspin, anti-VEGF antibodies, anti-P1GF peptides and antibodies, anti-vascular growth factor antibodies, anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide (roquinimex), thalidomide, pentoxifylline, genistein, TNP-470, endostatin, paclitaxel, accutin, angiostatin, cidofovir, vincristine, bleomycin, AGM-1470, platelet factor 4 or minocycline may be of use.

Conjugation Techniques

In certain embodiments, the antibody or vaccine construct may be conjugated to one or more therapeutic agents. For example, $^{131}$I can be incorporated into a tyrosine of a protein or peptide, or a drug attached to an epsilon amino group of a lysine residue. Therapeutic agents also can be attached, for example to reduced SH groups. Many methods for making covalent or non-covalent conjugates of therapeutic agents with proteins or peptides are known in the art and any such known method may be utilized.

A therapeutic agent can be attached using a heterobifunctional cross-linker, such as N-succinyl 3-(2-pyridyldithio) propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995).

In some embodiments, a chelating agent may be attached to a protein or peptide and used to chelate a therapeutic agent, such as a radionuclide. Exemplary chelators include but are not limited to DTPA (such as Mx-DTPA), DOTA, TETA, NETA or NOTA. Methods of conjugation and use of chelating agents to attach metals or other ligands to proteins or peptides are well known in the art (see, e.g., U.S. Pat. No. 7,563,433, the Examples section of which is incorporated herein by reference). Particularly useful metal-chelate combinations include 2-benzyl-DTPA and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{64}$Cu, $^{18}$F, $^{111}$In, $^{67}$Ga, $^{68}$Ga, $^{99m}$Tc, $^{94m}$Tc, $^{11}$C, $^{13}$N, $^{15}$O or $^{76}$Br for radioimaging. The same chelates, when complexed with non-radioactive metals, such as manganese, iron and gadolinium are useful for MRI. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed.

In certain embodiments, radioactive metals or paramagnetic ions may be attached to proteins or peptides by reaction with a reagent having a long tail, to which may be attached a multiplicity of chelating groups for binding ions. Such a tail can be a polymer such as a polylysine, polysaccharide, or other derivatized or derivatizable chains having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose.

A therapeutic agent can be attached at the hinge region of a reduced antibody component via disulfide bond formation. Alternatively, the therapeutic agent can be conjugated via a carbohydrate moiety in the Fc region of the antibody. The carbohydrate group can be used to increase the loading of the same agent that is bound to a thiol group, or the carbohydrate moiety can be used to bind a different therapeutic agent.

Methods for conjugating peptides to antibody components via an antibody carbohydrate moiety are well-known to those of skill in the art. See, for example, Shih et al., Int. J. Cancer 41:832 (1988); Shih et al., Int. J. Cancer 46:1101 (1990); and Shih et al., U.S. Pat. No. 5,057,313, incorporated herein in their entirety by reference. The general method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody used as the antibody component of the immunoconjugate is an antibody fragment. However, it is possible to introduce a carbohydrate moiety into the light chain variable region of a full length antibody or antibody fragment. See, for example, Leung et al., J. Immunol. 154:5919 (1995); Hansen et al., U.S. Pat. No. 5,443,953 (1995), Leung et al., U.S. Pat. No. 6,254,868, incorporated herein by reference in their entirety. The engineered carbohydrate moiety is used to attach the therapeutic agent.

Methods of Therapeutic Treatment

Various embodiments concern methods of treating a cancer in a subject, such as a mammal, including humans, domestic or companion pets, such as dogs and cats, comprising administering to the subject a therapeutically effective amount of a vaccine construct. The administration of vaccine construct can be supplemented by administering concurrently or sequentially a therapeutically effective amount of an antibody that binds to or is reactive with an antigen on the surface of the target cell as discussed above.

The vaccine construct therapy can be further supplemented with the administration, either concurrently or sequentially, of at least one therapeutic agent. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., Eur. J. Haematol. 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate, bendamustine, and bryostatin-1.

The vaccine construct can be formulated according to known methods to prepare pharmaceutically useful compositions, whereby the vaccine construct is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The vaccine construct can be formulated for intravenous administration via, for example, bolus injection or continuous infusion. Preferably, vaccine construct is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the vaccine construct. Control release preparations can be prepared through the use of polymers to complex or adsorb the vaccine construct. For example, biocompatible polymers include matrices of poly (ethylene-co-vinyl acetate) and matrices of a polyanhydride copolymer of a stearic acid dimer and sebacic acid. Sherwood et al., Bio/Technology 10: 1446 (1992). The rate of release from such a matrix depends upon the molecular weight of the vaccine construct, the amount of vaccine construct within the matrix, and the size of dispersed particles. Saltzman et al., Biophys. J. 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The vaccine construct may also be administered to a mammal subcutaneously or even by other parenteral routes. Moreover, the administration may be by continuous infusion or by single or multiple boluses. Preferably, the vaccine construct is infused over a period of less than about 4 hours, and more preferably, over a period of less than about 3 hours.

More generally, the dosage of an administered vaccine construct for humans will vary depending upon such factors as the patient's age, weight, height, sex, general medical condition and previous medical history. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy. Alternatively, a vaccine construct may be administered as one dosage every 2 or 3 weeks, repeated for a total of at least 3 dosages. Or, the construct may be administered twice per week for 4-6 weeks. The dosing schedule can optionally be repeated at other intervals and dosage may be given through various parenteral routes, with appropriate adjustment of the dose and schedule.

In preferred embodiments, the vaccine constructs are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W.B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Kits

Various embodiments may concern kits containing components suitable for treating a disease in a patient. Exemplary kits may contain at least one or more vaccine constructs as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used. In certain embodiments, a therapeutic agent may be provided in the form of a prefilled syringe or autoinjection pen containing a sterile, liquid formulation or lyophilized preparation.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

Expression Vectors

Still other embodiments may concern DNA sequences comprising a nucleic acid encoding an anti-cancer vaccine construct, or its constituent fusion proteins. Fusion proteins may comprise an anti-CD74 antibody or CD20 xenoantigen attached to a different peptide or protein, such as the AD and DDD peptides utilized for DNL construct formation as discussed in more detail in the Examples below. Alternatively the encoded fusion proteins may comprise a DDD or AD moiety attached to a different antibody or xenoantigen.

Various embodiments relate to expression vectors comprising the coding DNA sequences. The vectors may contain sequences encoding the light and heavy chain constant regions and the hinge region of a human immunoglobulin to which may be attached chimeric, humanized or human variable region sequences. The vectors may additionally contain promoters that express the encoded protein(s) in a selected host cell, enhancers and signal or leader sequences. Vectors that are particularly useful are pdHL2 or GS. More preferably, the light and heavy chain constant regions and hinge region may be from a human EU myeloma immunoglobulin, where optionally at least one of the amino acid in the allotype positions is changed to that found in a different IgG1 allotype, and wherein optionally amino acid 253 of the heavy chain of EU based on the EU number system may be replaced with alanine. See Edelman et al., *Proc. Natl. Acad. Sci. USA* 63:78-85 (1969). In other embodiments, an IgG1 sequence may be converted to an IgG4 sequence.

The skilled artisan will realize that methods of genetically engineering expression constructs and insertion into host cells to express engineered proteins are well known in the art and a matter of routine experimentation. Host cells and methods of expression of cloned antibodies or fragments have been described, for example, in U.S. Pat. Nos. 7,531,327; 7,537,930 and 7,608,425, the Examples section of each incorporated herein by reference.

EXAMPLES

The following examples are provided to illustrate, but not to limit, the claims of the present invention.

Example 1

Preparation of Dock-and-Lock (DNL) Constructs

Exemplary DNL-vaccine constructs may be formed by combining, for example, an Fab-DDD fusion protein of an anti-CD74 antibody with a CD20-AD fusion protein. Alternatively, constructs may be made that combine IgG-AD fusion proteins with CD20-DDD fusion proteins. The technique is not limiting and any protein or peptide of use may be produced as an AD or DDD fusion protein for incorporation into a DNL construct. Where chemical cross-linking is utilized, the AD and DDD conjugates are not limited to proteins or peptides and may comprise any molecule that may be cross-linked to an AD or DDD sequence using any cross-linking technique known in the art.

Independent transgenic cell lines may be developed for each DDD or AD fusion protein. Once produced, the modules can be purified if desired or maintained in the cell culture supernatant fluid. Following production, any DDD-fusion protein module can be combined with any AD-fusion protein module to generate a DNL construct. For different types of constructs, different AD or DDD sequences may be utilized. Exemplary DDD and AD sequences are discussed above.

Expression Vectors

The plasmid vector pdHL2 has been used to produce a number of antibodies and antibody-based constructs. See Gillies et al., J Immunol Methods (1989), 125:191-202; Losman et al., Cancer (Phila) (1997), 80:2660-6. The di-cistronic mammalian expression vector directs the synthesis of the heavy and light chains of IgG. The vector sequences are mostly identical for many different IgG-pdHL2 constructs, with the only differences existing in the variable domain (VH and VL) sequences. Using molecular biology tools known to those skilled in the art, these IgG expression vectors can be converted into Fab-DDD or Fab-AD expression vectors. To generate Fab-DDD expression vectors, the coding sequences for the hinge, CH2 and CH3 domains of the heavy chain are replaced with a sequence encoding the first 4 residues of the hinge, a 14 residue Gly-Ser linker and the first 44 residues of human RIIα (referred to as DDD1). To generate Fab-AD expression vectors, the sequences for the hinge, CH2 and CH3 domains of IgG are replaced with a sequence encoding the first 4 residues of the hinge, a 15 residue Gly-Ser linker and a 17 residue synthetic AD called AKAP-IS (referred to as AD 1), which was generated using bioinformatics and peptide array technology and shown to bind RIIα dimers with a very high affinity (0.4 nM). See Alto, et al. Proc. Natl. Acad. Sci., U.S.A (2003), 100:4445-50. Two shuttle vectors were designed to facilitate the conversion of IgG-pdHL2 vectors to either Fab-DDD1 or Fab-AD1 expression vectors, as described below.

Preparation of CH1

The CH1 domain was amplified by PCR using the pdHL2 plasmid vector as a template. The left PCR primer consisted of the upstream (5') end of the CH1 domain and a SacII restriction endonuclease site, which is 5' of the CH1 coding sequence. The right primer consisted of the sequence coding for the first 4 residues of the hinge (PKSC (SEQ ID NO:21)) followed by four glycines and a serine, with the final two codons (GS) comprising a Bam HI restriction site. The 410 bp PCR amplimer was cloned into the PGEMT® PCR cloning vector (PROMEGA®, Inc.) and clones were screened for inserts in the T7 (5') orientation.

Construction of (G₄S)₂DDD1 ((G₄S)₂ Disclosed as SEQ ID NO:22)

A duplex oligonucleotide, designated (G₄S)₂DDD1 ((G₄S)₂ disclosed as SEQ ID NO:22), was synthesized by Sigma GENOSYS® (Haverhill, UK) to code for the amino acid sequence of DDD1 preceded by 11 residues of the linker peptide, with the first two codons comprising a BamHI restriction site. A stop codon and an EagI restriction site are appended to the 3' end. The encoded polypeptide sequence is shown below.

(SEQ ID NO: 23)
GSGGGGSGGGGSHIQIPPGLTELLQGYTVEVLRQQPPDLVEFAVEYFTRL

REARA

Two oligonucleotides, designated RIIA1-44 top and RIIA1-44 bottom, that overlap by 30 base pairs on their 3' ends, were synthesized (Sigma GENOSYS®) and combined to comprise the central 154 base pairs of the 174 bp DDD1 sequence. The oligonucleotides were annealed and subjected to a primer extension reaction with Taq polymerase. Following primer extension, the duplex was amplified by PCR. The amplimer was cloned into PGEMT® and screened for inserts in the T7 (5') orientation.

Construction of (G₄S)-2-AD1 ((G₄S)₂ Disclosed as SEQ ID NO:22)

A duplex oligonucleotide, designated (G₄S)-2-AD1 ((G₄S)₂ disclosed as SEQ ID NO:22), was synthesized (Sigma GENOSYS®) to code for the amino acid sequence of AD1 preceded by 11 residues of the linker peptide with the first two codons comprising a BamHI restriction site. A stop codon and an EagI restriction site are appended to the 3' end. The encoded polypeptide sequence is shown below.

GSGGGGSGGGGSQIEYLAKQIVDNAIQQA (SEQ ID NO: 24)

Two complimentary overlapping oligonucleotides encoding the above peptide sequence, designated AKAP-IS Top and AKAP-IS Bottom, were synthesized and annealed. The duplex was amplified by PCR. The amplimer was cloned into the PGEMT® vector and screened for inserts in the T7 (5') orientation.

Ligating DDD1 with CH1

A 190 bp fragment encoding the DDD1 sequence was excised from PGEMT® with BamHI and NotI restriction enzymes and then ligated into the same sites in CH1-PGEMT® to generate the shuttle vector CH1-DDD1-PGEMT®.

Ligating AD1 with CH1

A 110 bp fragment containing the AD1 sequence was excised from PGEMT® with BamHI and NotI and then ligated into the same sites in CH1-PGEMT® to generate the shuttle vector CH1-AD1-PGEMT®.

Cloning CH1-DDD1 or CH1-AD1 into pdHL2-based vectors

With this modular design either CH1-DDD1 or CH1-AD1 can be incorporated into any IgG construct in the pdHL2 vector. The entire heavy chain constant domain is replaced with one of the above constructs by removing the SacII/EagI restriction fragment (CH1-CH3) from pdHL2 and replacing it with the SacII/EagI fragment of CH1-DDD1 or CH1-AD1, which is excised from the respective pGemT shuttle vector.

Construction of h679-Fd-AD1-pdHL2 h679-Fd-AD1-pdHL2 is an expression vector for production of h679 Fab with AD1 coupled to the carboxyl terminal end of the CH1 domain of the Fd via a flexible Gly/Ser peptide spacer composed of 14 amino acid residues. A pdHL2-based vector containing the variable domains of h679 was converted to h679-Fd-AD1-pdHL2 by replacement of the SacII/EagI fragment with the CH1-AD1 fragment, which was excised from the CH1-AD1-SV3 shuttle vector with SacII and EagI.

Construction of C-DDD1-Fd-hMN-14-pdHL2

C-DDD1-Fd-hMN-14-pdHL2 is an expression vector for production of a stable dimer that comprises two copies of a fusion protein C-DDD1-Fab-hMN-14, in which DDD1 is linked to hMN-14 Fab at the carboxyl terminus of CH1 via a flexible peptide spacer. The plasmid vector hMN-14(I)-pdHL2, which has been used to produce hMN-14 IgG, was converted to C-DDD1-Fd-hMN-14-pdHL2 by digestion with SacII and EagI restriction endonucleases to remove the CH1-CH3 domains and insertion of the CH1-DDD1 fragment, which was excised from the CH1-DDD1-SV3 shuttle vector with SacII and EagI.

The same technique has been utilized to produce plasmids for Fab expression of a wide variety of known antibodies, such as hLL1, hLL2, hPAM4, hR1, hRS7, hMN-14, hMN-15, hA19, hA20 and many others. Generally, the antibody variable region coding sequences were present in a pdHL2 expression vector and the expression vector was converted for production of an AD- or DDD-fusion protein as described above.

Construction of C-DDD2-Fd-hMN-14-pdHL2

C-DDD2-Fd-hMN-14-pdHL2 is an expression vector for production of C-DDD2-Fab-hMN-14, which possesses a dimerization and docking domain sequence of DDD2 appended to the carboxyl terminus of the Fd of hMN-14 via a 14 amino acid residue Gly/Ser peptide linker. The fusion protein secreted is composed of two identical copies of hMN-14 Fab held together by non-covalent interaction of the DDD2 domains.

The expression vector was engineered as follows. Two overlapping, complimentary oligonucleotides, which comprise the coding sequence for part of the linker peptide (GGGGSGGGCG, SEQ ID NO:25) and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

The duplex DNA was ligated with the shuttle vector CH1-DDD1-PGEMT®, which was prepared by digestion with BamHI and PstI, to generate the shuttle vector CH1-DDD2-PGEMT®. A 507 bp fragment was excised from CH1-DDD2-PGEMT® with SacII and EagI and ligated with the IgG expression vector hMN-14(I)-pdHL2, which was prepared by digestion with SacII and EagI. The final expression construct was designated C-DDD2-Fd-hMN-14-pdHL2. Similar techniques have been utilized to generated DDD2-fusion proteins of the Fab fragments of a number of different humanized antibodies.

Construction of h679-Fd-AD2-pdHL2 h679-Fd-AD2-pdHL2 is an expression vector for the production of h679-Fab-AD2, which possesses an anchoring domain sequence of AD2 appended to the carboxyl terminal end of the CH1 domain via a 14 amino acid residue Gly/Ser peptide linker. AD2 has one cysteine residue preceding and another one following the anchor domain sequence of AD1.

The expression vector was engineered as follows. Two overlapping, complimentary oligonucleotides which comprise the coding sequence for AD2 and part of the linker sequence, were made synthetically. The oligonucleotides were annealed and phosphorylated with T4 PNK, resulting in overhangs on the 5' and 3' ends that are compatible for ligation with DNA digested with the restriction endonucleases BamHI and SpeI, respectively.

The duplex DNA was ligated into the shuttle vector CH1-AD1-PGEMT®, which was prepared by digestion with BamHI and SpeI, to generate the shuttle vector CH1-AD2-PGEMT®. A 429 base pair fragment containing CH1 and AD2 coding sequences was excised from the shuttle vector with SacII and EagI restriction enzymes and ligated into h679-pdHL2 vector that prepared by digestion with those same enzymes. The final expression vector is h679-Fd-AD2-pdHL2.

Generation of TF2 Trimeric DNL Construct

A trimeric DNL construct designated TF2 was obtained by reacting C-DDD2-Fab-hMN-14 with h679-Fab-AD2. A pilot batch of TF2 was generated with >90% yield as follows. Protein L-purified C-DDD2-Fab-hMN-14 (200 mg) was mixed with h679-Fab-AD2 (60 mg) at a 1.4:1 molar ratio. The total protein concentration was 1.5 mg/ml in PBS containing 1 mM EDTA. Subsequent steps involved TCEP reduction, HIC chromatography, DMSO oxidation, and IMP 291 affinity chromatography. Before the addition of TCEP, SE-HPLC did not show any evidence of $a_2b$ formation. Addition of 5 mM TCEP rapidly resulted in the formation of $a_2b$ complex consistent with a 157 kDa protein expected for the binary structure. TF2 was purified to near homogeneity by IMP 291 affinity chromatography (not shown). IMP 291 is a synthetic peptide containing the HSG hapten to which the 679 Fab binds (Rossi et al., 2005, Clin Cancer Res 11:7122s-29s). SE-HPLC analysis of the IMP 291 unbound fraction demonstrated the removal of $a_4$, $a_2$ and free kappa chains from the product (not shown).

Non-reducing SDS-PAGE analysis demonstrated that the majority of TF2 exists as a large, covalent structure with a relative mobility near that of IgG (not shown). Reducing SDS-PAGE shows that any additional bands apparent in the non-reducing gel are product-related (not shown), as only bands representing the constituent polypeptides of TF2 were evident (not shown). However, the relative mobilities of each of the four polypeptides were too close to be resolved. MALDI-TOF mass spectrometry (not shown) revealed a single peak of 156,434 Da, which is within 99.5% of the calculated mass (157,319 Da) of TF2.

The functionality of TF2 was determined by BIACORE® assay. TF2, C-DDD1-hMN-14+h679-AD1 (used as a control sample of noncovalent $a_2b$ complex), or C-DDD2-hMN-14+ h679-AD2 (used as a control sample of unreduced $a_2$ and b components) were diluted to 1 μg/ml (total protein) and passed over a sensorchip immobilized with HSG. The response for TF2 was approximately two-fold that of the two control samples, indicating that only the h679-Fab-AD component in the control samples would bind to and remain on the sensorchip. Subsequent injections of WI2 IgG, an anti-idiotype antibody for hMN-14, demonstrated that only TF2 had a DDD-Fab-hMN-14 component that was tightly associated with h679-Fab-AD as indicated by an additional signal response. The additional increase of response units resulting from the binding of WI2 to TF2 immobilized on the sensorchip corresponded to two fully functional binding sites, each contributed by one subunit of C-DDD2-Fab-hMN-14. This was confirmed by the ability of TF2 to bind two Fab fragments of WI2 (not shown).

Example 2

$C_{H3}$-AD2-IgG Expression Vectors

A plasmid shuttle vector was produced to facilitate the conversion of any IgG-pdHL2 vector into a $C_{H3}$-AD2-IgG-pdHL2 vector. The gene for the Fc ($C_{H2}$ and $C_{H3}$ domains) was amplified by PCR using the pdHL2 vector as a template and the following oligonucleotide primers:

```
Fc BglII Left
AGATCTGGCGCACCTGAACTCCTG            (SEQ ID NO: 26)

Fc Bam-EcoRI Right
GAATTCGGATCCTTTACCCGGAGACAGGGAGAG.  (SEQ ID NO: 27)
```

The amplimer was cloned in the pGemT PCR cloning vector (Promega). The Fc insert fragment was excised from pGemT with Xba I and Bam HI and ligated with AD2-pdHL2 vector that was prepared by digesting h679-Fab-AD2-pdHL2 (Rossi et al., Proc Natl Acad Sci USA 2006, 103:6841-6) with Xba I and Bam HI, to generate the shuttle vector Fc-AD2-pdHL2. To convert IgG-pdHL2 expression vectors to a $C_{H3}$-AD2-IgG-pdHL2 expression vectors, an 861 bp BsrG I/Nde I restriction fragment was excised from the former and replaced with a 952 bp BsrG I/Nde I restriction fragment excised from the Fc-AD2-pdHL2 vector. The following is a partial list of $C_{H3}$-AD2-IgG-pdHL2 expression vectors that have been generated and used for the production of recombinant humanized IgG-AD2 modules:

$C_{H3}$-AD2-IgG-hA20 (anti-CD20)
$C_{H3}$-AD2-IgG-hLL2 (anti-CD22)
$C_{H3}$-AD2-IgG-hL243 (anti-HLA-DR)
$C_{H3}$-AD2-IgG-hLL1 (anti-CD74)
$C_{H3}$-AD2-IgG-hR1 (anti-IGF-1R)
$C_{H3}$-AD2-IgG-h734 (anti-Indium-DTPA).

Example 3

Production of $C_{H3}$-AD2-IgG

Transfection and Selection of Stable $C_{H3}$-AD2-IgG Secreting Cell Lines

All cell lines were grown in Hybridoma SFM (Invitrogen, Carlsbad Calif.). $C_{H3}$-AD2-IgG-pdHL2 vectors (30 μg) were linearized by digestion with Sal I restriction endonuclease and transfected into Sp2/0-Ag14 ($2.8 \times 10^6$ cells) by electroporation (450 volts, 25 μF). The pdHL2 vector contains the gene for dihydrofolate reductase allowing clonal selection as well as gene amplification with methotrexate (MTX).

Following transfection, the cells were plated in 96-well plates and transgenic clones were selected in media containing 0.2 μM MTX. Clones were screened for $C_{H3}$-AD2-IgG productivity by a sandwich ELISA using 96-well microtitre plates coated with specific anti-idiotype MAbs. Conditioned media from the putative clones were transferred to the microplate wells and detection of the fusion protein was accomplished with horseradish peroxidase-conjugated goat anti-human IgG F(ab')$_2$ (Jackson ImmunoResearch Laboratories, West Grove, Pa.). Wells giving the highest signal were expanded and ultimately used for production.

Production and Purification of $C_{H3}$-AD2-IgG Modules

For production of the fusion proteins, roller bottle cultures were seeded at $2 \times 10^5$ cells/ml and incubated in a roller bottle incubator at 37° C. under 5% CO$_2$ until the cell viability dropped below 25% (~10 days). Culture broth was clarified by centrifugation, filtered, and concentrated up to 50-fold by ultrafiltration. For purification of $C_{H3}$-AD2-IgG modules, concentrated supernatant fluid was loaded onto a Protein-A (MAB Select) affinity column. The column was washed to baseline with PBS and the fusion proteins were eluted with 0.1 M Glycine, pH 2.5.

Example 4

Generation of DDD2-mCD20(136-178) and Construction of DDD2-mCD20(136-178)-pdHL2

DDD2-mCD20(136-178)-pdHL2 is the expression vector for DDD2-mCD20(136-178), which comprises DDD2-linker-mCD20(136-178)—HHHHHH (HHHHHH disclosed as SEQ ID NO:28). The extracellular domain of mouse CD20 (mCD20) is referred to as mCD20(136-178), comprising the sequence shown below:

(SEQ ID NO: 29)
TLSHFLKMRRLELIQTSKPYVDIYDCEPSNSSEKNSPSTQYCN

The amino acid sequence of mouse CD20 xenoantigen is shown below.

(SEQ ID NO: 30)
MSGPFPAEPTKGPLAMQPAPKVNLKRTSSLVGPTQSFFMRESKALGA

VQIMNGLFHITLGGLLMIPTGVFAPICLSVWYPLWGGIMYIISGSLLAA

AAEKTSRKSLVKAKVIMSSLSLFAAISGIILSIMDILNMTLSHFLKMRRL

ELIQTSKPYVDIYDCEPSNSSEKNSPSTQYCNSIQSVFLGILSAMLISA

FFQKLVTAGIVENEWKRMCTRSKSNVVLLSAGEKNEQTIKMKEEIIELS

GVSSQPKNEEEIEIIPVQEEEEEAEINFPAPPQEQESLPVENEIAP

The DNA segment comprising the nucleotide sequence of mCD20(136-178) flanked by BamH1 and Xho1 restriction sites is obtained by PCR using a full length murine CD20 cDNA clone as template and the two primers shown below:

```
Upstream primer: BamHI_mCD20
primer (30-mer)
                                  (SEQ ID NO: 31)
5'-GGATCCACACTTTCTCATTTTTTAAAAATG Downstream primer: XhoI mCD20
primer (30-mer)
                                  (SEQ ID NO: 32)
5'-CTCGAGGTTACAGTACTGTGTAGATGGGGA
```

The PCR amplimer (141 bp) is cloned into the PGEMT® vector (PROMEGA®). A DDD2-pdHL2 mammalian expression vector, for example, N-DDD2-hG-CSF-His-pdHL2, is prepared for ligation with the amplimer by digestion with XbaI and Bam HI restriction endonucleases. The mCD20-amplimer is excised from PGEMT® with XbaI and Bam HI and ligated into the DDD2-pdHL2 vector to generate the expression vector DDD2-mCD20(136-178)-pdHL2.

Transfection and Screen to Obtain Clones Expressing DDD2-mCD20(136-178)

The vector DDD2-mCD20(136-178) is linearized by digestion with SalI enzyme and stably transfected into SpESF myeloma cells by electroporation (see, e.g., U.S. Pat. No. 7,537,930, the Examples section of which is incorporated herein by reference). A number of clones are found to have detectable levels of DDD2-mCD20(136-178) by ELISA, from which the best producing clone is selected and subsequently amplified with increasing methotrexate (MTX) concentrations from 0.1 to 0.8 µM over five weeks. At this stage, it is sub-cloned by limiting dilution and the highest producing sub-clone is expanded.

The clone is expanded to 34 roller bottles containing a total of 20 L of serum-free Hybridoma SFM with 0.8 µM MTX and allowed to reach terminal culture. The supernatant fluid is clarified by centrifugation and filtered (0.2 µM). The filtrate is diafiltered into 1× Binding buffer (10 mM imidazole, 0.5 M NaCl, 50 mM NaH$_2$PO$_4$, pH 7.5) and concentrated to 310 mL in preparation for purification by immobilized metal affinity chromatography (IMAC). The concentrate is loaded onto a 30-mL Ni-NTA column, which is washed with 500 mL of 0.02% Tween 20 in 1× binding buffer and then 290 mL of 30 mM imidazole, 0.02% Tween 20, 0.5 M NaCl, 50 mM NaH$_2$PO$_4$, pH 7.5. The product is eluted with 110 mL of 250 mM imidazole, 0.02% Tween 20, 150 mM NaCl, 50 mM NaH$_2$PO$_4$, pH 7.5. The purity of DDD2-mCD20(136-178) is assessed by SDS-PAGE under reducing conditions.

Example 5

Generation of 74-mCD20 DNL Vaccine Comprising hLL1 IgG Linked to Four Copies of mCD20(136-178)

$C_{H3}$-AD2-IgG-hLL1 (anti-CD74) is produced as described in Examples 2 and 3. The construct comprises an AD2 moiety attached to the C-terminal end of each heavy chain of the hLL1 IgG. DDD2-mCD20(136-178) is produced as described in Example 4. A DNL reaction is performed by mixing hLL1 IgG-AD2 and DDD2-mCD20(136-178) in PBS containing 1 mM reduced glutathione. On the next day oxidized glutathione is added to a final concentration of 2 mM and the reaction mixture is purified on a Protein A column 24 h later. In this embodiment, two copies of the DDD2-mCD20 are attached to each AD2 moiety, resulting in a DNL complex comprising one hLL1 IgG moiety and four mCD20 xenoantigen moieties.

In an alternative embodiment, the Fab of hLL1 is linked to DDD2 and the mCD20(136-178) to AD2. Formation of a DNL construct as described above results in the formation of an MM vaccine, designated hLL1-F(ab)-2-mCD20(136-178), which comprises a single mCD20(136-178) attached to two Fab moieties of hLL1. The generation of AD2-mCD20 (136-178) is described in Example 6.

Administration of 74-mCD20(136-178) or hLL1-F(ab)-2-mCD20(136-178) to subjects with MM induces an immune response against CD138$^{neg}$CD20$^+$ putative MM stem cells. The immune response is effective to reduce or eliminate MM disease cells in the subjects.

Example 6

Generation of Recombinant AD2-mCD20(136-178)

AD2-mCD20(136-178)-pdHL2 is the expression vector for recombinant AD2-mCD20(136-178), which comprises AD2-linker-mCD20(136-178)-HHHHHH(HHHHHH disclosed as SEQ ID NO:28). The DNA segment comprising the nucleotide sequence of mCD20(136-178) flanked by Bgl2 and Eag1 restriction sites is obtained by PCR using a full length murine CD20 cDNA clone as template and the two primers shown below:

```
Upstream primer: Bal2_mCD20
primer (30-mer)
                                        (SEQ ID NO: 33)
5'-AGATCTACACTTTCTCATTTTTTAAAAATG Downstream primer: Eag1_mCD20 primer (48-mer)
                                        (SEQ ID NO: 34)
5' CGGCCGTCAGTGGTGGTGGTGGTGGTGGTTACAGTACTGTGTAGAT
GG
```

The PCR amplimer (162 bp) is cloned into the PGEMT® vector (PROMEGA®). An AD2-pdHL2 mammalian expression vector, for example, N-AD2-hTransferrin-His-pdHL2, is prepared for ligation with the amplimer by digestion with Bgl2 and Eag1 restriction endonucleases. The mCD20-amplimer is excised from PGEMT® with Bgl2 and Eag1 and ligated into the AD2-pdHL2 vector to generate the expression vector AD2-mCD20(136-178)-pdHL2. Clones expressing AD2-mCD20(136-178) are obtained as described in Example 4 and AD2-mCD20(136-178) is purified from culture supernatants using Ni-select.

Example 7

Effects of hLL1 on DCs-Efficient Binding of hLL1 with Different Subsets of APCs

Figure 2A:
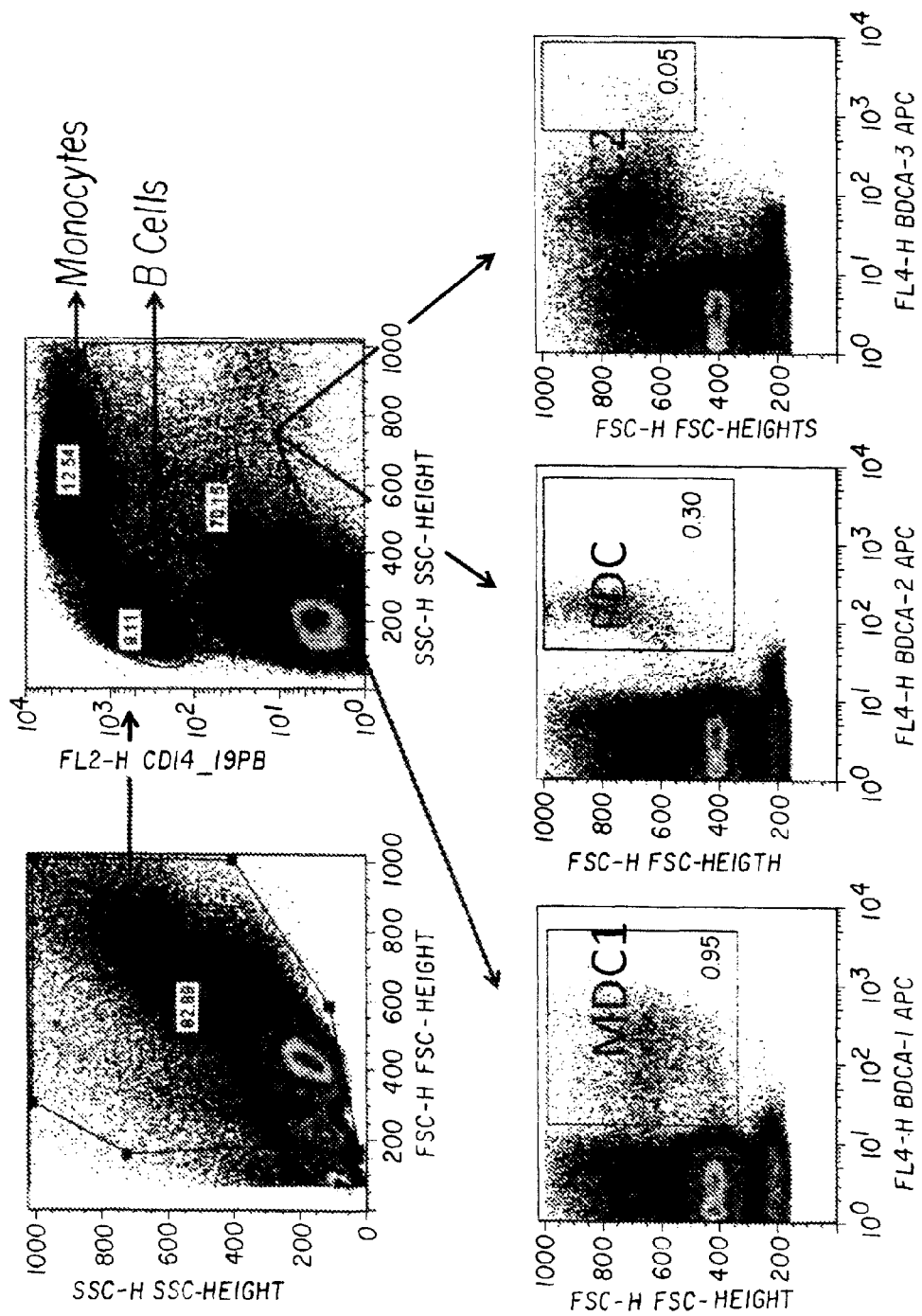
FIG. 2. Specific binding of hLL1 on human blood DC subsets, B cells, and monocytes. (A) The gating strategy for the different APC subsets. (B) CD74 expression in APCs. (C) The binding efficiency of hLL1 on the cells. The numbers represent mean fluorescence intensity.
Figure 2B:
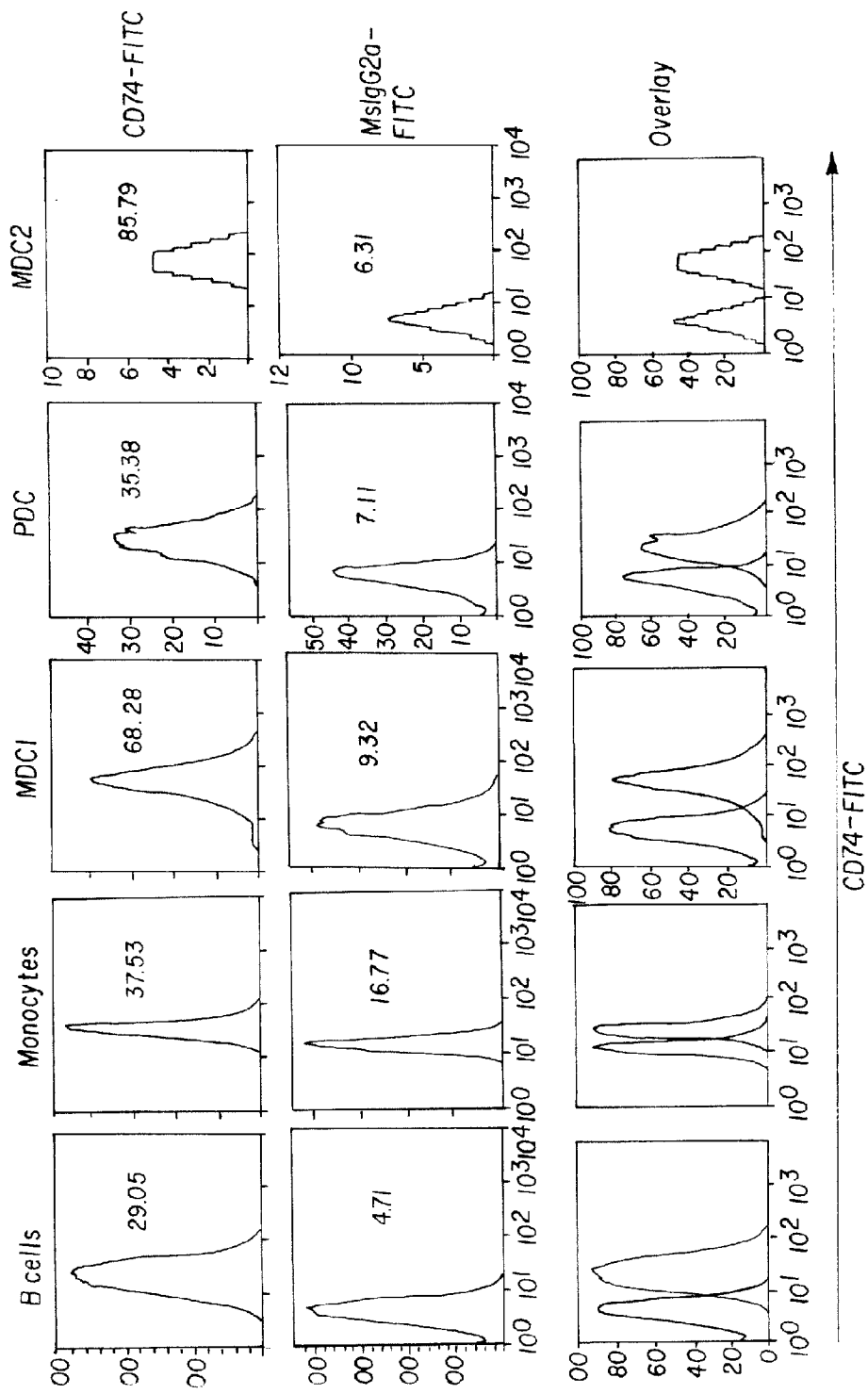
Figure 2C:
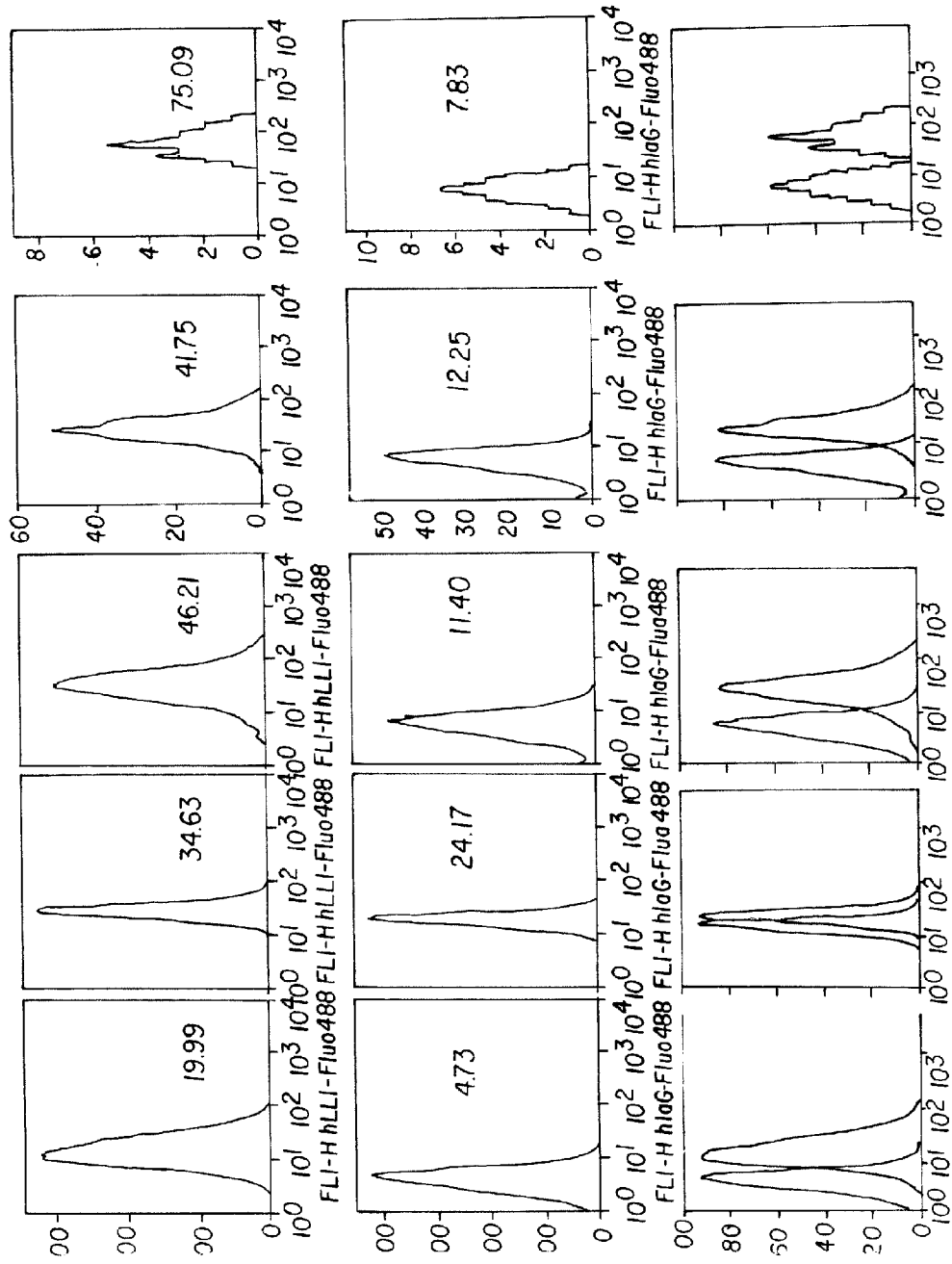
Figure 3A:
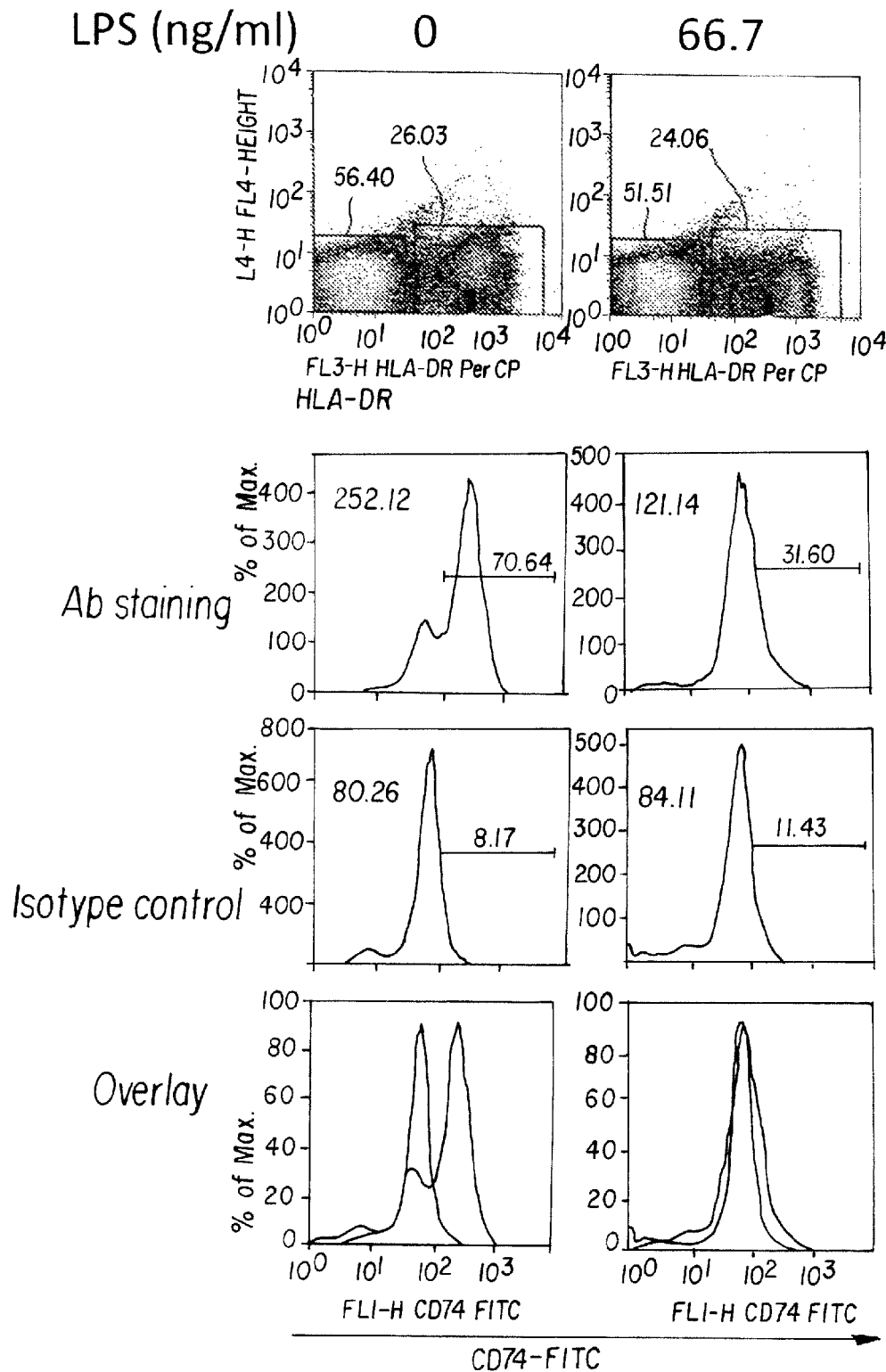
FIG. 3. CD74 expression in and binding efficiency of hLL1 with human monocyte-derived immature vs mature DCs. The human monocyte-derived DCs (day 5 after culture in the presence of hGM-CSF and hIL-4) were stained with FITC-labeled anti-CD74 antibody or AlexaFluor488-labeled hLL1, in combination with the staining with fluorescence-labeled mAbs against HLA-DR and CD83. The HLA-DR-positive cells are gated and analyzed. (A) CD74 expression in immature and LPS-matured DCs. (B) hLL1 binding with immature vs LPS-matured DCs. (C) Comparison of expression of CD83, HLA-DR, CD74 and hLL1 binding in immature and mature DCs.
Figure 3B:
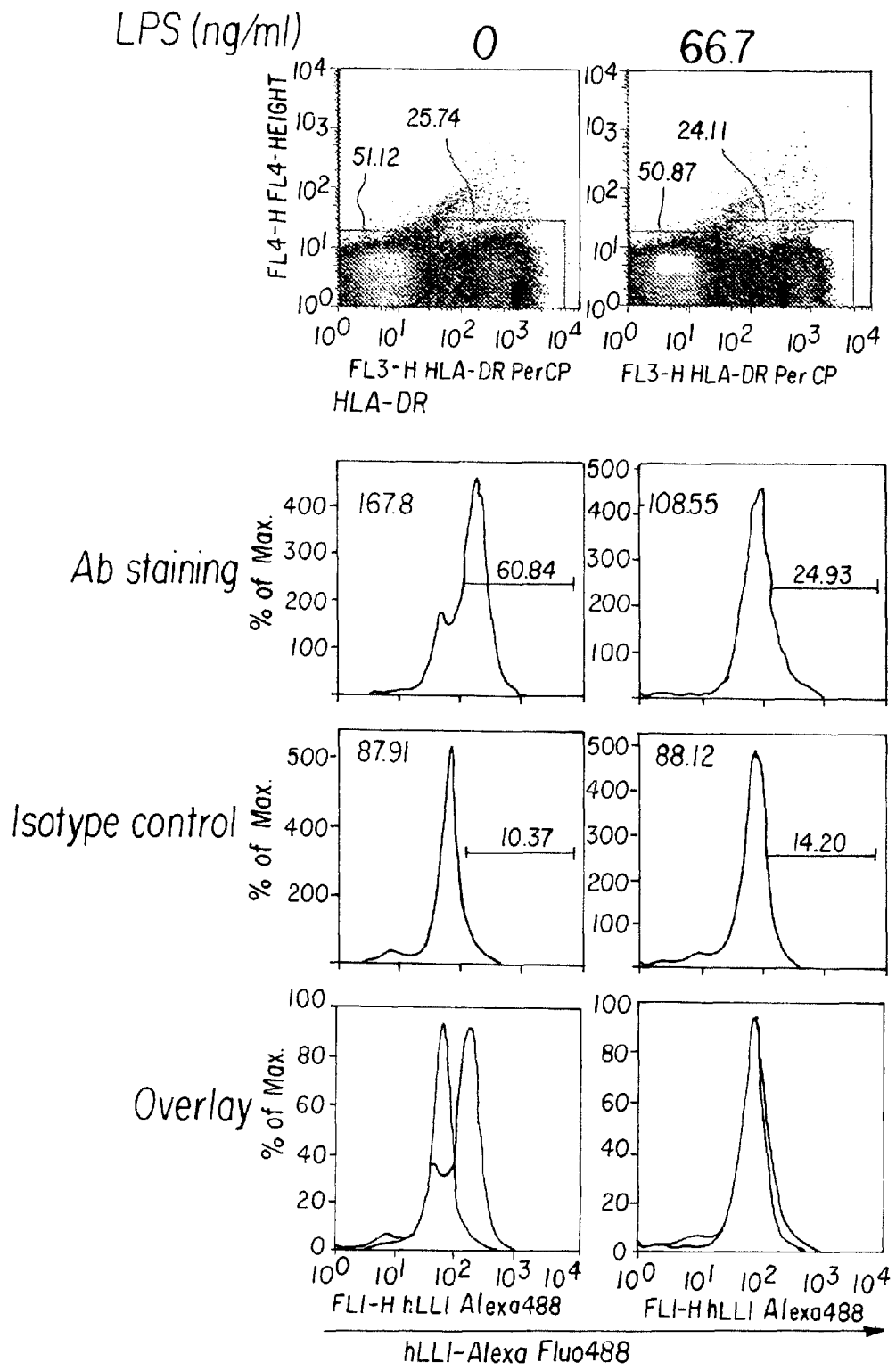
Figure 3C:
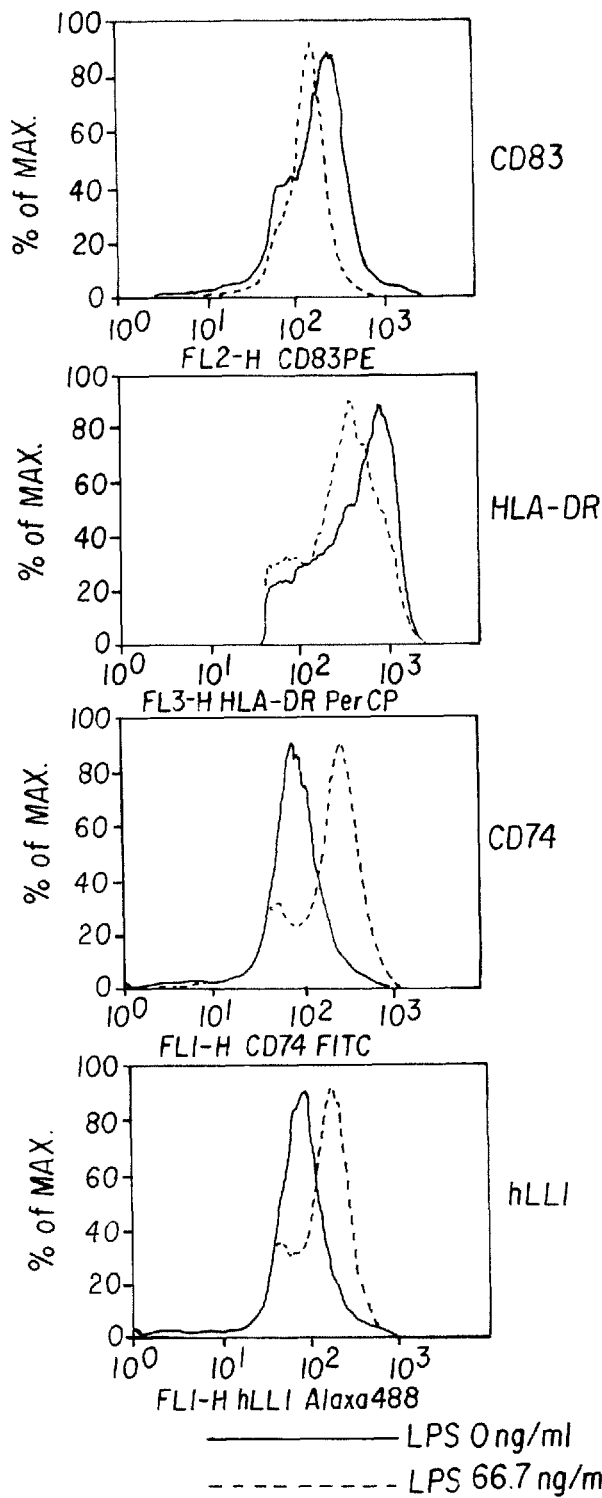

Early studies demonstrated that CD74 is expressed in most antigen-presenting cells including blood DCs, B cells, monocytes. To further characterize the expression profile of CD74 in APCs, we examined the expression of CD74 in different subsets of human PBMCs and in vitro monocyte-derived DCs. Using the gating strategy that is shown in FIG. 2A, we found all of the blood DC subsets, the myeloid DC1 (MDC1) and DC2 (MDC2), and plasmacytoid DC (PDC) expressed CD74, with MDC2 expressing the highest level of CD74 (FIG. 2B). CD74 was also expressed in monocyte-derived immature DCs at much higher level than in LPS-matured DCs (FIG. 3A). Consistent with the CD74 expression profiles, hLL1 bound efficiently with blood DC subsets, B cells, monocytes, and monocyte-derived immature DCs (FIG. 2C, FIG. 3B), but not LPS-matured DCs (FIG. 3B, FIG. 3C). The binding efficiency of hLL1 in these APC subsets correlates well with their CD74 expression levels. These data provide the basis for in vivo targeting of antigen to APCs using hLL1 as the targeting vehicle by Dock-and-lock technology.

Figure 4A:
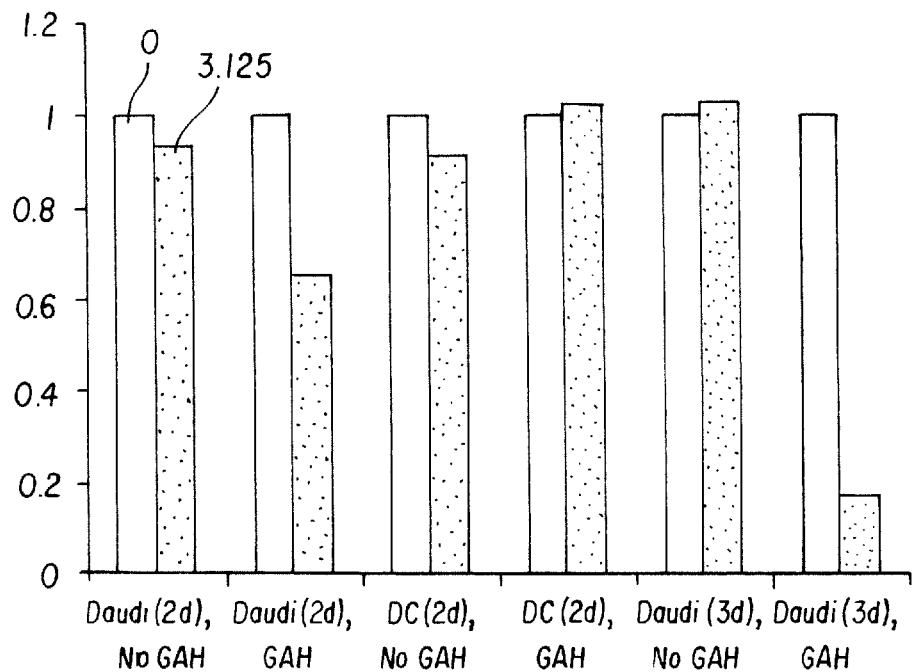
FIG. 4. Side-by-side comparison of the cytotoxic effect of hLL1 on B cell malignant Daudi cells and normal DCs. (A) Comparison of the effect of hLL1 on Daudi and DCs. (B) Effect of hLL1 on cell viability of DCs in an extended doses. (C) The cytotoxic effect of hLL1 on Daudi cells. (D) The microscopic image shows no effect of hLL1 on DC viability.
Figure 4B:
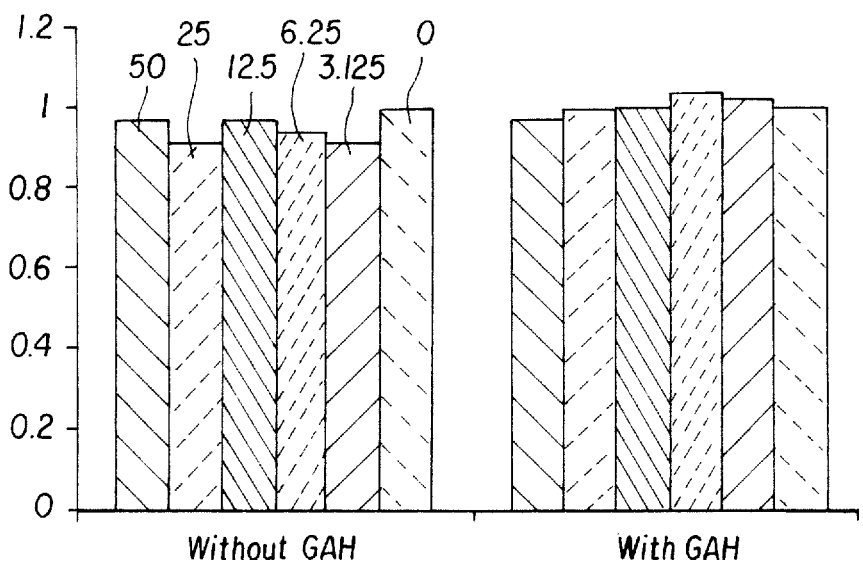
Figure 4C:
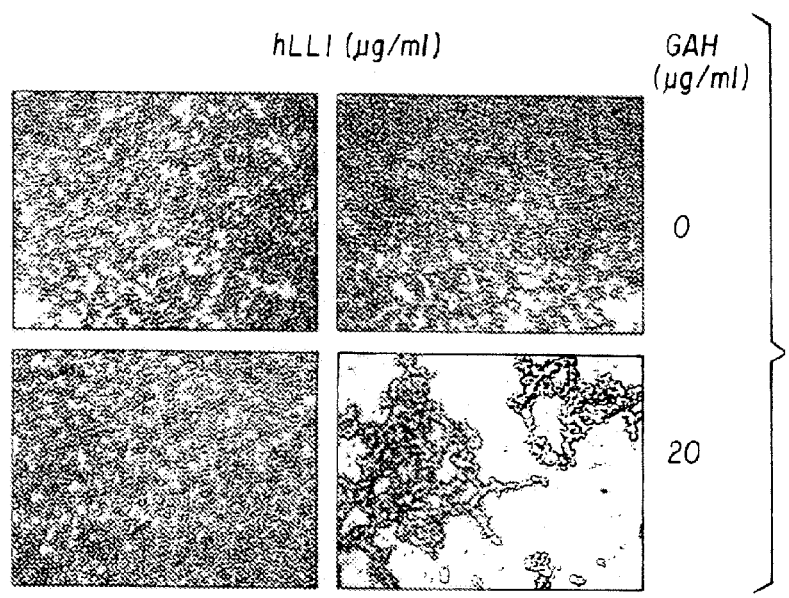
Figure 4D:
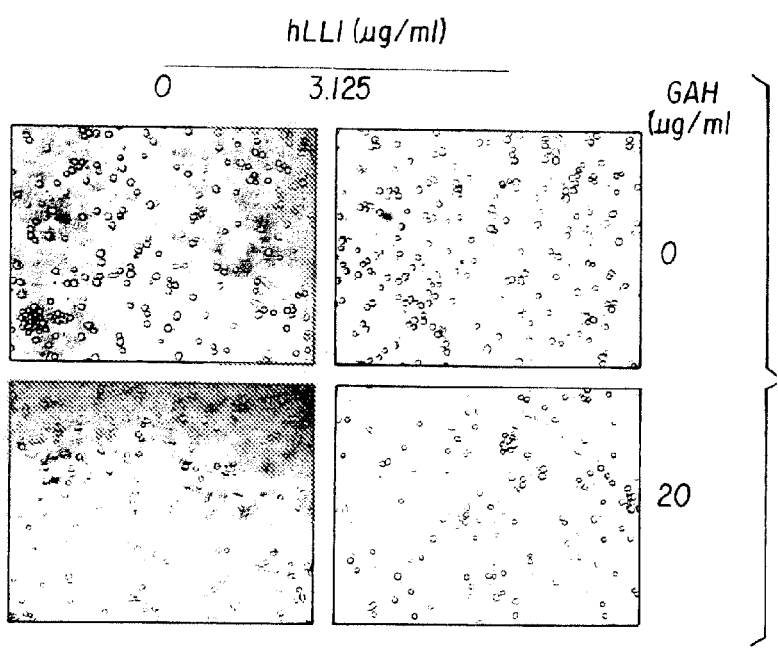

Cytotoxic Effect of hLL1 on CD74-Expressing Malignant B Cells but not on Normal DCs Since CD74 is highly expressed in immature DCs, with which hLL1 binds efficiently, as shown in FIG. 2A and FIG. 2B, we wondered if hLL1 has the same cytotoxicity in DCs, as it does a in CD74-expressing B cell lymphoma, which was shown previously (Stein et al., Blood 2004, 104:3705-11). To this end, the effects of hLL1 on the cell viability of B cell malignancy Daudi cells and human monocyte-derived DCs were side-by-side compared using an MTS assay and microscope imaging. The results demonstrated that hLL1, in the presence of GAH (goat anti-human antibody), the second antibody for hLL1 cross-linking, significantly reduced cell viability of Daudi cells but not DCs (FIG. 4A), which normally expressed high level of CD74 as shown above. The microscopic imaging showed that Daudi cells treated with hLL1 crosslinked with GAH became clumped and condensed, while the DCs maintained normal morphology after the same treatment (FIG. 4C, FIG. 4D). The cytotoxicity against Daudi cells by hLL1 cross-linked with GAH was consistent with the earlier study by Stein et al. (2004) showing that hLL1 was cytotoxic to B cell malignancies in vitro and in vivo. The lack of cytotoxicity of hLL1 plus GAH on DCs was further demonstrated in apoptosis assay, which showed that the hypodiploid nuclei populations were not influenced by hLL1 cross-linked with GAH (not shown).

To further confirm the lack of cytotoxicity of hLL1 on DCs, we performed apoptosis assay using flow cytometry. The nuclei from hLL1 treated immature DCs were obtained and stained with PI for flow cytometry analysis. The PI+ particles were gated first, and the debris was excluded by gating out the SSC-low particles. The resulting gated nuclei were analyzed for apoptosis by measuring hypodiploid nuclei population (FIG. 3A). The results demonstrate that hLL1 had no influence on DC apoptosis in both donors (FIG. 3B, FIG. 3C), in the presence or absence of a second mAb (20 μg/ml) for cross-linking (GAH, F(ab')₂ GAH IgG Fcγ-specific). These data demonstrated that hLL1, unlike its cytotoxic effect on B cell malignancies, has little cytotoxicity against normal dendritic cells which also express CD74 surface antigen.

Moderate Enhancement of DC Constitutive Maturation by hLL1

Human IgG can interact with DCs through FcR ligation and has opposing effects on DC maturation depending on which subtype(s) of FcR is involved. hLL1, as a humanized IgG, may interact with human DCs not only through CD74 but also through FcR expressed on DCs. For this reason, we speculated that hLL1 may influence DC functions through interaction with CD74 or FcR, or both. To investigate this, we tested the effect of hLL1 on DC constitutive maturation during in vitro culture of monocytes in the presence of hGM-CSF and hIL-4.

Since DC maturation is usually reflected by its morphological change, we also examined if hLL1 treatment has any effect on DC morphology. As shown in FIG. 4B, DCs treated with hLL1, at different doses for various days, in the absence or presence of GAH cross-linking, appeared healthy and intact. The hLL1-treated DCs exhibited some minor morphological changes featured with fiber-like cells, which are similar to but less obvious than LPS-treated DCs (not shown).

Figure 5A:
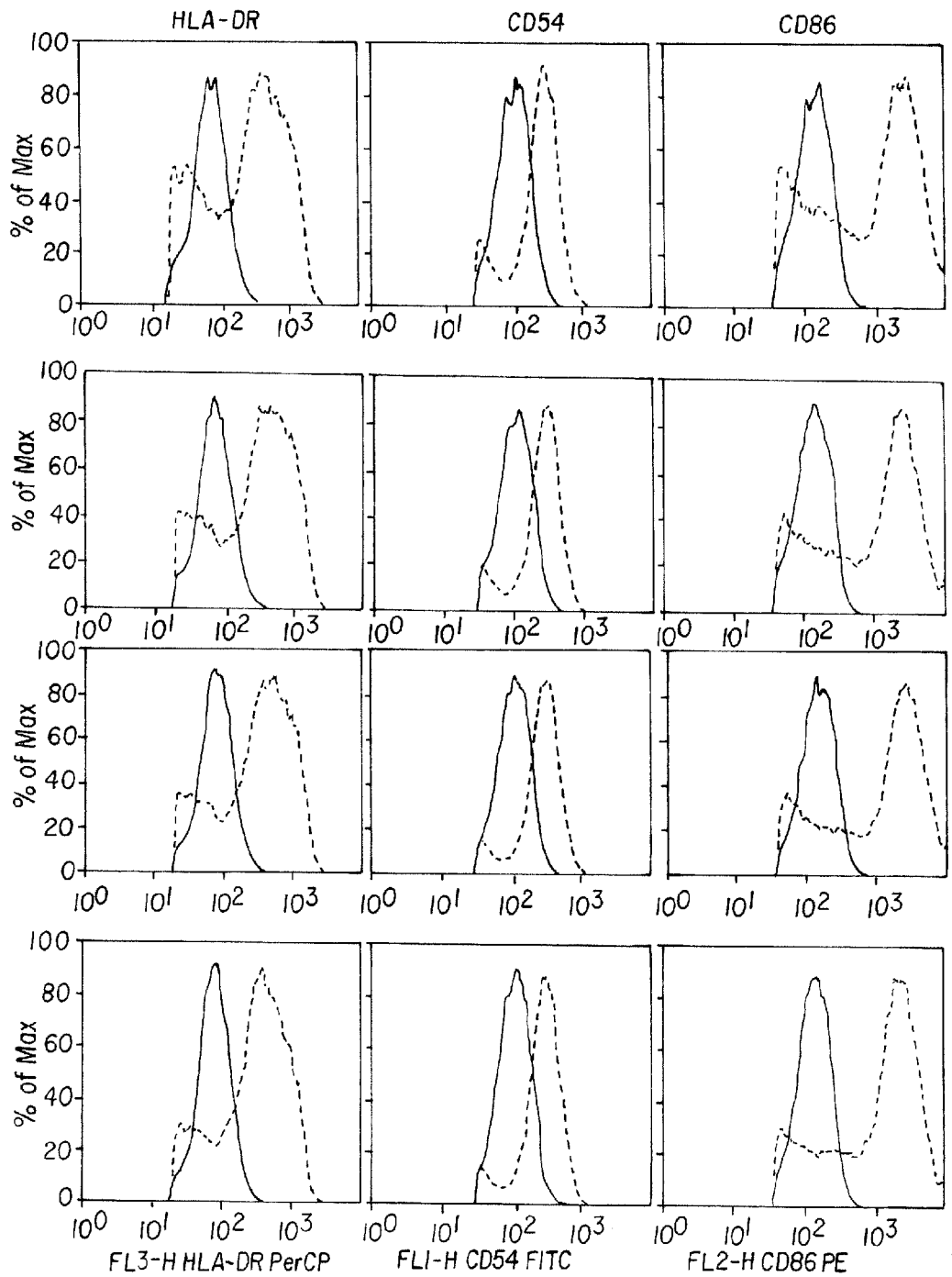
FIG. 5. Moderate enhancement of DC constitutive maturation by hLL1. The HLA-DR positive cell populations were gated from day 5 DCs derived from human monocytes in the presence of hGM-CSF and hIL-4. (A) The expression of antigen-presenting molecule HLA-DR, costimulatory molecule CD54 and CD86 was measured by flow cytometry. (B) Expression levels of antigen-presenting molecule HLA-DR, costimulatory molecule CD54 and CD86.
Figure 5B:
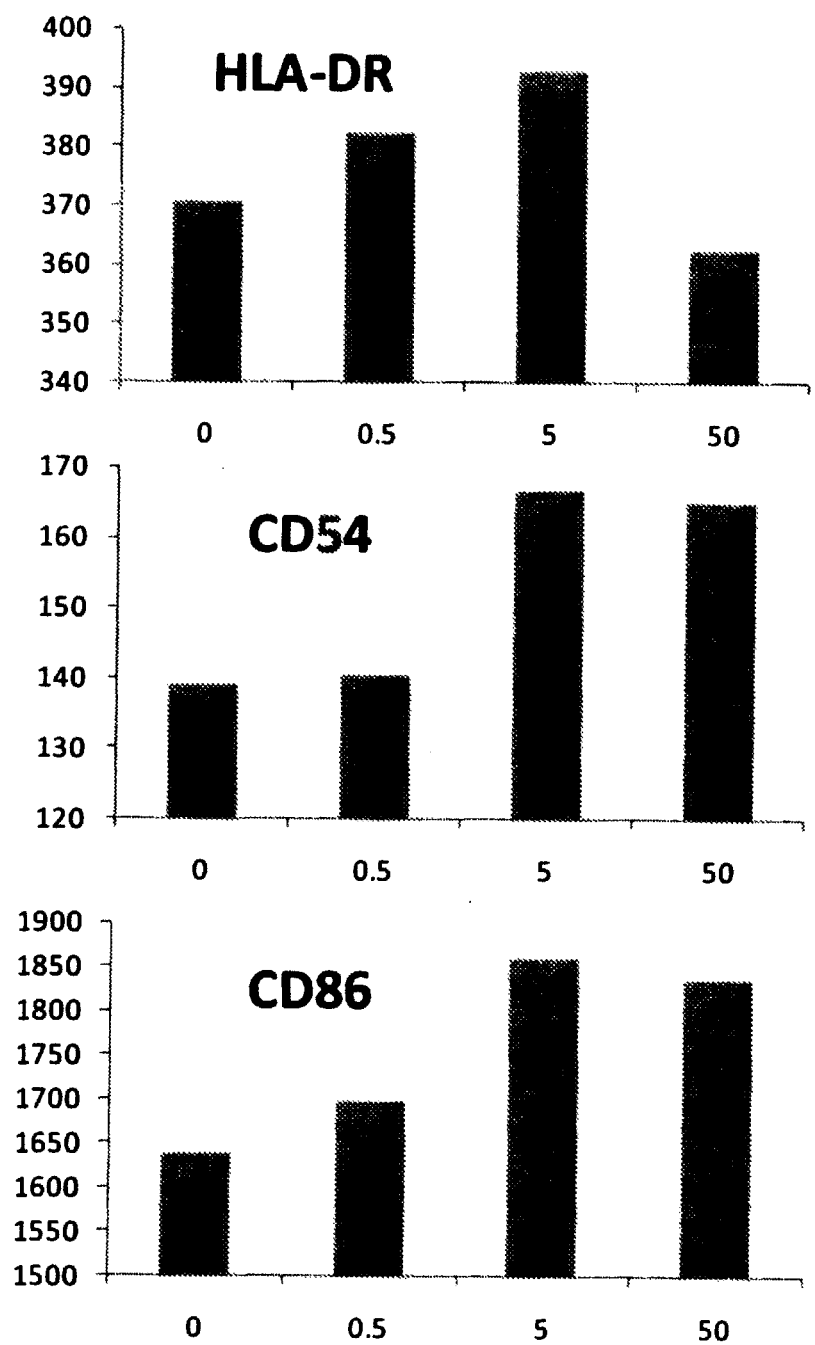

As mature DCs differ from immature DCs mainly in the upregulation of antigen-presenting and costimulatory molecule expression, altered cytokine production, and enhanced T-cell stimulatory ability, we then investigated if hLL1 has any effect on the expression level of antigen-presenting molecule HLA-DR and costimulatory molecules CD54 and CD86 in DCs (FIG. 5). The results show that hLL1 could upregulate HLA-DR, CD54, and CD86 in a dose-dependent manner within the range of hLL1 concentrations at 0.05-5 ug/ml (FIG. 5A). However, the effect was not strong, as the expression of HLA-DR and costimulatory molecules, CD54 and CD86, were only 10% upregulated at 5 ug/ml hLL1 compared to 0 ug/ml (FIG. 5B). At the highest concentration (50 μg/ml), the expression of HLA-DR, CD54 and CD86 was not further upregulated but slightly reduced, compared to hLL1 at 5 μg/ml (FIG. 5B). These results indicate that hLL1, although not potently, could enhance the constitutive maturation of DCs.

No Significant Influence on T Cell Expansion by hLL1-Treated DCs

Figure 6A:
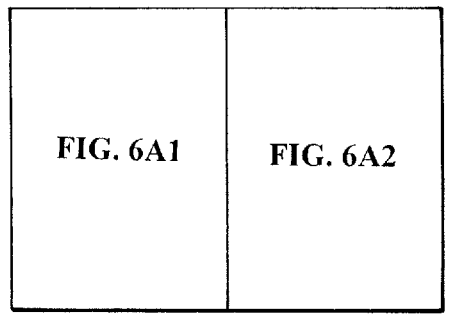
FIG. 6. No significant influence of hLL1 on DC-mediated T cell proliferation. The hLL1-treated DCs were co-cultured with CFSE-labeled allogeneic PBMCs for 8 (A) or 11 days (B). The expanded T cells were stained with Percp-conjugated mAb against CD4. The cell proliferation of total T cells, CD4+ and CD4– T cells were analyzed.
Figure 6B:
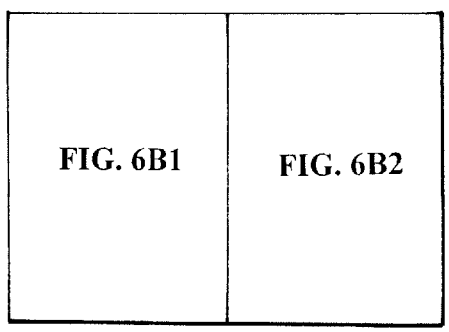
Figure 7:
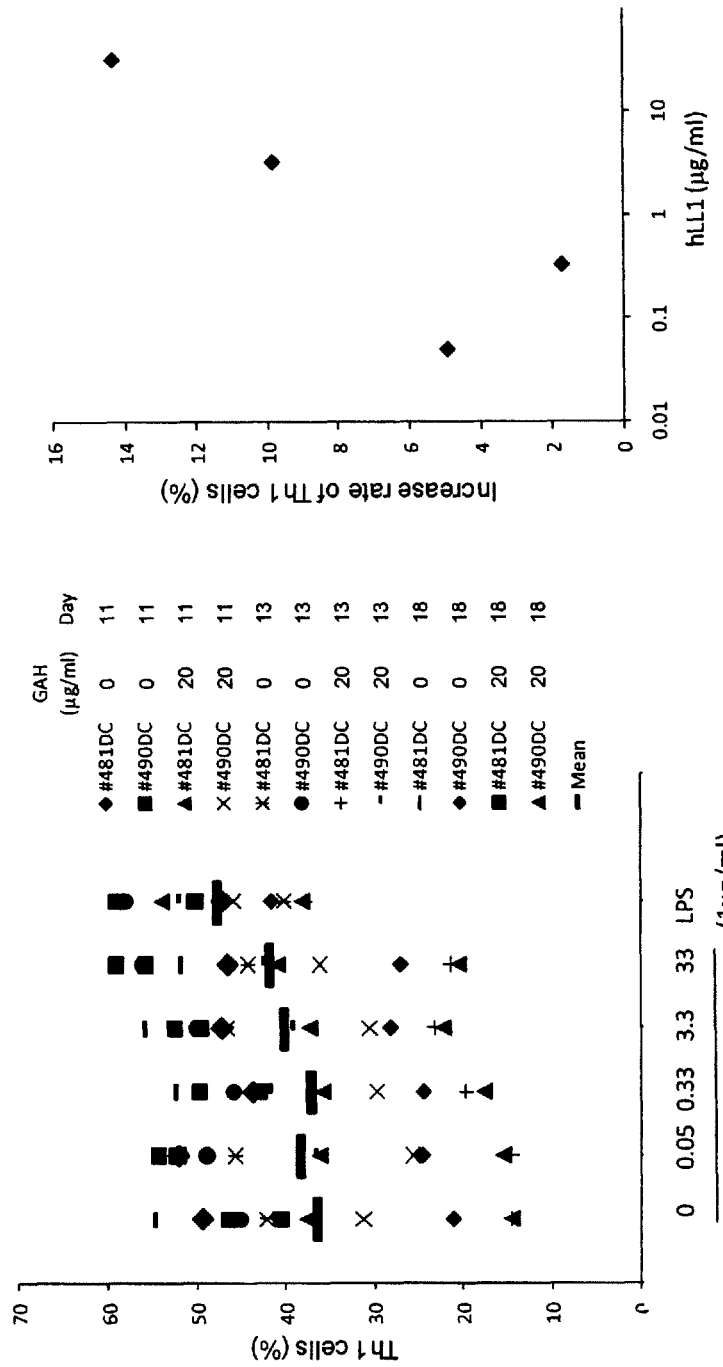
FIG. 7. Polarization of naïve CD4+ T cells by hLL1-treated DCs favoring the differentiation toward Th1 effector cells. Naïve CD4+ T cells isolated from human PBMCs using the depletion column with magnetic beads (MACS) were co-cultured with hLL1-treated allogeneic DCs. After different time points (day 11, 13, 18), the cells were harvested, stimulated with PMA and ionomycin, and analyzed with intracellular cytokine staining with fluorescence-labeled hIFN-gamma and hIL-4 antibodies. Th1/Th2/Th0 cells populations were gated and analyzed. The flow cytokine production in T cells stimulated by hLL1-treated DCs or by GAH-cross-linked hLL1-treated DCs was determined. (A) The data of Th1 responses in two donors, in the absence or presence of cross-linking by GAH, at different days after DC/T coculture, are shown. (B) The dose-effect curve for increasing Th1 populations by hLL1.

The functional difference between immature DCs and mature DCs is that mature DCs have a stronger capacity to stimulate T cell proliferation and expansion. Since hLL1 could enhance the constitutive maturation by upregulating the expression of HLA-DR, CD54 and CD86 expression in DCs (FIG. 5B), we determined whether this DC-maturing effect could be reflected by an enhanced T cell expansion by DCs. As shown in FIG. 6, DCs treated with hLL1 at 0.05 to 50

µg/ml did not influence the DC-mediated T cell expansion, including total T cells, CD4+ and CD4− T cells (FIG. 6). This result suggests that hLL1-enhanced DC constitutive maturation was not strong enough to be translated into an enhanced T cell stimulatory ability.

Polarization of Naïve CD4+ T Cells Toward Th1 Effector Cells by hLL1-Treated DCs However, DCs have another important function: the polarization of naïve CD4 T cells to differentiate into different effector cells, Th1, Th2, Th17, as well as newly defined Th17-1 cells. Th1 cells are critical for cellular immunity against intracellular pathogens and cancers, whereas induction of Th2 cells is responsible for humoral immunity. The IL-17-producing Th17 and Th17-1 cells are other polarized cell populations which have multiple functions in immunity to certain pathogens and autoimmune inflammation. The polarization of these effector cells is largely mediated through DC-secreted cytokines, the so-called "signal 3", that DCs provide to T cells in the DC/T cell synapse. The CD4+ naïve T cells can differentiate into Th1, Th2 and Th0 cells which mediate different effector functions, among which the Th1 effector cells play an essential role in maintaining CTL response against cancer and infectious diseases. We have shown that hLL1 at 0.05 to 50 µg/ml could enhance DC constitutive maturation in a weak but dose-dependent manner, but DCs treated with these concentrations of hLL1 didn't influence the DC-mediated T cell expansion (FIG. 6). We were then interested if the hLL1-treated DCs could influence the polarization of CD4+ naïve T cells. As shown in FIG. 6, hLL1-treated DCs polarized the CD4+ naïve T cells to differentiate toward more Th1 effector cells and fewer Th2 and Tnp cells. These results indicate that DCs can be functionally modulated by hLL1. As Th1 plays a crucial role in adaptive immunity against tumor and infectious diseases, hLL1 may have an adjuvant-like activity when used in vaccination.

Example 8

In Vitro Properties of 74-mCD20-Induction of hCD20-Specific Immunity by 74-mCD20 in Human PBMCs CD20 is a self antigen normally expressed on B cells, which is theoretically difficult to target by vaccine strategies due to immune tolerance. However, specific T-cell immune response to CD20 has been achieved in tumor bearing mice by vaccination with a minigene encoding the extracellular domain of human CD20 (Palomba et al., Clin Cancer Res 2005; 11:370-9), or a conjugate comprising the extracellular domain of human CD20 and a carrier protein with QS21 adjuvant (Roberts et al., Blood 2002; 99:3748-55). Several other reports have also demonstrated the feasibility of using xenoantigens to break immune tolerance, as shown for MUC1 in animal models (Ding et al., Blood 2008; 112:2817-25; Soares et al., J Immunol 2001; 166:6555-63) as well as in patients (Ramanathan et al., Cancer Immunol Immunother 2005; 54:254-64). To test whether 74-mCD20 could successfully induce hCD20-specific immunity and overcome the immune tolerance of CD20, the following experiment is performed.

Human DCs are generated from PBMCs by culturing for 5 days in the presence of hGM-CSF and hIL-4. The immature DCs are loaded with 74-mCD20, and matured by LPS plus IFN-gamma. The mature DCs are used to stimulate autologous PBMCs for 10 days. Restimulation with the same loaded DCs is performed twice weekly. After the last restimulation, the T cells are tested for their antigen specificity by measuring cytokine response (IFN-gamma) upon stimulation by sorted CD20-positive MM cancer stem cells. The CD20-negative MM cells are used as a control. The T cells show a positive reaction to CD20-positive MM cancer stem cells but not to control CD20-negative MM cells.

Specific Binding, Internalization and Intracellular Location of 74-mCD20 in Various Antigen Presenting Cells In Vitro Our preliminary data have shown that hLL1 efficiently and specifically binds with different APCs, including myeloid DC1 and myeloid DC2, plasmacytoid DC, B cells and monocytes. In order to confirm that 74-mCD20 has the same efficiency and specificity in binding with APCs as hLL1 alone, the following experiment is performed.

74-mCD20 and the control M1-mCD20 comprising the anti-MUC1 antibody hPAM4 linked to four copies of mCD20) are used. Binding assays are performed as follows. Briefly, 15 µg of 74-mCD20 or M1-mCD20 are labeled with a ZENON™ ALEXA FLUOR® 488 human IgG labeling kit (INVITROGEN®) following the manufacturer's instructions. The labeled preparations are used to stain the human PBMCs as described below.

Human PBMCs isolated from buffy coat using FICOLL-PAQUE™ are treated with human FcR blocking Reagent (Miltenyi Biotec, 1:20 dilution) at 4° C. for 10 min. The washed cells are stained with specifically labeled mAbs and analyzed by flow cytometry (FACSCALIBUR®). The labeled mAbs used for the study include FITC-labeled anti-CD74 mAb ALEXA FLUOR® 488-labeled 74-mCD20; ALEXA FLUOR® 488-labeled M1-mCD20; PE-conjugated anti-CD19 mAb (for B cells); PE-conjugated anti-CD14 mAb (for monocytes); and APC-conjugated mAb to BDCA-1 (for MDC1), BDCA-2 (for PDC), or BDCA-3 (for MDC2). A gating strategy is used for identification of B cells, monocytes, MDC1, MDC2, and PDC. Data were analyzed by FlowJo software for mean fluorescence intensity and positive cell populations expressing the surface markers.

To see if 74-mCD20 is internalized to endosomes for further processing to MHC class II presentation and MHC class I cross-presentation, the following experiment is performed. 74-mCD20 or M1-mCD20 is mixed with human PBMCs, and incubated at 4° C. for 1 hr, followed by extensive washing. The cells are then transferred to 37° C., fixed at different time points (0, 15, 30, or 45 min) and stained with ALEXA FLUOR®-labeled anti-human IgG secondary antibody with or without prior permeabilization. The mean fluorescence is determined by flow cytometry, and the amount of internalized antibody is calculated by subtracting the mean fluorescence in fixed cells (surface bound) from that recorded with fixed and permeabilized cells (internalized and surface bound) at various time points.

The results show that the 74-mCD20 DNL complex has the same efficiency and specificity in binding with APCs as hLL1 alone.

Example 9

Induction of hCD20-Specific Immune Responses by 74-mCD20 In Vivo

Intrahepatic injection of CD34+ human cord blood cells (HLA A1 healthy donor) into irradiated newborn Rag2−/− γc−/− mice is performed to generate the animal model for a reconstituted human adaptive immune system including human T, B, and DC cells, and structured primary and secondary lymphoid organs (Huff et al., J Clin Oncol. 2008, 26:2895-900; Yang and Chang, Cancer Invest. 2008, 26:741-55). These mice are called Hu-Rag2−/−γc−/− mice.

To assess the immune responses induced by 74-mCD20, human CD34+ cells reconstituted in Rag2−/−γc−/− mice are immunized weekly for three times with 74-mCD20 or M1-mCD20(50 μg per mouse), in combination with or without CpG (50 μg per mouse) for in vivo DC maturation. Five days after the last immunization, splenocytes of each animal are isolated and restimulated with HLA-matched MM cancer stem cells for cytokine (IFN-gamma) production, as assessed by intracellular cytokine staining with flow cytometry. The specific cytotoxicity against MM cancer stem cells is assessed by a calcein AM release assay with MM cancer stem cells as the target cells. The CD20+ MM cancer stem cells are isolated from the MM cell line RPMI18226 using magnetic beads. The stem cell property is verified by staining with aldehyde dehydrogenase. The results indicate that 74-mCD20 is capable of inducing an anti-hcd20 specific immune response in vivo.

Example 10

Therapeutic Potential of 74-mCD20 Against MM Cancer Stem Cells: In Vivo Evaluation by hPBMC/NOD/SCID Mouse Model or Adoptive Transfer The best way for in vivo evaluation of the therapeutic effect of 74-mCD20 is to immunize an animal model that can support both the growth of MM and the development of a human adaptive immune system. Since human CD34+ cell-reconstituted Rag2−/−γc−/− mice are immune-competent, which may not support MM growth, the hPBMC/NOD/SCID mouse model is used to test the therapeutic effect of 74-mCD20 against MM stem cells. The NOD/SCID mice have been used for engraftment of clonogenic multiple myeloma stem cells by Matsui et al. (Blood 2004, 103:2332-6; Cancer Res 2008, 68:190-7).

The NOD/SCID mice are also used for evaluating the therapeutic effect by co-engraftment of tumor cells and hPBMC. By carefully adjusting the cell numbers infused, this model can support both tumor growth and hPBMC engraftment, and has been used for testing the effect of an in vivo vaccine targeting DC-SIGN.

Four to six-week-old female NOD/SCID mice (Jackson Laboratories, Barr Harbor, Me.) are irradiated with 300 cGy (84 cGy/min using a 137Cs gamma irradiator). 12-16 h later, sorted CD20+ MM cancer stem cells (2 million) are injected via dorsal tail vein. Meanwhile, a mixture of human PBMCs (3 million), immature DC (30,000) and the DNL vaccine is injected into the mice subcutaneously. At certain time points (days), mice are euthanatized and bone marrow is harvested from the long bones and the engraftment and therapeutic efficacy are determined by staining for human CD138$^+$ MM cells.

In order to further evaluate the therapeutic potential of 74-mCD20, an alternative method by adoptive transfer is used to test the vaccine-elicited cytotoxicity against MM stem cells. The human CD34+ cell-reconstituted Rag2−/−γc−/− mice are immunized with 74-mCD20 as described above. The splenocytes are harvested and injected via the tail vein into NOD/SCID mice engrafted with CD20+ MM cancer stem cells. At certain time points (days), mice are euthanatized and bone marrow is harvested from the long bones and the engraftment and therapeutic efficacy are determined by staining for human CD138+ MM cells. The results confirm that 74-mCD20 is capable of inducing an immune response against CD20$^+$ MM stem cells in vivo.

Example 11

Generation of DDD2-mPAP and DNL Vaccine Complex

A DDD2 conjugated PAP xenoantigen is generated from murine prostatic acid phosphatase according to the method of Example 4. The efficacy of dendritic cell based vaccination with a PAP xenoantigen has been previously disclosed (Fong et al. J Immunol 2001, 167:7150-56). A DDD2-mPAP-pdHL2 expression vector is constructed as described in Example 4 and the DDD2-mPAP xenoantigen fusion protein is expressed in cell culture according to Example 4. The murine prostatic acid phosphatase sequence is disclosed, for example, in the NCBI database at Accession No. AAF23171. A DDD2-mPAP-6His fusion protein ("6His" disclosed as SEQ ID NO: 28) is expressed and purified by immobilized metal affinity chromatography (IMAC) as described in Example 4.

A DNL construct comprising one copy of $C_{H3}$-AD2-IgG-hLL1 (anti-CD74) and four copies of DDD2-mPAP is prepared according to the methods of Example 5. The hLL1 IgG moiety comprises an AD2 sequence attached to the C-terminal end of each heavy chain of the hLL1 IgG. A DNL reaction is performed by mixing hLL1 IgG-AD2 and DDD2-mPAP in PBS containing 1 mM reduced glutathione. On the next day oxidized glutathione is added to a final concentration of 2 mM and the reaction mixture is purified on a Protein A column 24 h later. Two copies of the DDD2-mPAP are attached to each AD2 moiety, resulting in a DNL complex comprising one hLL1 IgG moiety and four mPAP xenoantigen moieties.

Administration of DNL vaccine anti-CD74-mPAP to subjects with prostate cancer induces an immune response against PAP expressing prostatic cancer stem cells. The immune response is effective to reduce or eliminate prostatic cancer cells in the subjects.

Example 12

Generation of DDD2-mEGFR and DNL Vaccine Complex

A DDD2 conjugated EGFR xenoantigen is generated from murine EGFR according to the method of Example 4. The efficacy of EGFR xenoantigen at inducing a humoral immune response has been previously disclosed (Fang et al. Int J Mol Med 2009, 23:181-88). A DDD2-mEGFR-pdHL2 expression vector comprising the extracellular domain of murine EGFR is constructed as described in Example 4 and the DDD2-mEGFR xenoantigen fusion protein is expressed in cell culture according to Example 4. The murine EGFR sequence is disclosed, for example, in the NCBI database at Accession No. AAG43241. A DDD2-mEGFR-6His fusion protein ("6His" disclosed as SEQ ID NO: 28) is expressed and purified by immobilized metal affinity chromatography (IMAC) as described in Example 4.

A DNL construct comprising one copy of $C_{H3}$-AD2-IgG-hLL1 (anti-CD74) and four copies of DDD2-mEGFR is prepared according to the methods of Example 5. The hLL1 IgG moiety comprises an AD2 sequence attached to the C-terminal end of each heavy chain of the hLL1 IgG. A DNL reaction is performed by mixing hLL1 IgG-AD2 and DDD2-mEGFR in PBS containing 1 mM reduced glutathione. On the next day oxidized glutathione is added to a final concentration of 2 mM and the reaction mixture is purified on a Protein A column 24 h later. Two copies of the DDD2-mEGFR are attached to each AD2 moiety, resulting in a DNL complex comprising one hLL1 IgG moiety and four mEGFR xenoantigen moieties.

Administration of DNL vaccine anti-CD74-mEGFR to subjects with EGFR-expressing NSCLC induces an immune response against EGFR-expressing cancer stem cells. The immune response is effective to reduce or eliminate EGFR positive cancer cells in the subjects.

The skilled artisan will realize that DNL-based vaccines incorporating xenoantigen moieties corresponding to a wide variety of tumor-associated antigens may be constructed and utilized according to the techniques described herein.

All of the COMPOSITIONS and METHODS disclosed and claimed herein can be made and used without undue experimentation in light of the present disclosure. While the compositions and methods have been described in terms of preferred embodiments, it is apparent to those of skill in the art that variations may be applied to the COMPOSITIONS and METHODS and in the steps or in the sequence of steps of the METHODS described herein without departing from the concept, spirit and scope of the invention. More specifically, certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of treating a B-cell cancer comprising:
   a) obtaining a complex consisting essentially of:
      iii) an antibody moiety that binds to a CD74 dendritic cell antigen, wherein the antibody moiety is attached to a DDD (dimerization and docking domain) moiety, wherein the amino acid sequence of the DDD moiety is selected from the group consisting of SEQ ID NO: 1 and SEQ ID NO: 2; and
      iv) a tumor antigen moiety that is a CD20 xenoantigen, wherein the antigen moiety is attached to an AD (anchor domain) moiety, wherein the amino acid sequence of the AD moiety is selected from the group consisting of SEQ ID NO:3; SEQ ID NO:4; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15 and SEQ ID NO:16; wherein two copies of the DDD moiety form a dimer that binds to the AD moiety to form the complex; and
   b) administering the complex to a human subject with a B-cell cancer.

2. The method of claim 1, wherein the cancer is selected from the group consisting of B-cell lymphoma, B-cell leukemia, acute lymphoblastic leukemia, chronic lymphocytic leukemia, follicular lymphoma, mantle cell lymphoma, small lymphocytic lymphoma, diffuse B-cell lymphoma, marginal zone lymphoma, multiple myeloma, Burkitt lymphoma, Hodgkin's lymphoma and non-Hodgkin's lymphoma.

3. The method of claim 2, wherein the cancer is multiple myeloma.

4. The method of claim 1, further comprising administering one or more therapeutic agents to the subject, wherein the one or more therapeutic agents are selected from the group consisting of an immunomodulator, an anti-angiogenic agent, a cytokine, a chemokine, a growth factor, a hormone, a drug, a prodrug, an enzyme, a pro-apoptotic agent, a photoactive therapeutic agent, a cytotoxic agent, a chemotherapeutic agent; and a toxin.

5. The method of claim 4, wherein the one or more therapeutic agents are administered to the subject prior to or simultaneously with the complex.

6. The method of claim 4, wherein the drug is selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, SN-38, doxorubicins and their analogs, antimetabolites, alkylating agents, antimitotics, anti-angiogenic agents, tyrosine kinase inhibitors, mTOR inhibitors, heat shock protein (HSP90) inhibitors, proteosome inhibitors, HDAC inhibitors, pro-apoptotic agents, methotrexate and CPT-11.

7. The method of claim 4, wherein the toxin selected from the group consisting of ricin, abrin, alpha toxin, saporin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin.

8. The method of claim 4, wherein the immunomodulator is selected from the group consisting of a cytokine, a stem cell growth factor, a lymphotoxin, a hematopoietic factor, a colony stimulating factor (CSF), an interleukin (IL), an interferon (IFN), erythropoietin, thrombopoietin, tumor necrosis factor (TNF), granulocyte-colony stimulating factor (G-CSF), granulocyte macrophage-colony stimulating factor (GM-CSF), and the stem cell growth factor designated "S1 factor".

9. The method of claim 8, wherein the cytokine is selected from the group consisting of tumor necrosis factor-α, tumor necrosis factor-β, mullerian-inhibiting substance, thrombopoietin (TPO), platelet-growth factor, TGF-α, TGF-β, insulin-like growth factor-I, insulin-like growth factor-II, erythropoietin (EPO), osteoinductive factors, interferon-α, interferon-β, interferon-γ, macrophage-CSF (M-CSF), IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, angiostatin, thrombospondin, endostatin, and lymphotoxin (LT).

10. The method of claim 3, further comprising inducing an immune response against $CD138^{neg}CD20^+$ multiple myeloma (MM) stem cells.

11. The method of claim 3, further comprising inducing apoptosis of $CD138^{neg}CD20^+$ MM stem cells.

12. The method of claim 3, wherein said administration is effective to inhibit or eliminate MM stem cells.

13. The method of claim 6, wherein the drug is a COX-2 inhibitor.

14. A method of inducing an immune response against $CD138^{neg}CD20^+$ MM stem cells comprising:
 a) obtaining a complex consisting essentially of
  i) an antibody moiety that binds to a dendritic cell antigen selected from the group consisting of CD209 (DC-SIGN), CD74 and CD205, wherein the antibody moiety is attached to a DDD (dimerization and docking domain) moiety, wherein the amino acid sequence of the DDD moiety is selected from the group consisting of SEQ ID NO: 1 and SEQ ID NO: 2; and
  ii) a CD20 xenoantigen moiety attached to an AD (anchor domain) moiety, wherein the amino acid sequence of the DDD moiety is selected from the group consisting of SEQ ID NO:3; SEQ ID NO:4; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15 and SEQ ID NO:16; wherein two copies of the DDD moiety form a dimer that binds to the AD moiety to form the complex; and
 b) administering the complex to a human subject with multiple myeloma.

15. The method of claim 14, further comprising inducing apoptosis of $CD138^{neg}CD20^+$ MM stem cells.

16. The method of claim 14, wherein said administration is effective to inhibit or eliminate MM stem cells.

* * * * *